United States Patent
Jung et al.

(10) Patent No.: US 11,299,466 B2
(45) Date of Patent: Apr. 12, 2022

(54) COMPOUND, AND ORGANIC ELECTRONIC ELEMENT COMPRISING SAME

(71) Applicant: LG Chem, Ltd., Seoul (KR)

(72) Inventors: Min Woo Jung, Daejeon (KR); Dong Hoon Lee, Daejeon (KR); Tae Yoon Park, Daejeon (KR); Jungoh Huh, Daejeon (KR); Boonjae Jang, Daejeon (KR); Seongmi Cho, Daejeon (KR); Minyoung Kang, Daejeon (KR); Dong Uk Heo, Daejeon (KR); Miyeon Han, Daejeon (KR); Jungha Lee, Daejeon (KR)

(73) Assignee: LG Chem, Ltd.

( * ) Notice: Subject to any disclaimer, the term of this patent is extended or adjusted under 35 U.S.C. 154(b) by 544 days.

(21) Appl. No.: 16/090,681

(22) PCT Filed: Apr. 11, 2017

(86) PCT No.: PCT/KR2017/003907
§ 371 (c)(1),
(2) Date: Oct. 2, 2018

(87) PCT Pub. No.: WO2017/179883
PCT Pub. Date: Oct. 19, 2017

(65) Prior Publication Data
US 2020/0010433 A1  Jan. 9, 2020

(30) Foreign Application Priority Data
Apr. 12, 2016 (KR) .................. 10-2016-0045043

(51) Int. Cl.
*C07D 251/24* (2006.01)
*C07D 263/57* (2006.01)
(Continued)

(52) U.S. Cl.
CPC ......... *C07D 251/24* (2013.01); *C07D 263/57* (2013.01); *C07D 277/66* (2013.01);
(Continued)

(58) Field of Classification Search
CPC ............... C07D 251/24; C07D 263/57; C07D 277/66; C07D 239/26; C07D 235/06;
(Continued)

(56) References Cited

U.S. PATENT DOCUMENTS 6,507,048 B1   1/2003  Makiya
7,939,155 B2 *  5/2011  Chen ..................... H05B 33/14
                                              428/90
(Continued)

FOREIGN PATENT DOCUMENTS

CN    101041773 A   9/2007
CN    102276514 A   12/2011
(Continued)

OTHER PUBLICATIONS

Optical Materials, 35 (2013), pp. 2201-2207. (Year: 2013).*
(Continued)

*Primary Examiner* — Dawn L Garrett
(74) *Attorney, Agent, or Firm* — Lerner, David, Littenberg, Krumholz & Mentlik, LLP

(57) ABSTRACT

The present specification relates to a compound of Chemical Formula 1 and an organic electronic device comprising the same.

11 Claims, 1 Drawing Sheet

(51) Int. Cl.
*C07D 277/66* (2006.01)
*H01L 51/00* (2006.01)
*H01L 51/50* (2006.01)
*C09K 11/06* (2006.01)

(52) U.S. Cl.
CPC .......... *C09K 11/06* (2013.01); *H01L 51/0052* (2013.01); *H01L 51/0062* (2013.01); *H01L 51/0067* (2013.01); *H01L 51/0069* (2013.01); *H01L 51/0071* (2013.01); *H01L 51/0072* (2013.01); *H01L 51/0073* (2013.01); *H01L 51/0074* (2013.01); *H01L 51/5072* (2013.01); *H01L 51/5092* (2013.01); *C09K 2211/1044* (2013.01); *C09K 2211/1059* (2013.01); *H01L 51/5076* (2013.01); *H01L 51/5096* (2013.01)

(58) Field of Classification Search
CPC .............. H01L 51/0071; H01L 51/0052; H01L 51/5072; H01L 51/5092; H01L 51/0062; H01L 51/0069; H01L 51/0067; H01L 51/0072; H01L 51/0073; H01L 51/0074; H01L 51/0512; H01L 51/42; H01L 51/5076; H01L 51/5096; H01L 51/0054; H01L 51/0058; C09K 11/06; C09K 2211/1059; C09K 2211/1044; Y02E 10/549

See application file for complete search history.

(56) References Cited

U.S. PATENT DOCUMENTS

| | | |
|---|---|---|
| 2004/0110958 A1 | 6/2004 | Nishiyama et al. |
| 2004/0251816 A1 | 12/2004 | Leo et al. |
| 2005/0222352 A1 | 10/2005 | Litz et al. |
| 2007/0167614 A1 | 7/2007 | Chen et al. |
| 2007/0228941 A1 | 10/2007 | Abe et al. |
| 2009/0326236 A1 | 12/2009 | Suh et al. |
| 2010/0071769 A1 | 3/2010 | Bae et al. |
| 2012/0194062 A1 | 8/2012 | Osaka et al. |
| 2012/0228554 A1 | 9/2012 | Franz et al. |
| 2013/0079517 A1 | 3/2013 | Schafer et al. |
| 2013/0256645 A1 | 10/2013 | Min et al. |
| 2014/0117329 A1 | 5/2014 | Lee et al. |
| 2014/0329867 A1 | 11/2014 | Radtke et al. |
| 2014/0353624 A1 | 12/2014 | Kim et al. |
| 2016/0276596 A1* | 9/2016 | Jang ............ H01B 1/04 |
| 2017/0018718 A1 | 1/2017 | Jang et al. |
| 2017/0098777 A1 | 4/2017 | Huh et al. |
| 2018/0354934 A1* | 12/2018 | He ............ C07D 251/24 |

FOREIGN PATENT DOCUMENTS

| | | |
|---|---|---|
| CN | 103374040 A | 10/2013 |
| CN | 103936653 A | 7/2014 |
| CN | 104178120 A | 12/2014 |
| CN | 104371706 A | 2/2015 |
| JP | 2007223928 A | 9/2007 |
| KR | 20120031684 A | 4/2012 |
| KR | 20120060611 A | 6/2012 |
| KR | 20120120906 | 11/2012 |
| KR | 101219481 B1 | 1/2013 |
| KR | 20130069431 A | 6/2013 |
| KR | 101537500 B1 | 7/2015 |
| WO | 2003012890 A2 | 2/2003 |
| WO | 2014042420 A1 | 3/2014 |
| WO | 2014061991 A1 | 4/2014 |
| WO | 2015152650 A1 | 10/2015 |
| WO | WO 2018/117562 A1 * | 6/2018 |

OTHER PUBLICATIONS

Machine translation of WO 2018/117562 A1 (publication date: Jun. 2018) (Year: 2018).*

Liang W, Gao Z, Song W, Su J, Guo K, Dong Q, Huang J, Wong WY. A novel host material with high thermal stability for green electrophosphorescent device. Tetrahedron. Mar. 17, 2016;72(11):1505-10.

Mondal E, Hung WY, Chen YH, Cheng MH, Wong KT. Molecular Topology Tuning of Bipolar Host Materials Composed of Fluorene-Bridged Benzimidazole and Carbazole for Highly Efficient Electrophosphorescence. Chemistry—A European Journal. Aug. 5, 2013;19(32):10563-72.

International Search Report for PCT/KR2017/003907 dated Jul. 20, 2017.

* cited by examiner

【FIG. 1】
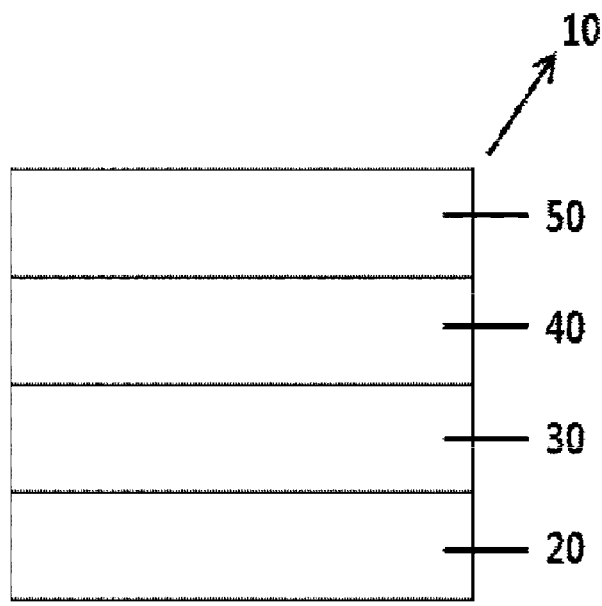
【FIG. 2】
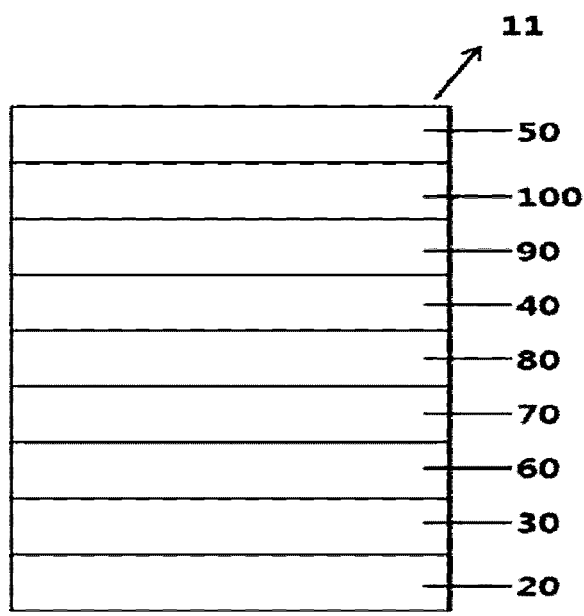

COMPOUND, AND ORGANIC ELECTRONIC ELEMENT COMPRISING SAME

CROSS-REFERENCE TO RELATED APPLICATIONS

The present application is a national phase entry under 35 U.S.C. § 371 of International Application No. PCT/KR2017/003907 filed Apr. 11, 2017, which claims priority from Korean Patent Application No. 10-2016-0045043 filed Apr. 12, 2016, all of which are incorporated herein by reference.

TECHNICAL FIELD

The present specification relates to a compound and an organic electronic device comprising the same.

BACKGROUND ART

A typical example of an organic electronic device comprises an organic light emitting device. An organic light emission phenomenon generally refers to a phenomenon converting electrical energy to light energy using an organic material. An organic light emitting device using an organic light emission phenomenon normally has a structure comprising an anode, a cathode, and an organic material layer therebetween. Herein, the organic material layer is often formed in a multilayer structure formed with different materials in order to increase efficiency and stability of the organic light emitting device, and for example, may be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

PRIOR ART DOCUMENTS

Patent Documents

International Patent Application Laid-Open Publication No. 2003-012890

DISCLOSURE

Technical Problem

The present specification is directed to providing a compound and an organic electronic device comprising the same.

Technical Solution

One embodiment of the present specification provides a compound represented by the following Chemical Formula 1.

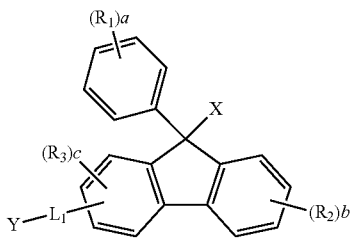

[Chemical Formula 1]

In Chemical Formula 1,

X is a substituted phenyl group; a substituted or unsubstituted dicyclic or higher aryl group; or a substituted or unsubstituted heterocyclic group, $L_1$ is a direct bond; a substituted or unsubstituted arylene group; or a substituted or unsubstituted heteroarylene group, Y is selected from among the following structural formulae,

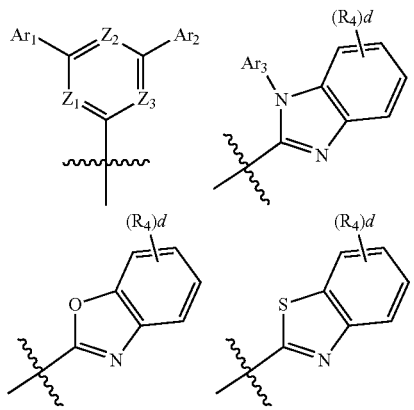

two or more of $Z_1$ to $Z_3$ are N, and the rest are N or CR, $Ar_1$ to $Ar_3$ are the same as or different from each other, and each independently hydrogen; deuterium; a halogen group; a substituted or unsubstituted alkyl group; a substituted or unsubstituted cycloalkyl group; a substituted or unsubstituted phosphine oxide group; a substituted or unsubstituted aryl group; or a substituted or unsubstituted heteroaryl group, R and $R_1$ to $R_4$ are the same as or different from each other, and each independently hydrogen; deuterium; a halogen group; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted alkenyl group; a substituted or unsubstituted silyl group; a substituted or unsubstituted boron group; a substituted or unsubstituted phosphine oxide group; a substituted or unsubstituted amine group; a substituted or unsubstituted arylamine group; a substituted or unsubstituted aryl group; or a substituted or unsubstituted heteroaryl group, a is an integer of 1 to 5,
b is an integer of 1 to 4,
c is an integer of 1 to 3, d is an integer of 1 to 4, when a is 2 or greater, a plurality of $R_1$s are the same as or different from each other, when b is 2 or greater, a plurality of $R_2$s are the same as or different from each other, when c is 2 or greater, a plurality of $R_3$s are the same as or different from each other, and when d is 2 or greater, a plurality of $R_4$s are the same as or different from each other.

Another embodiment of the present specification provides an organic electronic device comprising a first electrode; a second electrode provided opposite to the first electrode; and one or more organic material layers provided between the first electrode and the second electrode, wherein one or more layers of the organic material layers comprise the compound described above.

Advantageous Effects

A compound according to one embodiment of the present specification can be used in an organic electronic device comprising an organic light emitting device to lower a driving voltage of the organic electronic device, enhance luminance efficiency, and enhance a lifespan property of the device with thermal stability of the compound.

DESCRIPTION OF DRAWINGS

FIG. 1 illustrates an organic electronic device (10) according to one embodiment of the present specification.

FIG. 2 illustrates an organic electronic device (11) according to another embodiment of the present specification.

REFERENCE NUMERAL 10, 11: Organic Light Emitting Device
20: Substrate
30: First Electrode
40: Light Emitting Layer
50: Second Electrode
60: Hole Injection Layer
70: Hole Transfer Layer
80: Electron Blocking Layer
90: Electron Transfer Layer
100: Electron Injection Layer

MODE FOR DISCLOSURE

Hereinafter, the present specification will be described in more detail.

The present specification provides a compound represented by Chemical Formula 1.

Examples of the substituents in the present specification are described below, however, the substituents are not limited thereto.

In the present specification,

means a linking site.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

The term "substituted or unsubstituted" in the present specification means being substituted with one, two or more substituents selected from the group consisting of deuterium; a halogen group; a nitrile group; a nitro group; a hydroxyl group; a carbonyl group; an ester group; an imide group; an amide group; an alkoxy group; an alkyl group; a cycloalkyl group; an aryloxy group; an alkylthioxy group; an arylthioxy group; an alkylsulfoxy group; an alkenyl group; a silyl group; a boron group; an amine group; a phosphine oxide group; an aryl group; an arylamine group; and a heteroaryl group comprising one or more of N, O, S, Se and Si atoms, or being substituted with a substituent linking two or more substituents among the substituents illustrated above, or having no substituents.

In the present specification, examples of the halogen group may comprise fluorine, chlorine, bromine or iodine.

In the present specification, the number of carbon atoms of the carbonyl group is not particularly limited, but is preferably from 1 to 50. Specifically, compounds having structures as below may be included, but the carbonyl group is not limited thereto.

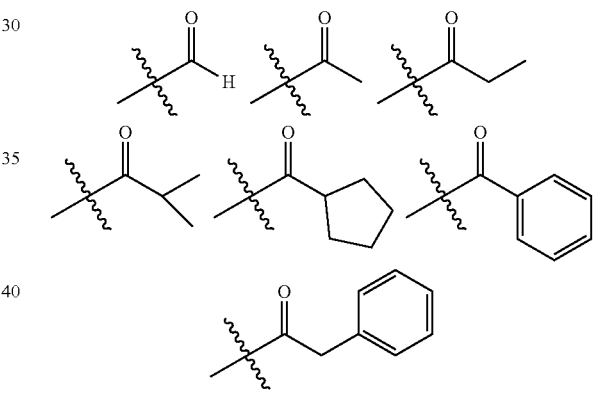

In the present specification, the number of carbon atoms of the ester group is not particularly limited, but is preferably from 1 to 30. Specifically, compounds having the following structural formulae may be included, but the ester group is not limited thereto.

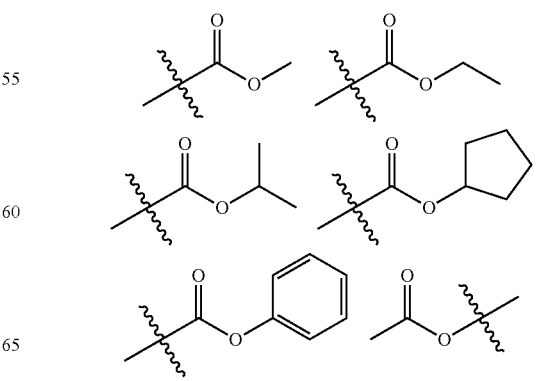

-continued

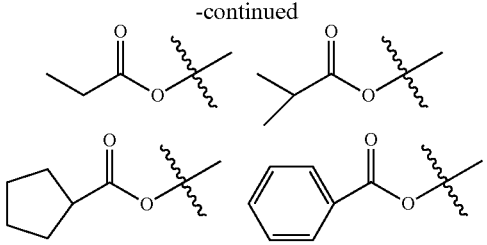

In the present specification, the number of carbon atoms of the imide group is not particularly limited, but is preferably from 1 to 30. Specifically, compounds having structures as below may be included, but the imide group is not limited thereto.

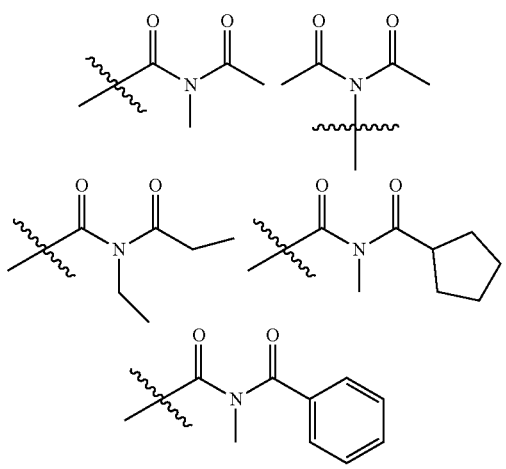

In the present specification, in the amide group, the nitrogen of the amide group may be substituted with a linear, branched or cyclic alkyl group having 1 to 30 carbon atoms or an aryl group having 6 to 30 carbon atoms. Specifically, compounds having the following structural formulae may be included, but the amide group is not limited thereto.

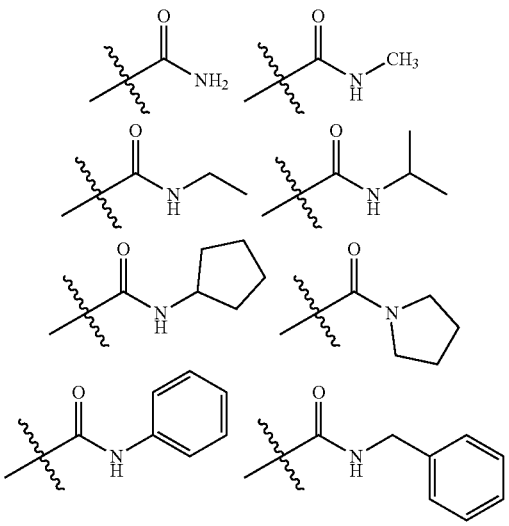

In the present specification, the alkyl group may be linear or branched, and the number of carbon atoms is not particularly limited, but is preferably from 1 to 50. Specific examples thereof may comprise methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, iso-pentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentyl-methyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

In the present specification, the cycloalkyl group is not particularly limited, but preferably has 3 to 60 carbon atoms, and specific examples thereof may comprise cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group may be linear, branched or cyclic. The number of carbon atoms of the alkoxy group is not particularly limited, but is preferably from 1 to 20. Specific examples thereof may comprise methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the alkenyl group may be linear or branched, and although not particularly limited thereto, the number of carbon atoms is preferably from 2 to 40. Specific examples thereof may comprise vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, the silyl group is a substituent comprising Si with the Si element directly linked as a radical, and is represented by —SiR$_{104}$R$_{105}$R$_{106}$. R$_{104}$ to R$_{106}$ are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group may comprise a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the boron group may be —BR$_{100}$R$_{101}$. R$_{100}$ and R$_{101}$ are the same as or different from each other, and may be each independently selected from the group consisting of hydrogen; deuterium; halogen; a nitrile group; a substituted or unsubstituted monocyclic or multicyclic cycloalkyl group having 3 to 30 carbon atoms; a substituted or unsubstituted linear or branched alkyl group having 1 to 30 carbon atoms; a substituted or unsubstituted monocyclic or multicyclic aryl group having 6 to 30 carbon atoms; and a substituted or unsubstituted monocyclic or multicyclic heteroaryl group having 2 to 30 carbon atoms.

When the aryl group is a multicyclic aryl group, the number of carbon atoms is not particularly limited, but is preferably from 10 to 24. Specific examples of the multicyclic aryl group may comprise a naphthyl group, a biphenyl group, a terphenyl group, a quaterphenyl group, an anthracenyl group, a phenanthryl group, a triphenylene group, a pyrenyl group, a perylenyl group, a chrysenyl group, a fluorenyl group and the like, but are not limited thereto.

In the present specification, the fluorenyl group may be substituted, and adjacent substituents may bond to each other to form a ring.

When the fluorenyl group is substituted,

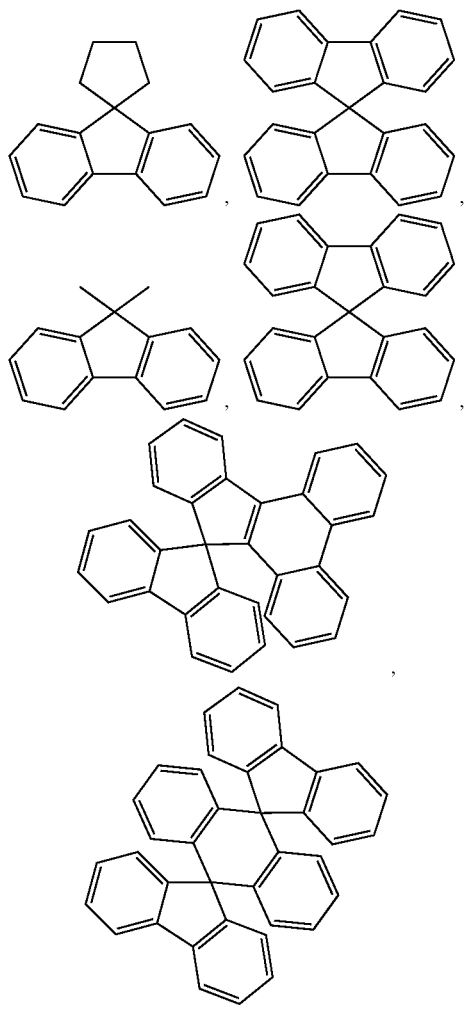

and the like may be included. However, the compound is not limited thereto.

In the present specification, the heteroaryl group is a heterocyclic group comprising one or more of N, O, S, Si and Se as a heteroatom, and although not particularly limited thereto, the number of carbon atoms is preferably from 2 to 60. Examples of the heteroaryl group may comprise a thiophene group, a furan group, a pyrrole group, an imidazole group, a triazole group, an oxazole group, an oxadiazole group, a triazole group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a dibenzofuranyl group and the like, but are not limited thereto.

In the present specification, a hydrocarbon ring or a heteroring may be selected from among the examples of the cycloalkyl group, the aryl group or the heteroaryl group described above except for being monovalent, and may have a form of monocyclic or multicyclic, aliphatic or aromatic, or a fused form thereof, but is not limited thereto.

In the present specification, the amine group means a primary amine in which at least one hydrogen atoms of the amino group (—NH$_2$) is substituted with other substituents, and is represented by —NR$_{107}$R$_{108}$. R$_{107}$ and R$_{108}$ are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group (however, at least one of R$_{107}$ and R$_{108}$ is not hydrogen). For example, the amine group may be selected from the group consisting of —NH$_2$; a monoalkylamine group; a dialkylamine group; an N-alkylarylamine group; a monoarylamine group; a diarylamine group; an N-arylheteroarylamine group; an N-alkylheteroarylamine group, a monoheteroarylamine group and a diheteroarylamine group, and although not particularly limited thereto, the number of carbon atoms is preferably from 1 to 30. Specific examples of the amine group may comprise a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a ditolylamine group, an N-phenyltolylamine group, a triphenylamine group, an N-phenylbiphenylamine group; an N-phenylnaphthylamine group; an N-biphenylnaphthylamine group; an N-naphthylfluorenylamine group; an N-phenylphenanthrenylamine group; an N-biphenylphenanthrenylamine group; an N-phenylfluorenylamine group; an N-phenylterphenylamine group; an N-phenanthrenylfluorenylamine group; an N-biphenylfluorenylamine group and the like, but are not limited thereto.

In the present specification, specific examples of the phosphine oxide group may comprise a diphenylphosphine oxide group, a dinaphthylphosphine oxide group and the like, but are not limited thereto.

In the present specification, the aryl group in the aryloxy group, the arylthioxy group, the arylsulfoxy group, the N-arylalkylamine group, the N-arylheteroarylamine group and the arylphosphine group is the same as the examples of the aryl group described above. Specific examples of the aryloxy group may comprise a phenoxy group, a p-tolyloxy group, an m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group and the like, and specific examples of the arylthioxy group may comprise a phenylthioxy group, a 2-methylphenylthioxy group, a 4-tert-butylphenylthioxy group and the like, and specific examples of the arylsulfoxy group may comprise a benzenesulfoxy group, a p-toluenesulfoxy group and the like, however, the aryloxy group, the arylthioxy group and the arylsulfoxy group are not limited thereto.

In the present specification, examples of the arylamine group comprise a substituted or unsubstituted monoarylamine group, a substituted or unsubstituted diarylamine group, or a substituted or unsubstituted triarylamine group. The aryl group in the arylamine group may be a monocyclic aryl group or a multicyclic aryl group. The arylamine group comprising two or more aryl groups may comprise monocyclic aryl groups, multicyclic aryl groups, or both monocyclic aryl groups and multicyclic aryl groups. For example, the aryl group in the arylamine group may be selected from among the examples of the aryl group described above. Specific examples of the arylamine group may comprise phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, carbazole, a triphenylamine group and the like, but are not limited thereto.

In the present specification, examples of the heteroarylamine group comprise a substituted or unsubstituted monoheteroarylamine group, a substituted or unsubstituted diheteroarylamine group, or a substituted or unsubstituted triheteroarylamine group. The heteroarylamine group comprising two or more heteroaryl groups may comprise monocyclic heteroaryl groups, multicyclic heteroaryl groups, or both monocyclic heteroaryl groups and multicyclic heteroaryl groups. For example, the heteroaryl group in the heteroarylamine group may be selected from among the examples of the heteroaryl group described above.

In the present specification, an aromatic ring group may be monocyclic or multicyclic, and may be selected from among the examples of the aryl group except for being not monovalent.

In the present specification, the arylene group means an aryl group having two bonding sites, that is, a divalent group. Descriptions on the aryl group provided above may be applied thereto except for each being a divalent group.

In the present specification, the heteroarylene group means a heteroaryl group having two bonding sites, that is, a divalent group. Descriptions on the heteroaryl group provided above may be applied thereto except for each being a divalent group.

In one embodiment of the present specification, Chemical Formula 1 may be represented by the following Chemical Formulae 2 to 4.

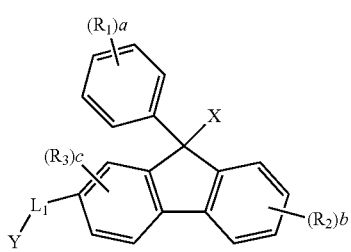

[Chemical Formula 2]

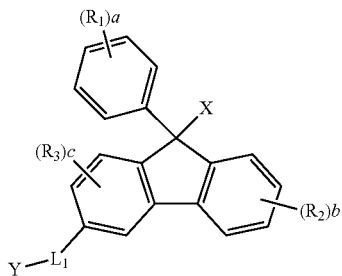

[Chemical Formula 3]

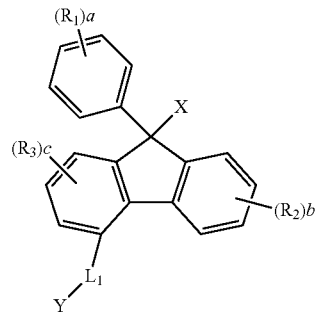

[Chemical Formula 4]

In Chemical Formulae 2 to 4,
definitions of X, Y, $L_1$, R, $R_1$ to $R_3$ and a to c are the same as in Chemical Formula 1.

According to one embodiment of the present specification, X is a substituted phenyl group; a substituted or unsubstituted dicyclic or higher aryl group; or a substituted or unsubstituted heterocyclic group.

According to one embodiment of the present specification, X is a substituted phenyl group; a substituted or unsubstituted dicyclic or higher aryl group having 10 to 24 carbon atoms; or a substituted or unsubstituted heterocyclic group having 2 to 50 carbon atoms.

According to one embodiment of the present specification, X is a substituted phenyl group, a substituted or unsubstituted naphthyl group, a substituted or unsubstituted phenanthryl group, a substituted or unsubstituted biphenyl group, a substituted or unsubstituted terphenyl group, a substituted or unsubstituted anthracenyl group, a substituted or unsubstituted triphenylene group, a substituted or unsubstituted pyrene group, a substituted or unsubstituted fluorenyl group, a substituted or unsubstituted pyridine group, or a substituted or unsubstituted isoquinoline group.

According to one embodiment of the present specification, X is a substituted phenyl group, a substituted or unsubstituted naphthyl group, a substituted or unsubstituted phenanthryl group, a substituted or unsubstituted biphenyl group, a substituted or unsubstituted terphenyl group, a substituted or unsubstituted anthracenyl group, a substituted or unsubstituted triphenylene group, a substituted or unsubstituted pyrene group, or a substituted or unsubstituted fluorenyl group.

According to one embodiment of the present specification, X is a phenyl group substituted with a halogen group, a substituted or unsubstituted alkoxy group, a substituted or unsubstituted alkyl group, a substituted or unsubstituted aryl group, or a substituted or unsubstituted heterocyclic group; a phenanthryl group unsubstituted or substituted with a halogen group, a substituted or unsubstituted alkoxy group, a substituted or unsubstituted alkyl group, a substituted or unsubstituted aryl group, or a substituted or unsubstituted heterocyclic group; a biphenyl group unsubstituted or substituted with a halogen group, a substituted or unsubstituted alkoxy group, a substituted or unsubstituted alkyl group, a substituted or unsubstituted aryl group, or a substituted or unsubstituted heterocyclic group; a terphenyl group unsubstituted or substituted with a halogen group, a substituted or unsubstituted alkoxy group, a substituted or unsubstituted alkyl group, a substituted or unsubstituted aryl group, or a substituted or unsubstituted heterocyclic group; an anthracenyl group unsubstituted or substituted with a halogen group, a substituted or unsubstituted alkoxy group, a substituted or unsubstituted alkyl group, a substituted or unsubstituted aryl group, or a substituted or unsubstituted heterocyclic group; a triphenylene group unsubstituted or substituted with a halogen group, a substituted or unsubstituted alkoxy group, a substituted or unsubstituted alkyl group, a substituted or unsubstituted aryl group, or a substituted or unsubstituted heterocyclic group; a pyrene group unsubstituted or substituted with a halogen group, a substituted or unsubstituted alkoxy group, a substituted or unsubstituted alkyl group, a substituted or unsubstituted aryl group, or a substituted or unsubstituted heterocyclic group; or a fluorenyl group unsubstituted or substituted with a halogen group, a substituted or unsubstituted alkoxy group, a substituted or unsubstituted alkyl group, a substituted or unsubstituted aryl group, or a substituted or unsubstituted heterocyclic group.

According to one embodiment of the present specification, X is a phenyl group substituted with a halogen group, a substituted or unsubstituted alkoxy group, a substituted or unsubstituted alkyl group, a substituted or unsubstituted aryl group, or a substituted or unsubstituted heterocyclic group; a phenanthryl group; a biphenyl group; a terphenyl group; a substituted or unsubstituted anthracenyl group; a triphenylene group; a pyrene group; or a fluorenyl group unsubstituted or substituted with an alkyl group.

According to one embodiment of the present specification, X is a phenyl group substituted with one or more substituents selected from the group consisting of a halogen group, or an alkoxy group substituted with a halogen group.

According to one embodiment of the present specification, X is a phenyl group substituted with one or more substituents selected from the group consisting of a fluoro group, or an alkoxy group having 1 to 4 carbon atoms substituted with a fluoro group.

According to one embodiment of the present specification, X is a phenyl group substituted with a fluoro group, or a fluoromethoxy group.

According to one embodiment of the present specification, X is a phenyl group substituted with a fluoro group.

According to one embodiment of the present specification, X is an anthracenyl group unsubstituted or substituted with an aryl group.

According to one embodiment of the present specification, X is an anthracenyl group unsubstituted or substituted with an aryl group having 6 to 12 carbon atoms.

According to one embodiment of the present specification, X is an anthracenyl group unsubstituted or substituted with a phenyl group or a naphthyl group.

According to one embodiment of the present specification, X is an anthracenyl group substituted with a phenyl group or a naphthyl group.

According to one embodiment of the present specification, X is a fluorenyl group unsubstituted or substituted with an alkyl group.

According to one embodiment of the present specification, X is a fluorenyl group unsubstituted or substituted with an alkyl group having 1 to 4 carbon atoms.

According to one embodiment of the present specification, X is a fluorenyl group unsubstituted or substituted with a methyl group.

According to one embodiment of the present specification, X is a fluorenyl group substituted with a methyl group.

According to one embodiment of the present specification, X is a phenyl group substituted with a fluoro group; a naphthyl group; a phenanthryl group; a biphenyl group; a terphenyl group; an anthracenyl group substituted with a phenyl group or a naphthyl group; a triphenylene group; a pyrene group; or a 9,9-dimethylfluorenyl group.

According to one embodiment of the present specification, X is a substituted or unsubstituted pyridine group, or a substituted or unsubstituted isoquinoline group.

According to one embodiment of the present specification, X is a pyridine group or an isoquinoline group.

According to one embodiment of the present specification, X may be any one selected from among the following structural formulae.

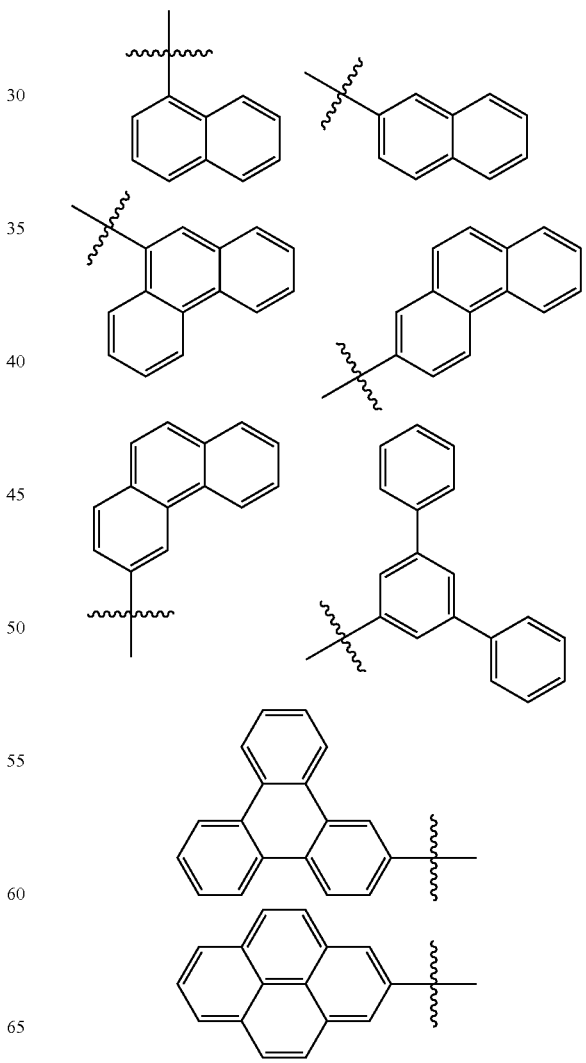

-continued

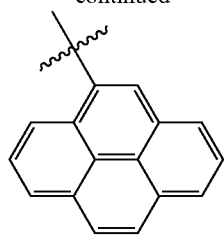

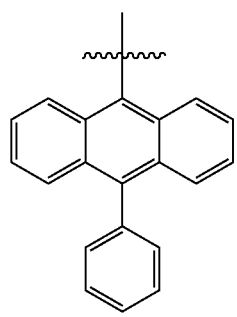

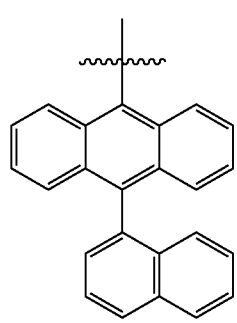

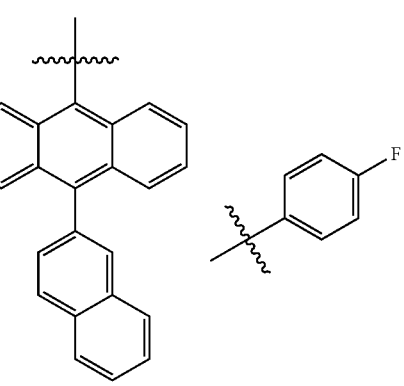

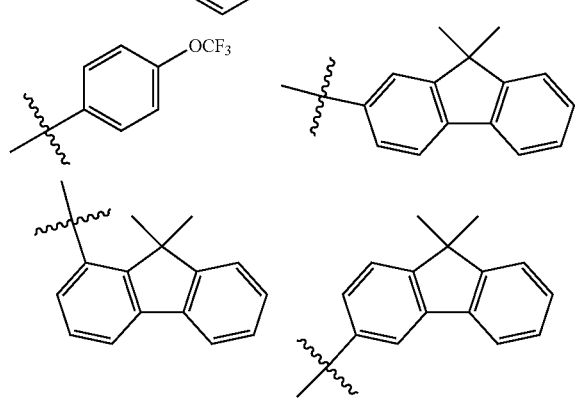

-continued

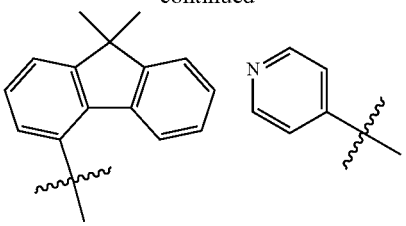

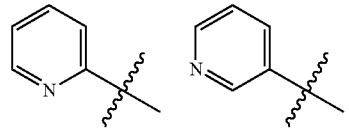

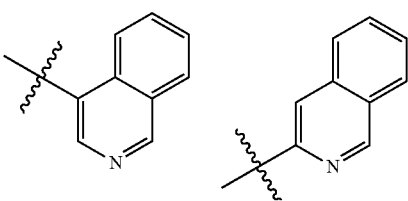

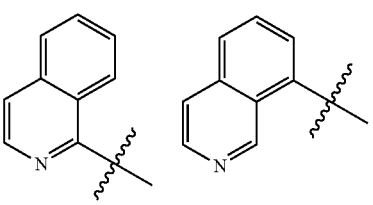

According to one embodiment of the present specification,

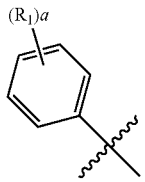

and X are different from each other.

According to one embodiment of the present specification, L₁ is a direct bond; a substituted or unsubstituted arylene group; or a substituted or unsubstituted heteroarylene group.

According to one embodiment of the present specification, L₁ is a direct bond; or a substituted or unsubstituted arylene group having 6 to 20 carbon atoms.

According to one embodiment of the present specification, L₁ is a direct bond; a substituted or unsubstituted phenylene group, a substituted or unsubstituted biphenylene group, or a substituted or unsubstituted naphthylene group.

According to one embodiment of the present specification, L₁ is a direct bond; or a phenylene group.

According to one embodiment of the present specification, Y is selected from among the following structural formulae.

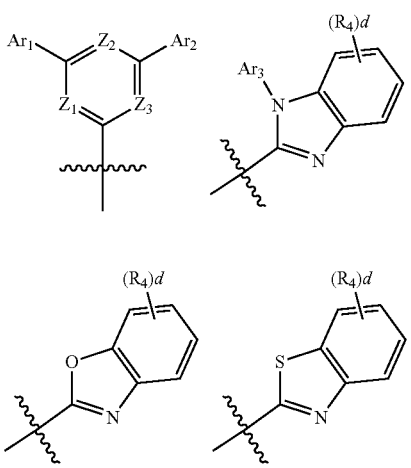

According to one embodiment of the present specification, two or more of $Z_1$ to $Z_3$ are N, and the rest are N or CR.

According to one embodiment of the present specification, $Ar_1$ to $Ar_3$ are the same as or different from each other, and each independently hydrogen; deuterium; a halogen group; a substituted or unsubstituted alkyl group; a substituted or unsubstituted cycloalkyl group; a substituted or unsubstituted phosphine oxide group; a substituted or unsubstituted aryl group; or a substituted or unsubstituted heteroaryl group.

According to one embodiment of the present specification, $Ar_1$ to $Ar_3$ are a substituted or unsubstituted aryl group having to 20 carbon atoms; or a substituted or unsubstituted heteroaryl group having 3 to 20 carbon atoms.

According to one embodiment of the present specification, $Ar_1$ to $Ar_3$ are the same as or different from each other, and each independently a substituted or unsubstituted phenyl group, a substituted or unsubstituted biphenyl group, or a substituted or unsubstituted naphthyl group.

According to one embodiment of the present specification, $Ar_1$ to $Ar_3$ are the same as or different from each other, and each independently a phenyl group, a biphenyl group or a naphthyl group.

According to one embodiment of the present specification, $Ar_1$ to $Ar_3$ are a phenyl group.

According to one embodiment of the present specification, R and $R_1$ to $R_4$ are the same as or different from each other, and each independently hydrogen; deuterium; a halogen group; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted alkenyl group; a substituted or unsubstituted silyl group; a substituted or unsubstituted boron group; a substituted or unsubstituted phosphine oxide group; a substituted or unsubstituted amine group; a substituted or unsubstituted arylamine group; a substituted or unsubstituted aryl group; or a substituted or unsubstituted heteroaryl group.

According to one embodiment of the present specification, R and $R_1$ to $R_4$ are hydrogen.

According to one embodiment of the present specification, $R_1$ is hydrogen.

According to one embodiment of the present specification, $Z_1$ to $Z_3$ are each N.

According to one embodiment of the present specification, $Z_1$ and $Z_2$ are each N, $Z_3$ is CR, and R is hydrogen.

According to one embodiment of the present specification, the compound of Chemical Formula 1 may be any one selected from among the following structural formulae.

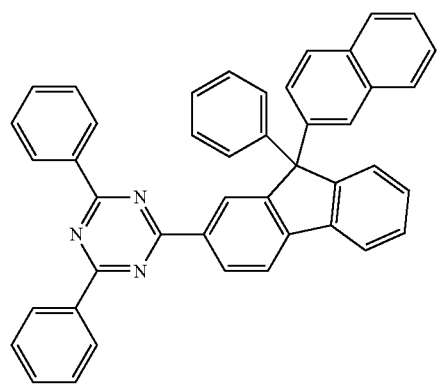

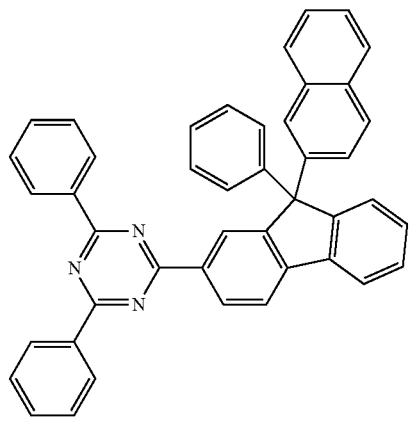

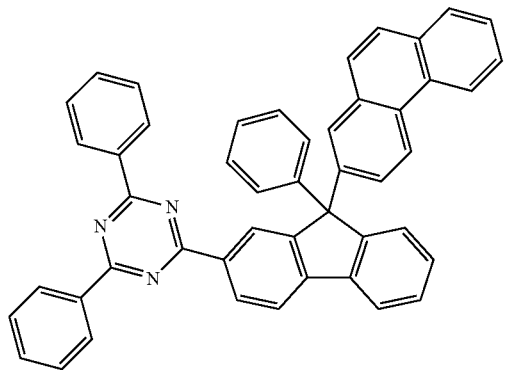

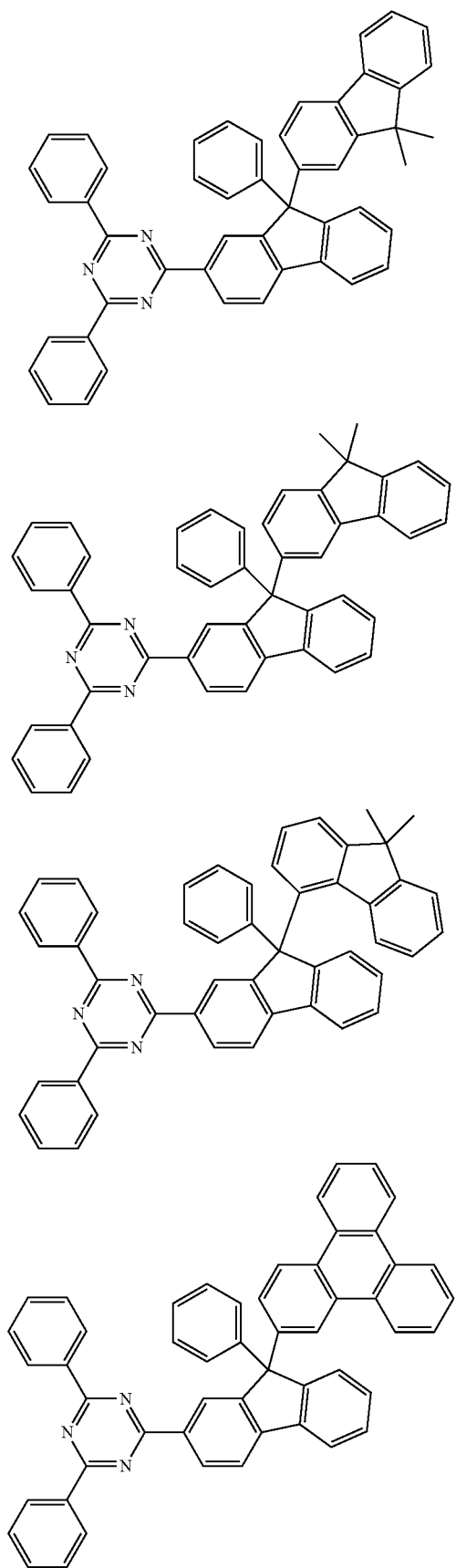
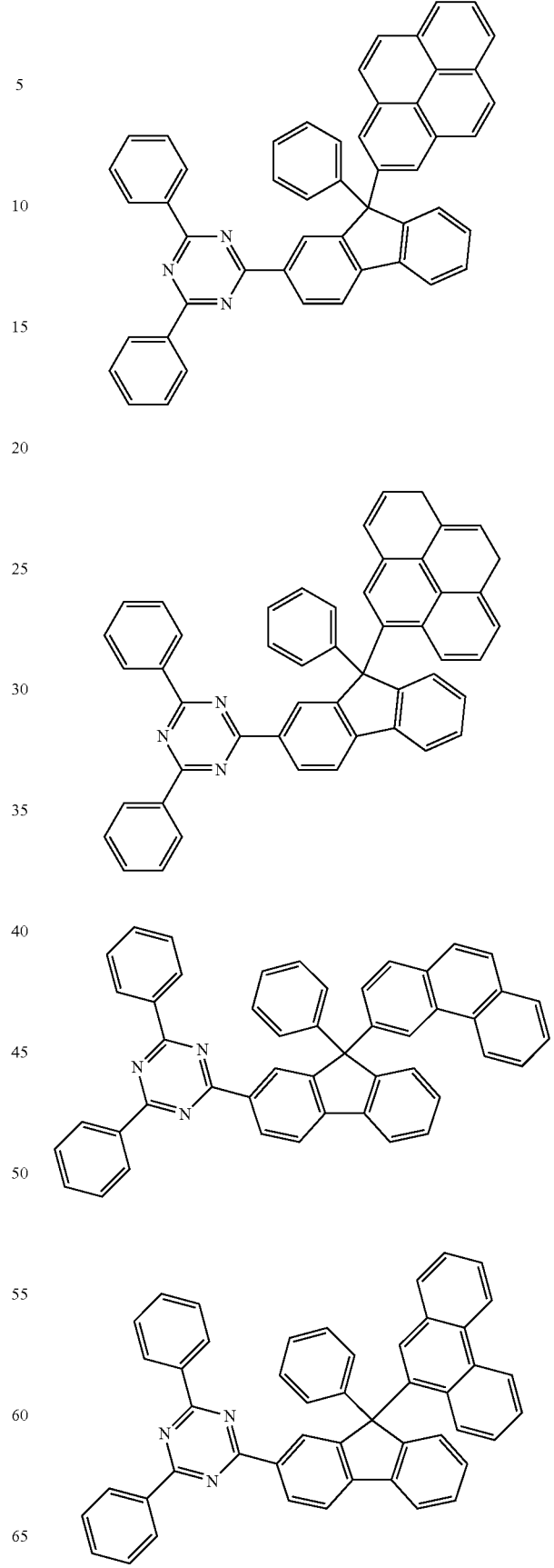

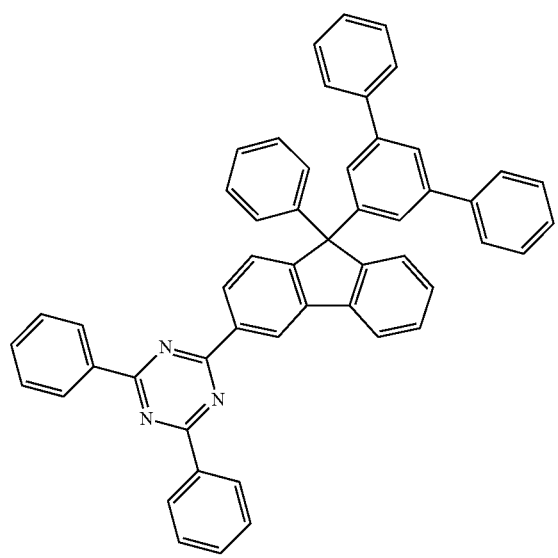
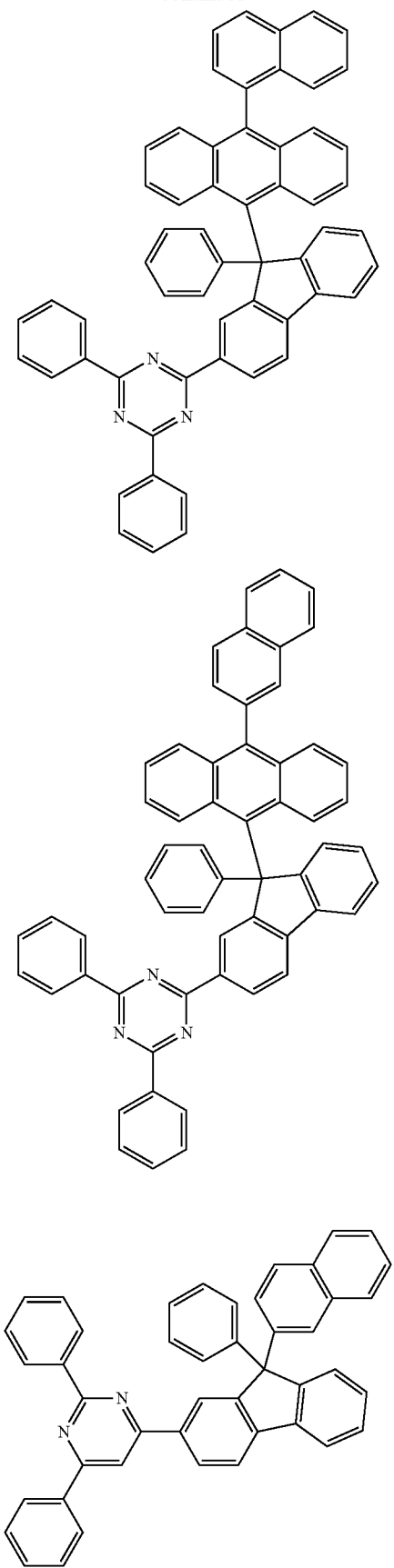

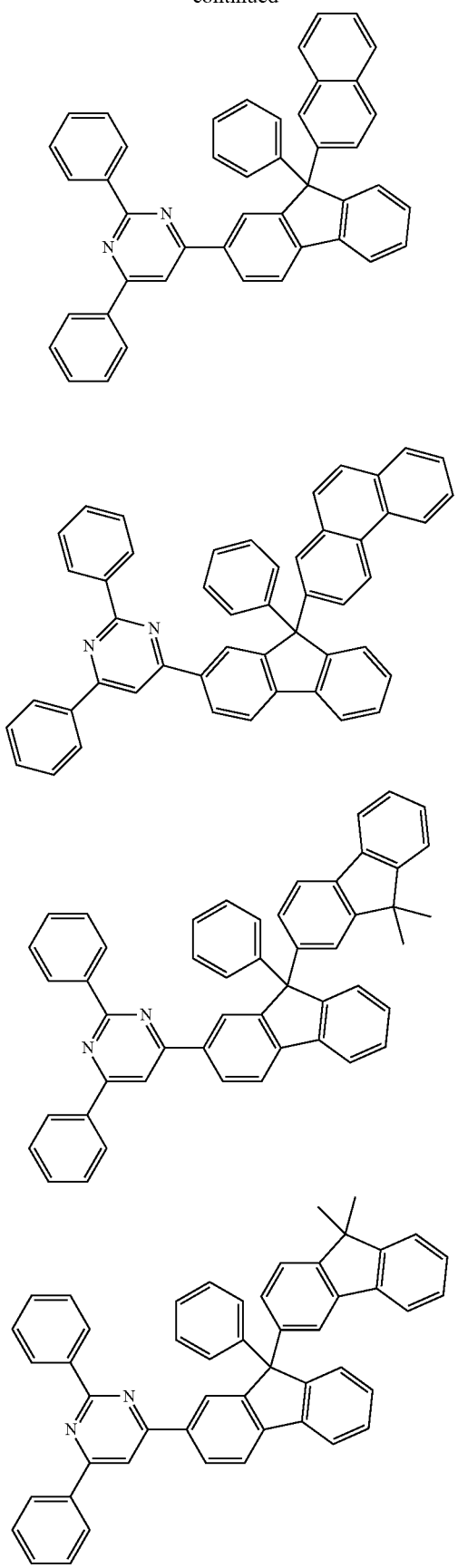
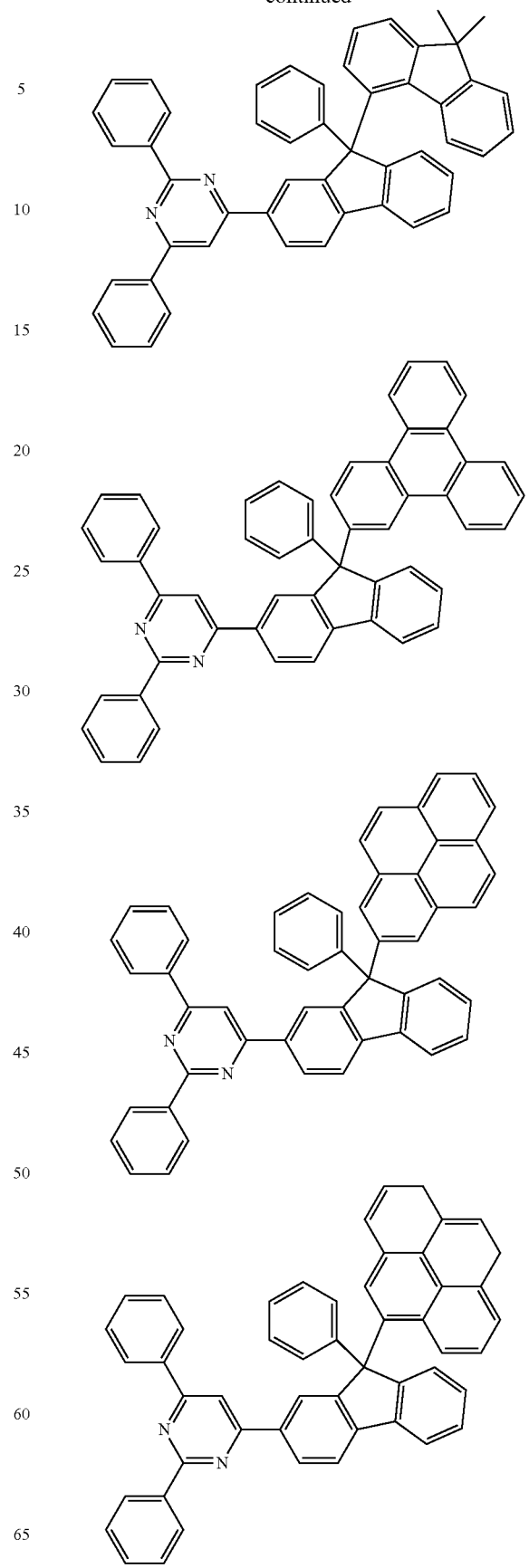

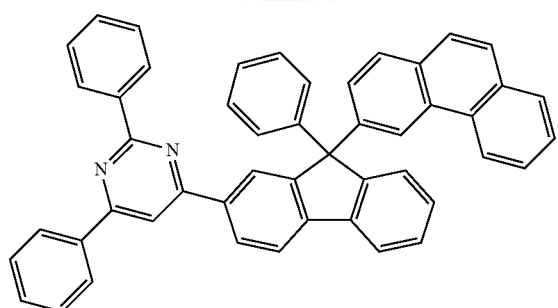
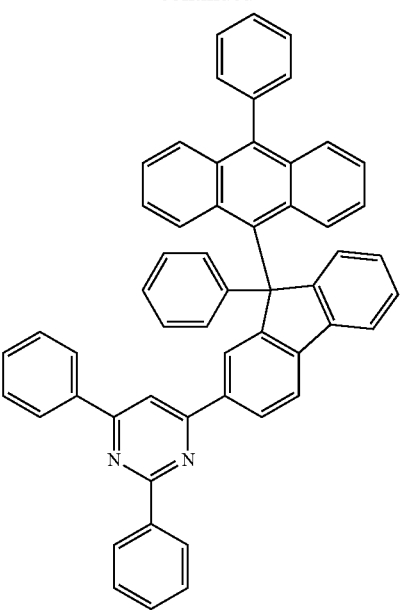
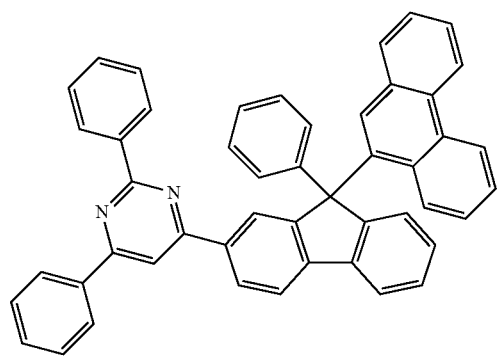
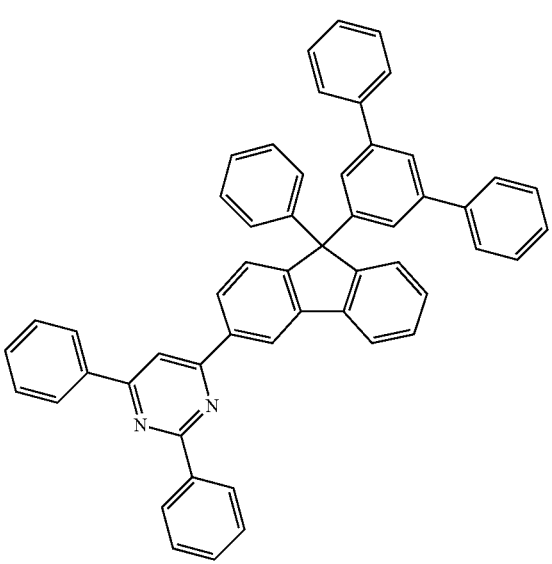
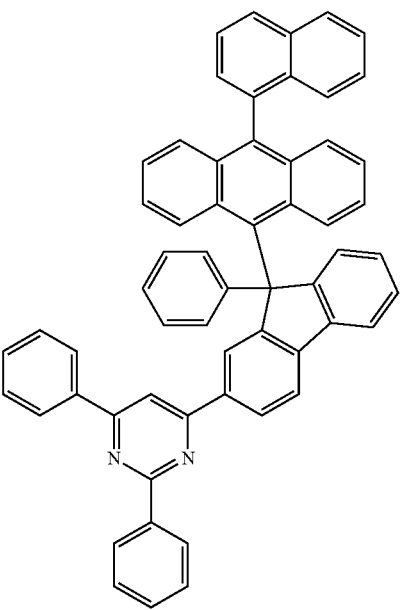

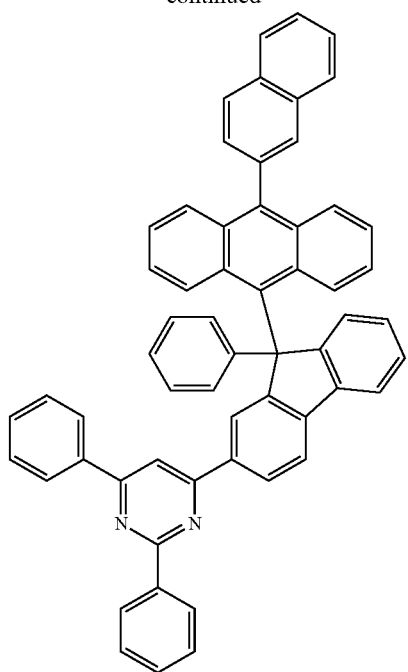
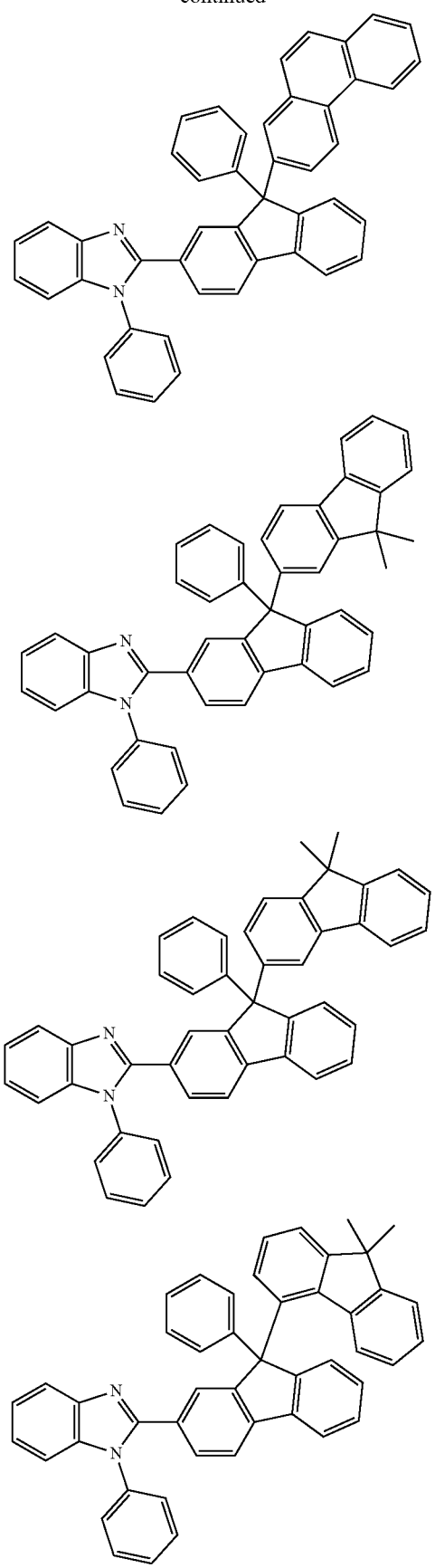

-continued
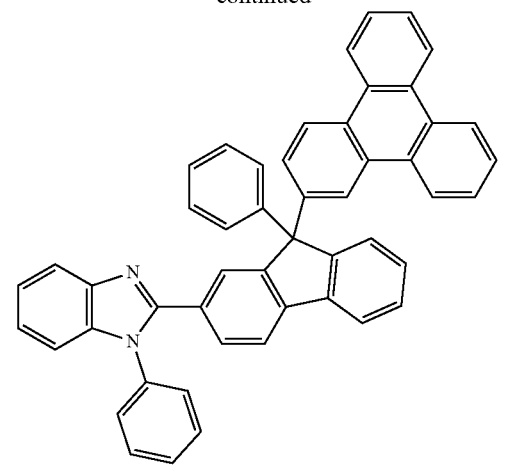
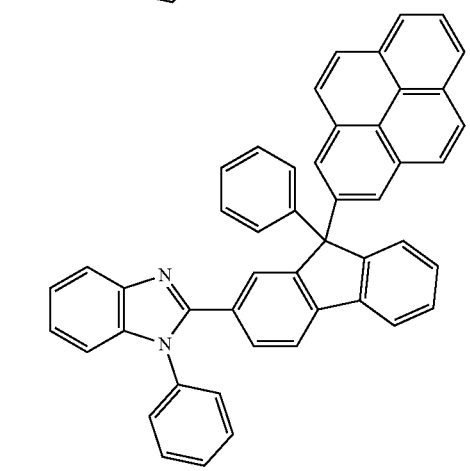
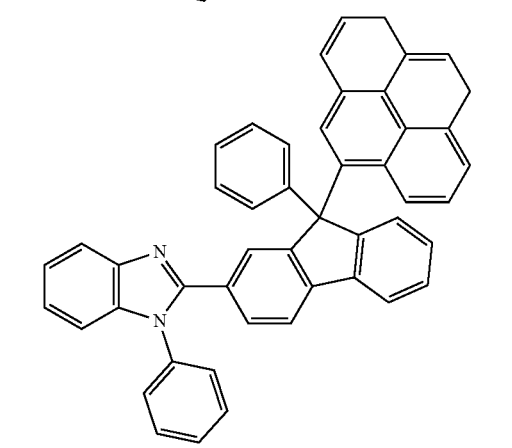
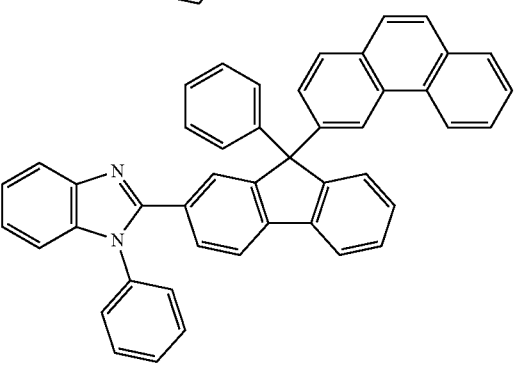
-continued
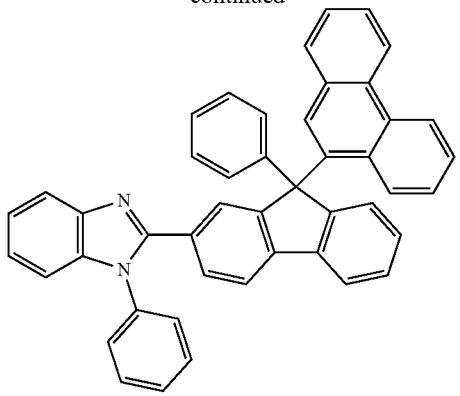
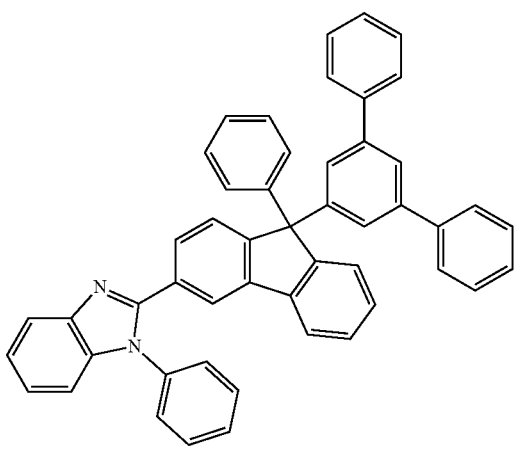
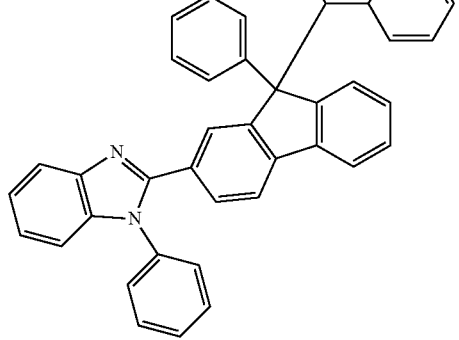

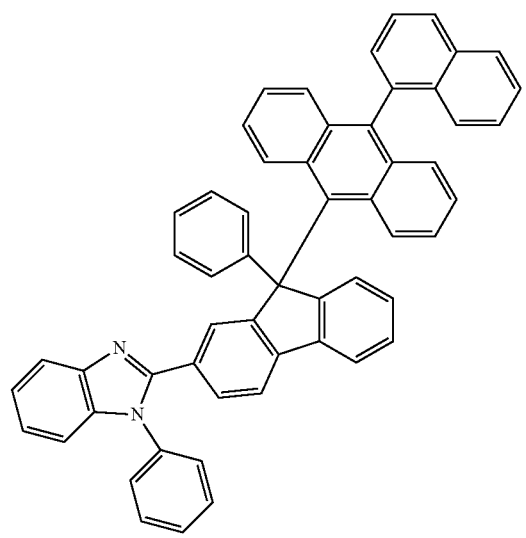
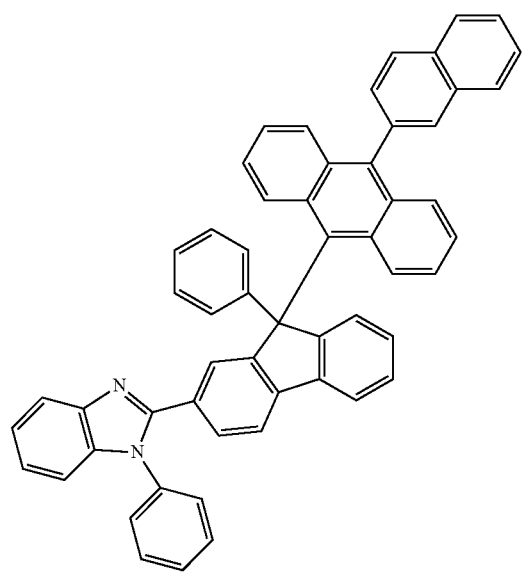
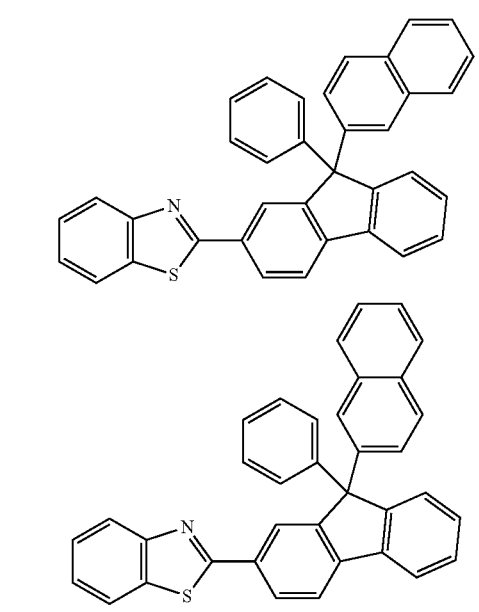
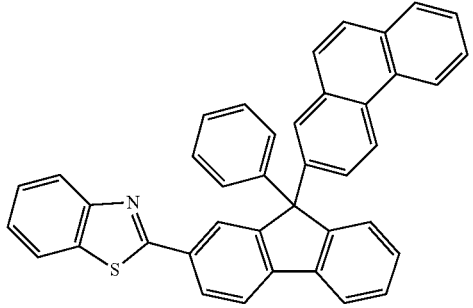
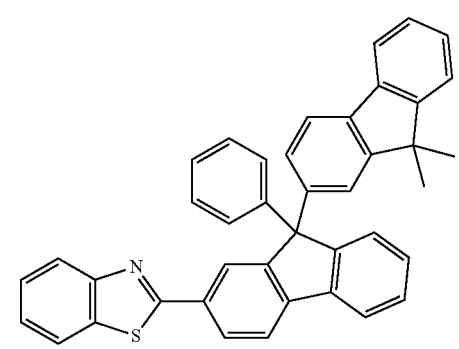
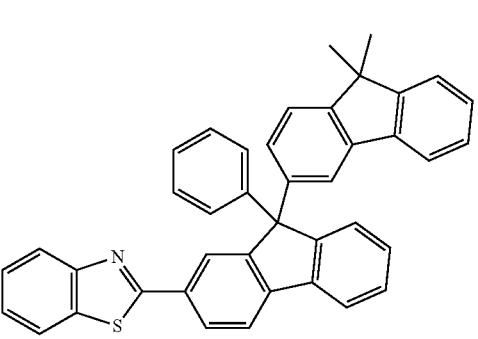
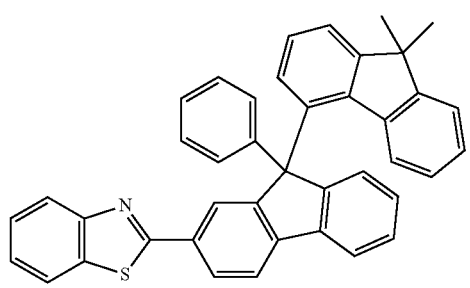
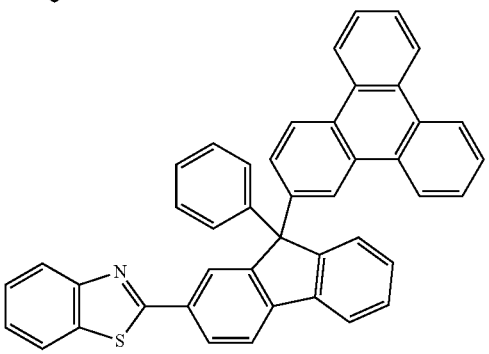

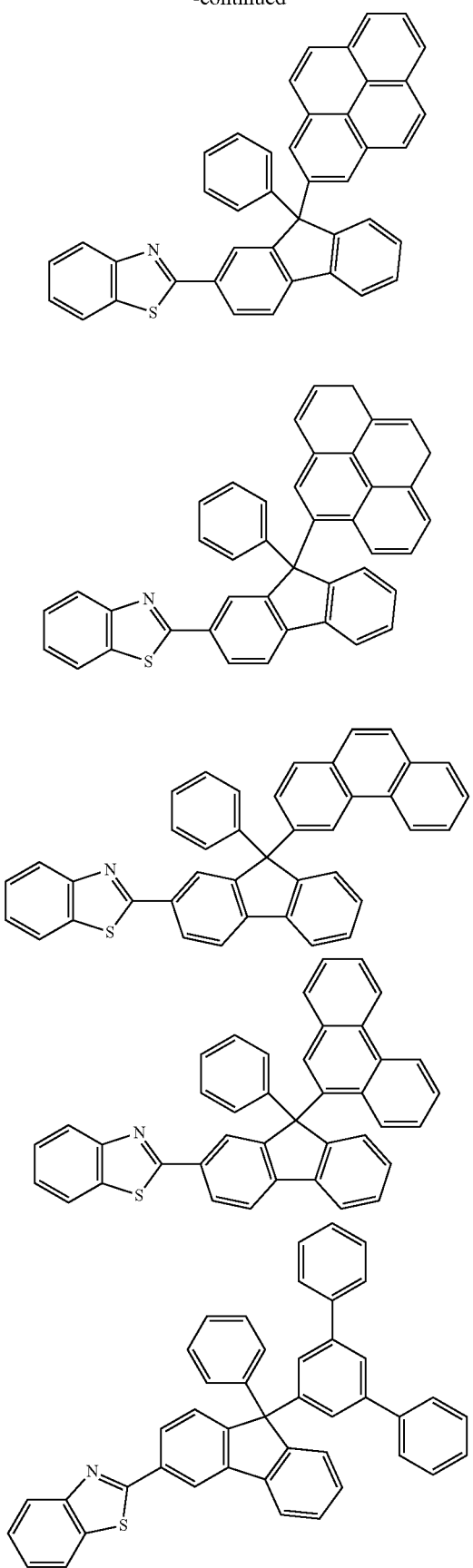
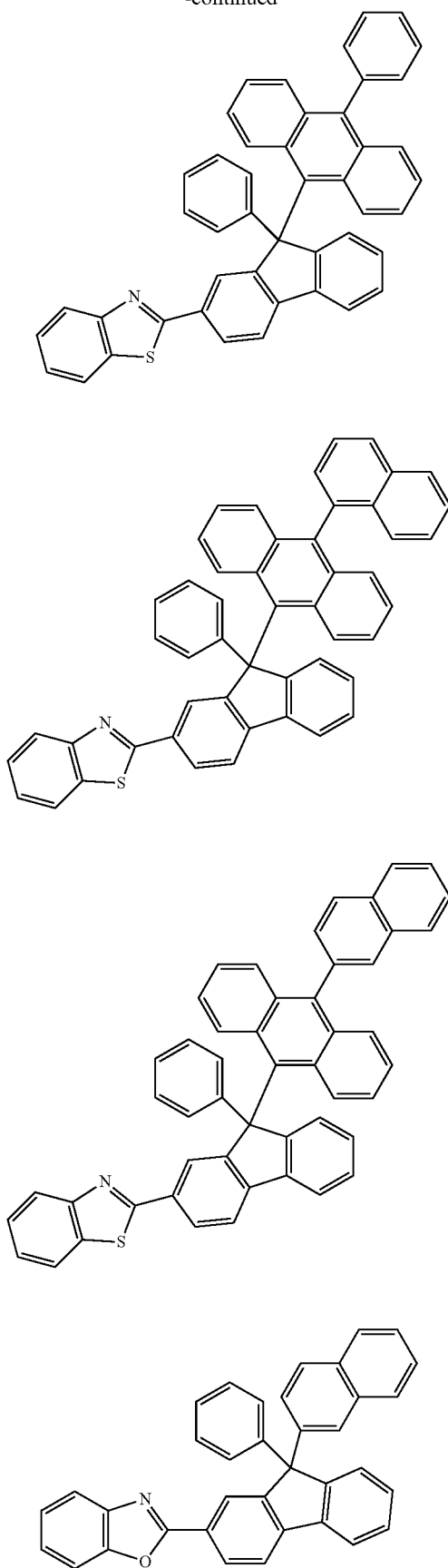

33
-continued
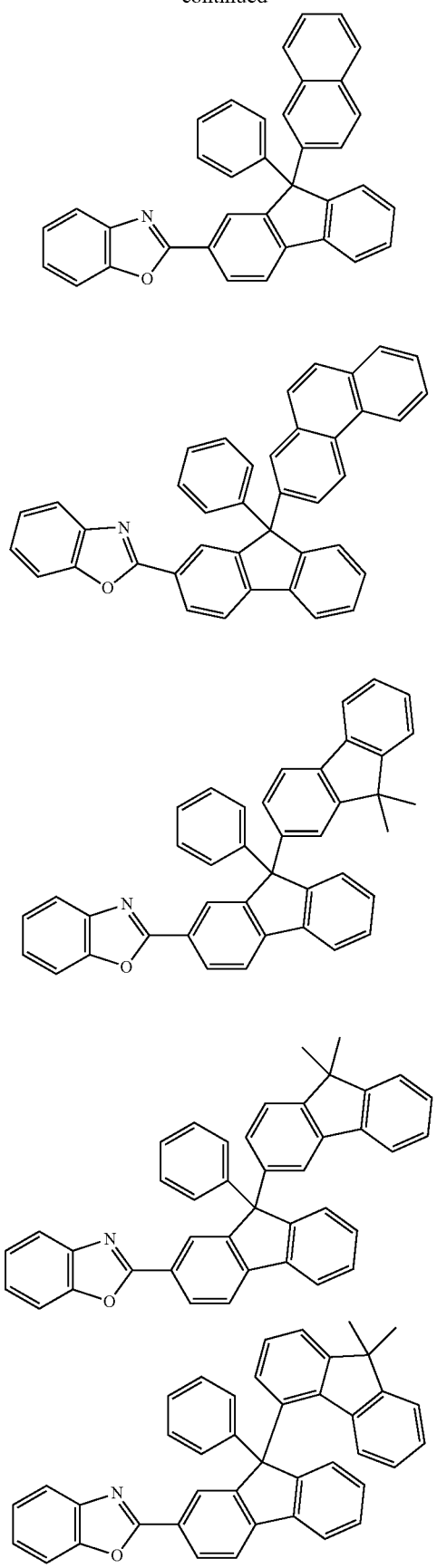
34
-continued
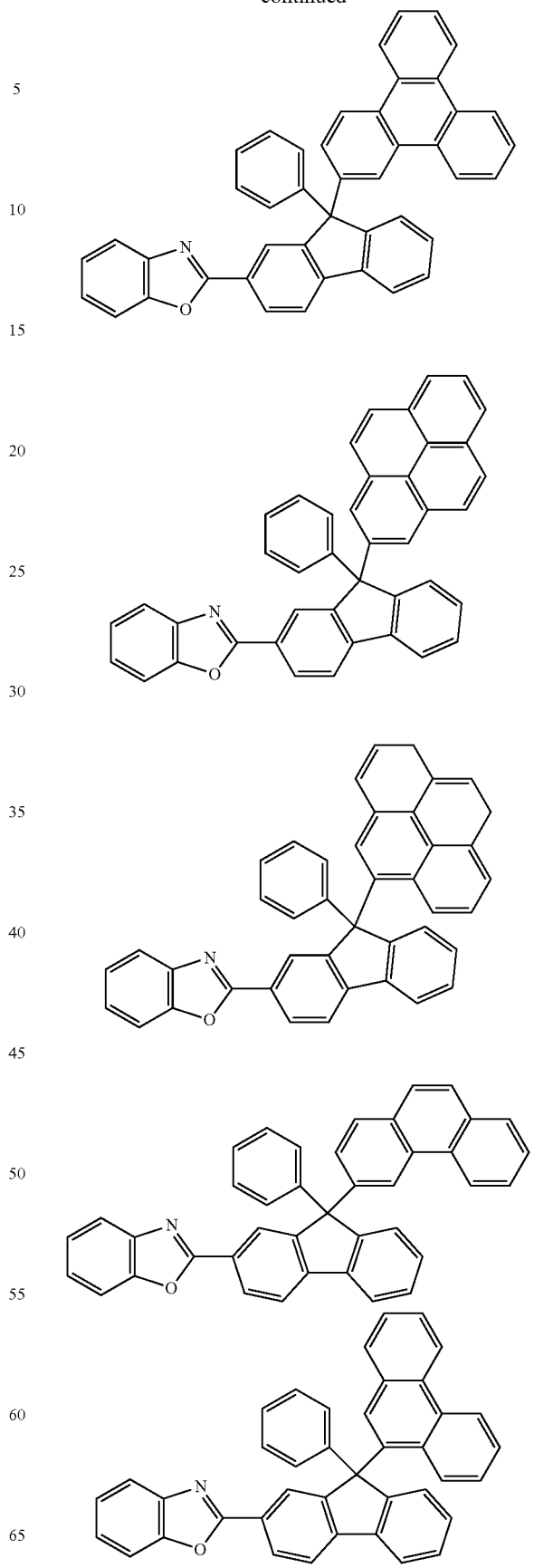

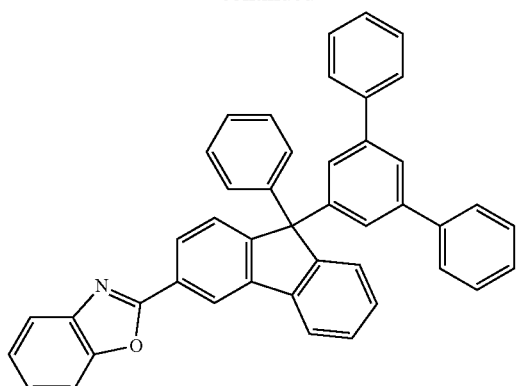
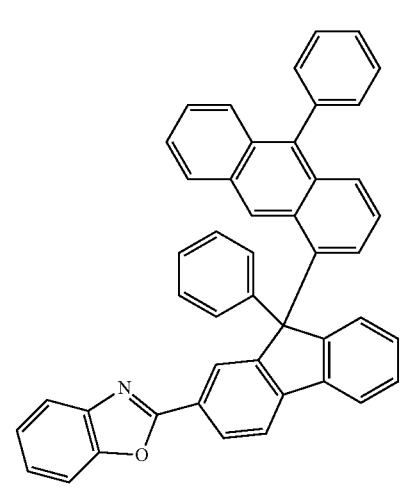
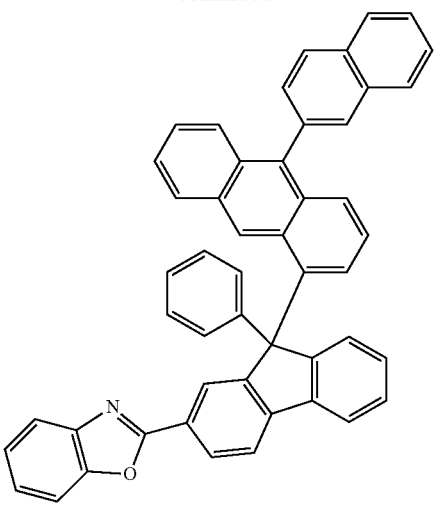
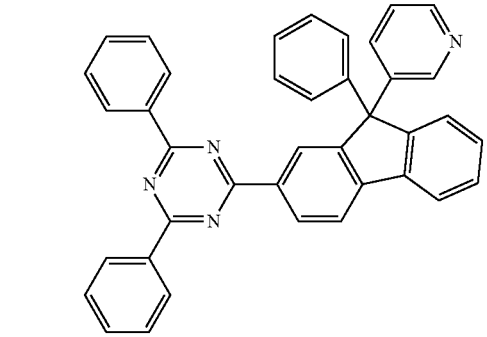
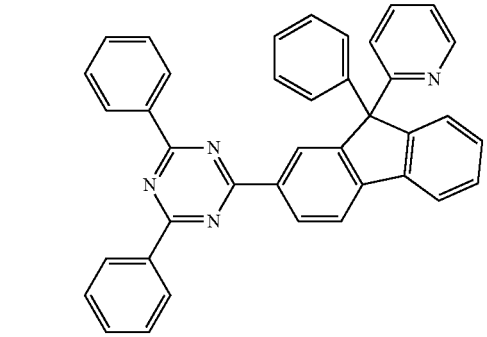
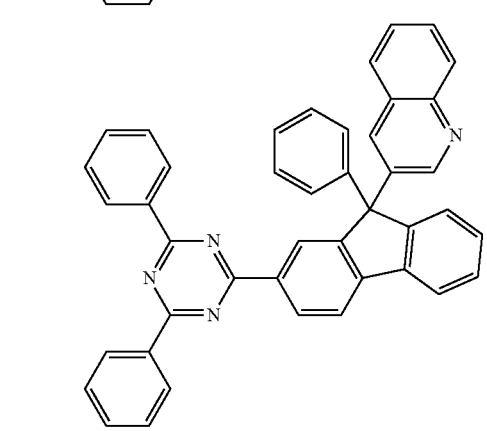

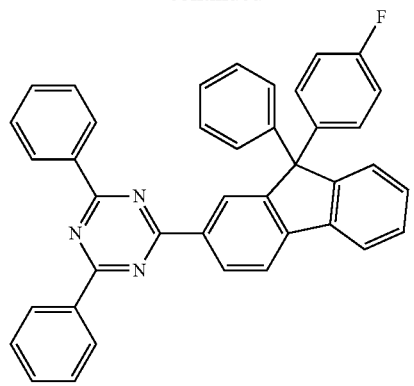
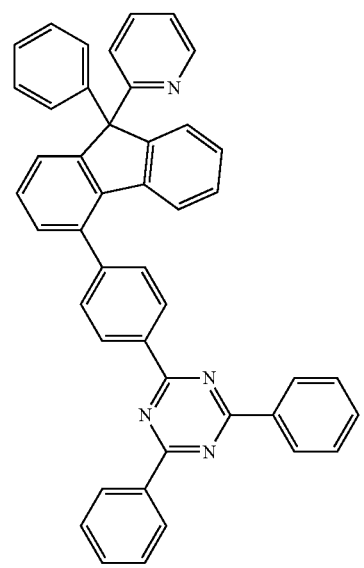
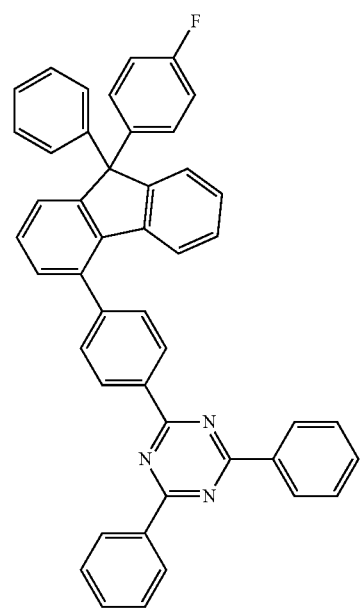
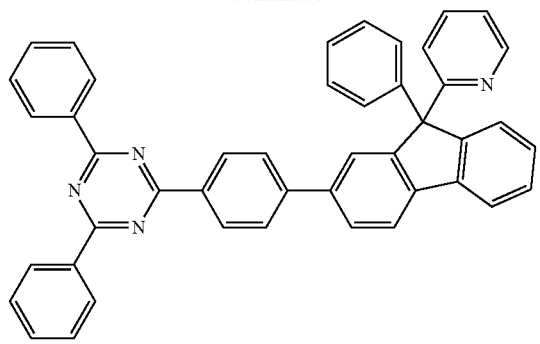
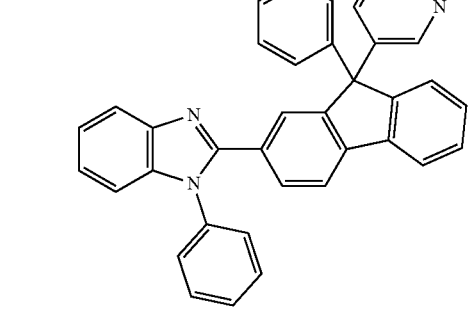
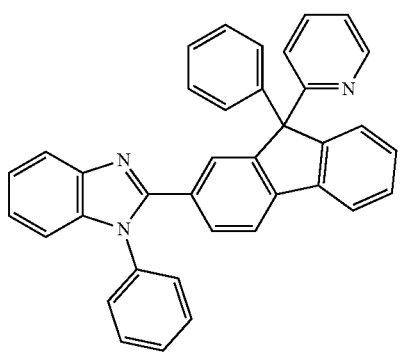
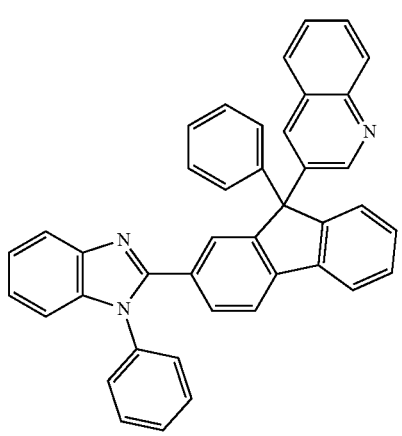

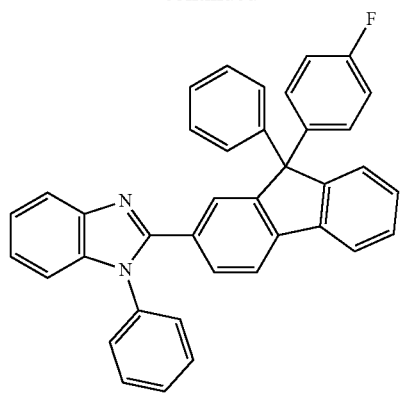
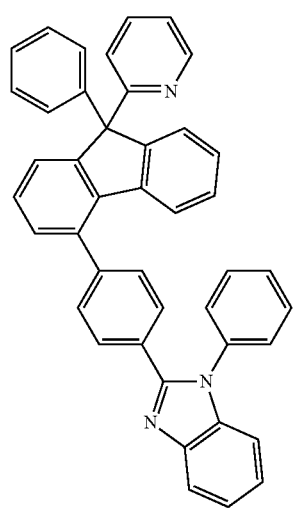
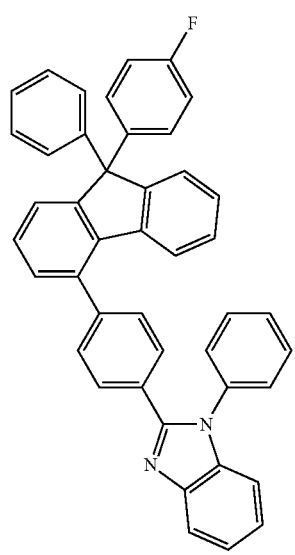
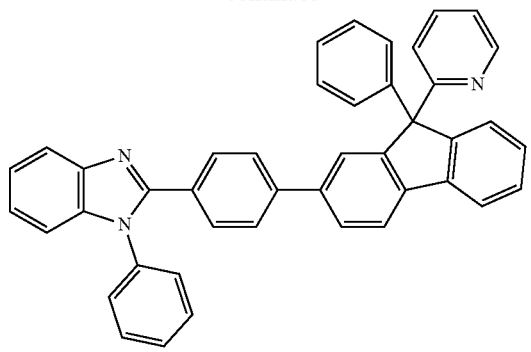
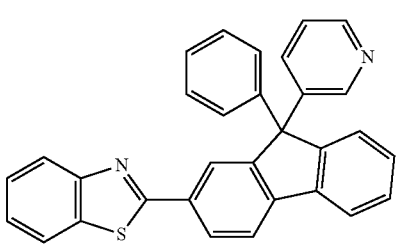
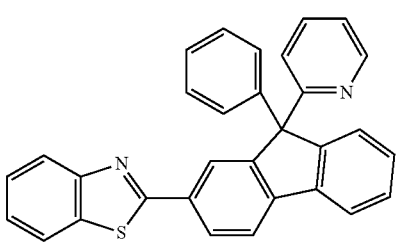
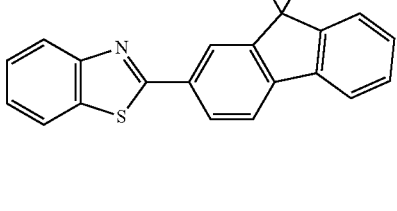
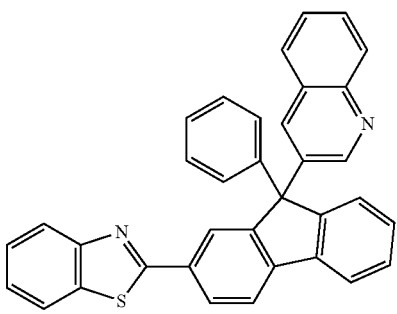
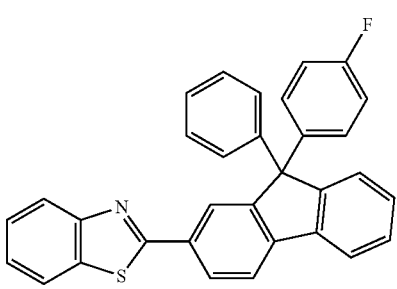

41
-continued
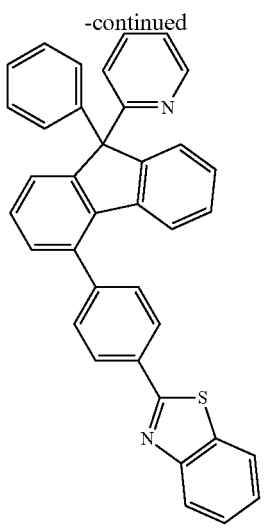
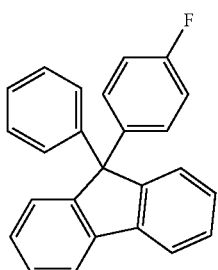
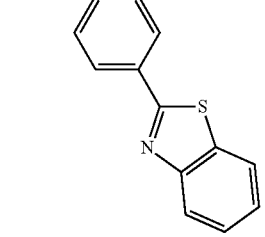
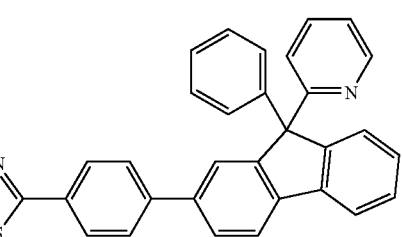
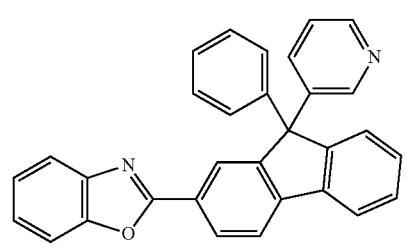
42
-continued
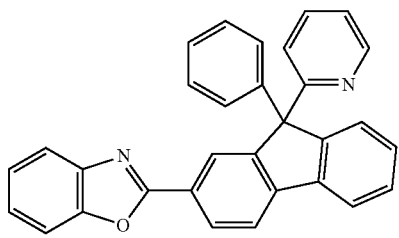
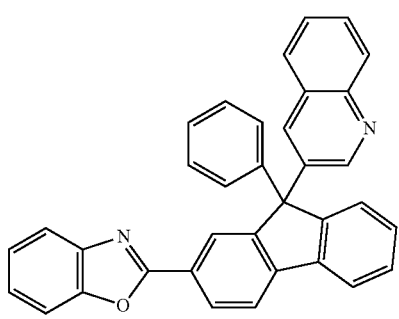
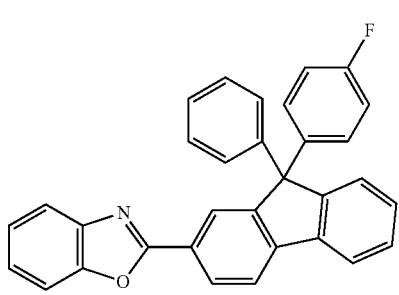
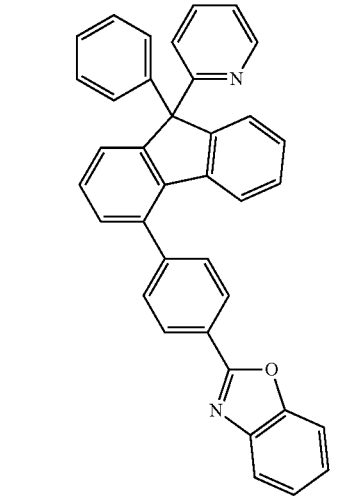

-continued

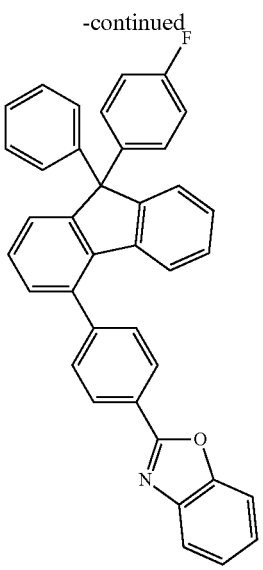

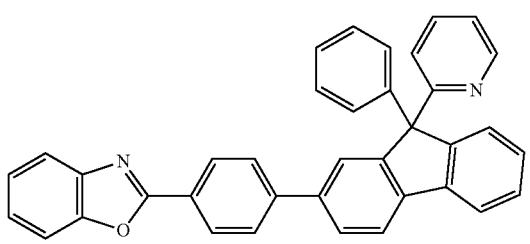 [SMILES: c1ccc(C2(c3ccccn3)c3ccccc3-c3ccc(-c4ccc(-c5nc6ccccc6o5)cc4)cc32)cc1]

The compounds according to one embodiment of the present specification may be prepared using preparation methods to be described below. In preparation examples described below, typical examples are described, however, as necessary, substituents may be added or excluded and positions of the substituents may be changed. In addition, starting materials, reaction materials, reaction conditions and the like may be changed depending on technologies known in the art.

In addition, the present specification provides an organic electronic device comprising the compound described above.

One embodiment of the present specification provides an organic electronic device comprising a first electrode; a second electrode provided opposite to the first electrode; and one or more organic material layers provided between the first electrode and the second electrode, wherein one or more layers of the organic material layers comprise the compound.

In the present specification, a description of one member being placed "on" another member comprises not only a case of the one member adjoining the another member but a case of still another member being present between the two members.

In the present specification, a description of a certain part "comprising" certain constituents means capable of further comprising other constituents, and does not exclude other constituents unless particularly stated on the contrary.

The organic material layer of the organic electronic device of the present specification may be formed in a single layer structure, but may be formed in a multilayer structure in which two or more organic material layers are laminated. For example, as a typical example of the organic electronic device of the present disclosure, an organic light emitting device may have a structure comprising a hole injection layer, a hole transfer layer, a light emitting layer, an electron transfer layer, an electron injection layer and the like as the organic material layer. However, the structure of the organic electronic device is not limited thereto, and may comprise less numbers of organic material layers.

According to one embodiment of the present specification, the organic electronic device may be selected from the group consisting of an organic light emitting device, an organic phosphorescent device, an organic solar cell, an organic photo conductor (OPC) and an organic transistor.

Hereinafter, an organic light emitting device will be illustrated.

In one embodiment of the present specification, the organic material layer comprises a light emitting layer, and the light emitting layer comprises the compound.

In one embodiment of the present specification, the organic material layer comprises a hole injection layer or a hole transfer layer, and the hole injection layer or the hole transfer layer comprises the compound.

In one embodiment of the present specification, the organic material layer comprises an electron transfer layer or an electron injection layer, and the electron transfer layer or the electron injection layer comprises the compound.

In one embodiment of the present specification, the organic material layer comprises an electron blocking layer, and the electron blocking layer comprises the compound.

In one embodiment of the present specification, the organic light emitting device further comprises one, two or more layers selected from the group consisting of a hole injection layer, a hole transfer layer, a light emitting layer, an electron transfer layer, an electron injection layer, a hole blocking layer and an electron blocking layer.

In one embodiment of the present specification, the organic light emitting device comprises a first electrode; a second electrode provided opposite to the first electrode; a light emitting layer provided between the first electrode and the second electrode; and two or more organic material layers provided between the light emitting layer and the first electrode, or between the light emitting layer and the second electrode, wherein at least one of the two or more organic material layers comprises the compound.

In one embodiment of the present specification, as the two or more organic material layers, two or more may be selected from the group consisting of an electron transfer layer, an electron injection layer, a layer carrying out electron transfer and electron injection at the same time, and a hole blocking layer.

In one embodiment of the present specification, the organic material layer comprises two or more electron transfer layers, and at least one of the two or more electron transfer layers comprises the compound. Specifically, in one embodiment of the present specification, the compound may be included in one of the two or more electron transfer layers, or included in each of the two or more electron transfer layers.

In addition, in one embodiment of the present specification, when the compound is included in each of the two or more electron transfer layers, materials other than the compound may be the same as or different from each other.

In one embodiment of the present specification, the organic material layer further comprises a hole injection layer or a hole transfer layer comprising a compound that comprises an arylamino group, a carbazolyl group or a benzocarbazolyl group in addition to the organic material layer comprising the compound.

In another embodiment, the organic light emitting device may be an organic light emitting device having a structure in which an anode, one or more organic material layers and a cathode are consecutively laminated on a substrate (normal type).

When the organic material layer comprising the compound of Chemical Formula 1 is an electron transfer layer, the electron transfer layer may further comprise an n-type dopant. As the n-type dopant, those known in the art may be used, and for example, metals or metal complexes may be used. According to one example, the electron transfer layer comprising the compound of Chemical Formula 1 may further comprise LiQ.

In another embodiment, the organic light emitting device may be an organic light emitting device having a reverse structure in which a cathode, one or more organic material layers and an anode are consecutively laminated on a substrate (inverted type).

For example, the organic light emitting device of the present specification may have a structure as shown in FIG. 1 and FIG. 2, however, the structure is not limited thereto.

FIG. 1 illustrates a structure of an organic light emitting device (10) in which a first electrode (30), a light emitting layer (40) and a second electrode (50) are consecutively laminated on a substrate (20). FIG. 1 is an illustrative structure of the organic light emitting device according to one embodiment of the present specification, and the structure may further comprise other organic material layers.

FIG. 2 illustrates a structure of an organic light emitting device in which a first electrode (30), a hole injection layer (60), a hole transfer layer (70), an electron blocking layer (80), a light emitting layer (40), an electron transfer layer (90), an electron injection layer (100) and a second electrode (50) are consecutively laminated on a substrate (20). FIG. 2 is an illustrative structure according to one embodiment of the present specification, and the structure may further comprise other organic material layers.

The organic light emitting device of the present specification may be manufactured using materials and methods known in the art, except that one or more layers of the organic material layers comprise the compound of the present specification, that is, the above-mentioned compound.

When the organic light emitting device comprises a plurality of organic material layers, the organic material layers may be formed with materials the same as or different from each other.

The organic light emitting device of the present specification may be manufactured using materials and methods known in the art, except that one or more layers of the organic material layers comprise the above-mentioned compound, that is, the compound represented by Chemical Formula 1.

For example, the organic light emitting device of the present specification may be manufactured by consecutively laminating a first electrode, an organic material layer and a second electrode on a substrate. Herein, the organic light emitting device may be manufactured by forming an anode on a substrate by depositing a metal, a metal oxide having conductivity, or an alloy thereof using a physical vapor deposition (PVD) method such as sputtering or e-beam evaporation, and forming an organic material layer comprising a hole injection layer, a hole transfer layer, a light emitting layer and an electron transfer layer, and then depositing a material capable of being used as a cathode thereon. In addition to such a method, the organic light emitting device may also be manufactured by consecutively depositing a cathode material, an organic material layer and an anode material on a substrate.

In addition, the compound of Chemical Formula 1 may be formed to an organic material layer using a solution coating method as well as a vacuum deposition method when manufacturing the organic light emitting device. Herein, the solution coating method means spin coating, dip coating, doctor blading, inkjet printing, screen printing, a spray method, roll coating and the like, but is not limited thereto.

In addition to such as method, the organic light emitting device may also be manufactured by consecutively laminating a cathode material, an organic material layer and an anode material on a substrate (International Patent Application Laid-Open Publication No. 2003/012890). However, the manufacturing method is not limited thereto.

In one embodiment of the present specification, the first electrode is an anode, and the second electrode is a cathode.

In another embodiment, the first electrode is a cathode, and the second electrode is an anode.

As the anode material, materials having large work function are normally preferable so that hole injection to an organic material layer is smooth. Specific examples of the anode material capable of being used in the present disclosure comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as $ZnO:Al$ or $SnO_2:Sb$; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferable so that electron injection to an organic material layer is smooth. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition, has an excellent thin film forming ability. The highest occupied molecular orbital (HOMO) of the hole injection material is preferably in between the work function of an anode material and the HOMO of surrounding organic material layers. Specific examples of the hole injection material comprise metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suitable. Specific examples thereof comprise arylamine-based organic materials, conductive polymers, block copolymers having conjugated parts and non-conjugated parts together, and the like, but are not limited thereto.

The electron blocking layer is a layer capable of enhancing lifespan and efficiency of a device by preventing holes injected from a hole injection layer from passing through a light emitting layer and entering an electron injection layer, and as necessary, may be formed in an appropriate place between the light emitting layer and the electron injection layer using materials known in the art.

The light emitting material of the light emitting layer is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof comprise 8-hydroxyquinoline aluminum complexes ($Alq_3$); carbazole series compounds; dimerized styryl compounds; BAlq; 10-hydroxybenzo quinoline-metal compounds; benzoxazole, benzothiazole and benzimidazole series compounds; poly(p-phenylenevinylene) (PPV) series polymers; spiro compounds; polyfluorene, rubrene, and the like, but are not limited thereto.

The light emitting layer may comprise a host material and a dopant material. The host material comprises fused aromatic ring derivatives, heteroring-containing compounds or the like. Specifically, the fused aromatic ring derivative comprises anthracene derivatives, pyrene derivatives, naphthalene derivatives, pentacene derivatives, phenanthrene compounds, fluoranthene compounds and the like, and the heteroring-containing compound comprises dibenzofuran derivatives, ladder-type furan compounds, pyrimidine derivatives and the like, but the material is not limited thereto.

The dopant material comprises aromatic amine derivatives, styrylamine compounds, boron complexes, fluoranthene compounds, metal complexes and the like. Specifically, the aromatic amine derivative is a fused aromatic ring derivative having a substituted or unsubstituted arylamino group and comprises arylamino group-comprising pyrene, anthracene, chrysene, peryflanthene and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group are substituted or unsubstituted. Specifically, styrylamine, styryldiamine, styryltriamine, styryltetramine or the like is included, but the styrylamine compound is not limited thereto. In addition, the metal complex comprises iridium complexes, platinum complexes or the like, but is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suitable. Specific examples thereof comprise Al complexes of 8-hydroxyquinoline; complexes comprising $Alq_3$; organic radical compounds; hydroxyflavon-metal complexes, and the like, but are not limited thereto. The electron transfer layer may be used together with any desired cathode material as used in the art. Particularly, examples of the suitable cathode material comprise common materials that have small work function, and in which an aluminum layer or a silver layer follows. Specifically, the cathode material comprises cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition, has an excellent thin film forming ability. Specific examples thereof comprise fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The metal complex compound comprises 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato) aluminum, tris(8-hydroxyquinolinato) gallium, bis(10-hydroxybenzo[h]quinolinato)berylium, bis(10-hydroxybenzo[h]quinolinato) zinc, bis(2-methyl-8-quinolinato) chlorogallium, bis(2-methyl-8-quinolinato)(o-cresolato)gallium, bis(2-methyl-8-quinolinato)(1-naphtholato) aluminum, bis(2-methyl-8-quinolinato)(2-naphtholato) gallium and the like, but is not limited thereto.

The hole blocking layer is a layer blocking holes from reaching a cathode and generally, may be formed under the same condition as the hole injection layer. Specifically, oxadiazole derivatives, triazole derivatives, phenanthroline derivatives, BCP, aluminum complexes and the like are included, however, the hole blocking layer is not limited thereto.

The organic light emitting device according to the present specification may be a top-emission type, a bottom-emission type or a dual-emission type depending on the materials used.

In one embodiment of the present specification, the compound represented by Chemical Formula 1 may be included in an organic solar cell or an organic transistor in addition to the organic light emitting device.

The compound according to the present specification may also be used in an organic electronic device comprising an organic phosphorescent device, an organic solar cell, an organic photo conductor, an organic transistor and the like on a similar principle to that used in the organic light emitting device.

Hereinafter, the present specification will be described in detail with reference to examples. However, the examples according to the present specification may be modified to various other forms and the scope of the present specification is not to be construed as being limited to the examples described below. The examples of the present specification are provided in order to more fully describe the present specification to those having average knowledge in the art.

<Synthesis Example 1>—Preparation of Compound Represented by Intermediate 1

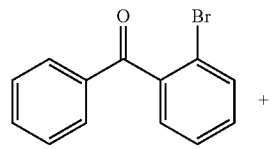

Molecular Weight: 261.12

[Compound 1A]

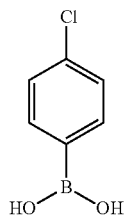

Molecular Weight: 156.37

[Compound 1B]

TTP, K₂CO₃
THF/H2O

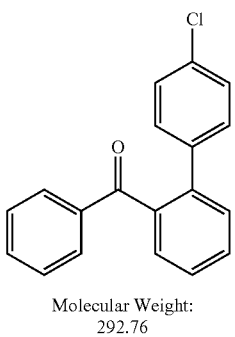

Molecular Weight: 292.76

[Intermediate 1]

<Synthesis Example 2>—Preparation of Compound Represented by Intermediate 2

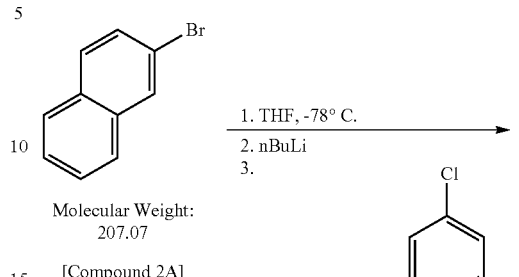

Molecular Weight: 207.07

[Compound 2A]

1. THF, -78° C.
2. nBuLi
3.

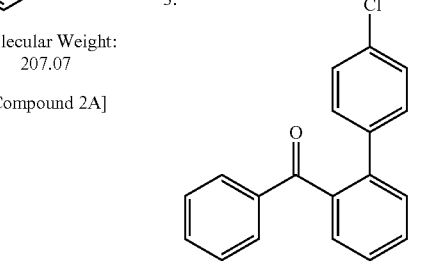

Molecular Weight: 292.76

[Intermediate 1]

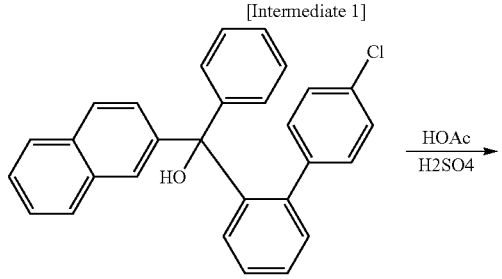

Molecular Weight: 420.94

[Compound 2B]

HOAc
H2SO4

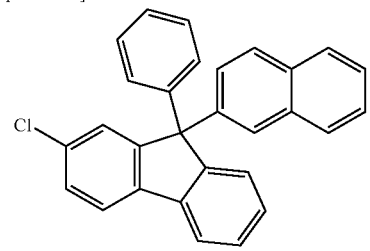

Molecular Weight: 402.92

[Intermediate 2]

Under nitrogen atmosphere, Compound 1A (50.0 g, 192 mmol) and Compound 1B (30 g, 191 mmol) were placed in 500 ml of tetrahydrofuran, and the mixture was stirred and refluxed. After that, potassium carbonate (79 g, 574 mmol) dissolved in 200 ml of water was introduced thereto and the result was sufficiently stirred, and then tetrakistriphenylphosphino palladium (6.6 g, 5.7 mmol) was introduced thereto. After reacting for 6 hours, the temperature was lowered to room temperature and the result was filtered. The filtrate was extracted using chloroform and water, and the organic layer was dried using magnesium sulfate. After that, the organic layer was vacuum distilled and purified using column chromatography. The purified material was dried to prepare Intermediate 1 (36 g, yield: 65%).

Compound 2A (10.0 g, 48 mmol) was placed in 100 ml of anhydrous tetrahydrofuran, and the result was cooled to −78° C. After that, n-butyllithium (2.5 M in hexane) (29 mL, 72 mmol) was slowly added dropwise thereto over 30 minutes while stirring, and the result was reacted for 1 hour. Then, Intermediate 1 (14 g, 48 mmol) was introduced thereto in a solid state, the temperature was slowly raised to room temperature, and the result was reacted for 4 hours. After the reaction, water was poured thereinto to terminate the reaction, the water layer and the organic layer were separated, and the organic layer was vacuum distilled to obtain Compound 2B. This was placed in 100 ml of acetic acid again, and then the result was refluxed after introducing 1 to 2 drops of sulfuric acid thereto as a catalyst while stirring. After reacting for 2 hours, the produced solids were filtered, the filtrate was dissolved in chloroform again, and then neutralized and extracted using water saturated with calcium carbonate, and the organic layer was dried using magnesium sulfate. After that, the organic layer was vacuum distilled and recrystallized using ethanol. The produced solids were filtered and dried to prepare Intermediate 2 (14 g, yield: 70%).

<Synthesis Example 3>—Preparation of Compound Represented by Intermediate 3

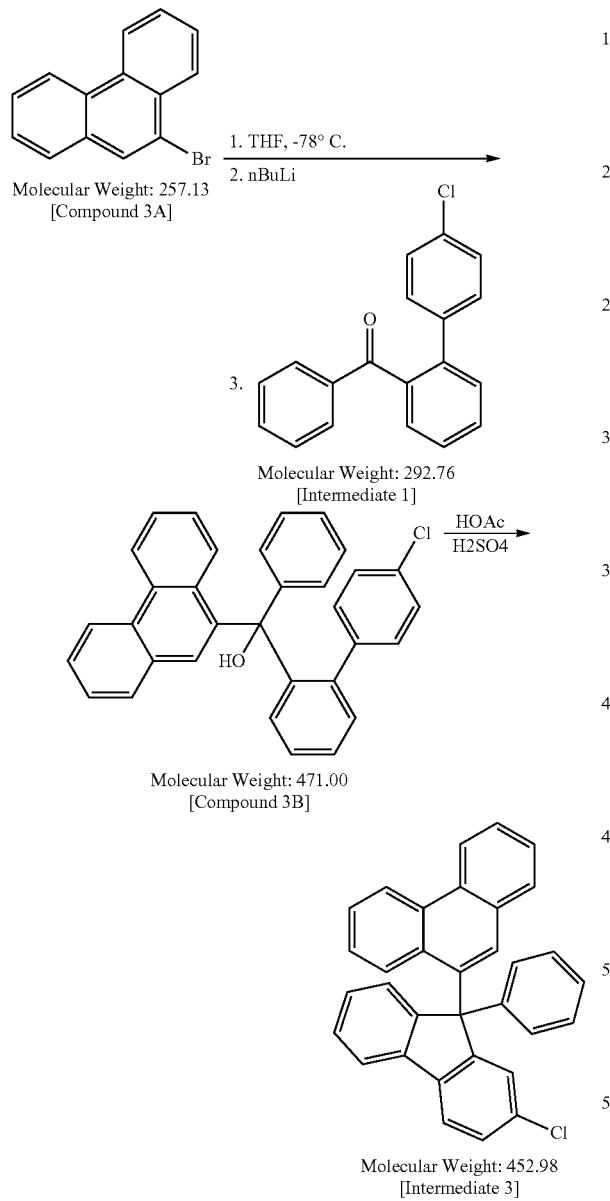

Compound 3A (10.0 g, 39 mmol) was placed in 100 ml of anhydrous tetrahydrofuran, and the result was cooled to −78° C. After that, n-butyllithium (2.5 M in hexane) (23 mL, 58 mmol) was slowly added dropwise thereto over 30 minutes while stirring, and the result was reacted for 1 hour. Then, Intermediate 1 (11 g, 39 mmol) was introduced thereto in a solid state, the temperature was slowly raised to room temperature, and the result was reacted for 4 hours. After the reaction, water was poured thereinto to terminate the reaction, the water layer and the organic layer were separated, and the organic layer was vacuum distilled to obtain Compound 3B. This was placed in 100 ml of acetic acid again, and then the result was refluxed after introducing 1 to 2 drops of sulfuric acid thereto as a catalyst while stirring. After reacting for 2 hours, the produced solids were filtered, the filtrate was dissolved in chloroform again, and then neutralized and extracted using water saturated with calcium carbonate, and the organic layer was dried using magnesium sulfate. After that, the organic layer was vacuum distilled and recrystallized using ethanol. The produced solids were filtered and dried to prepare Intermediate 3 (14 g, yield: 77%).

<Synthesis Example 4>—Preparation of Compound Represented by Intermediate 4

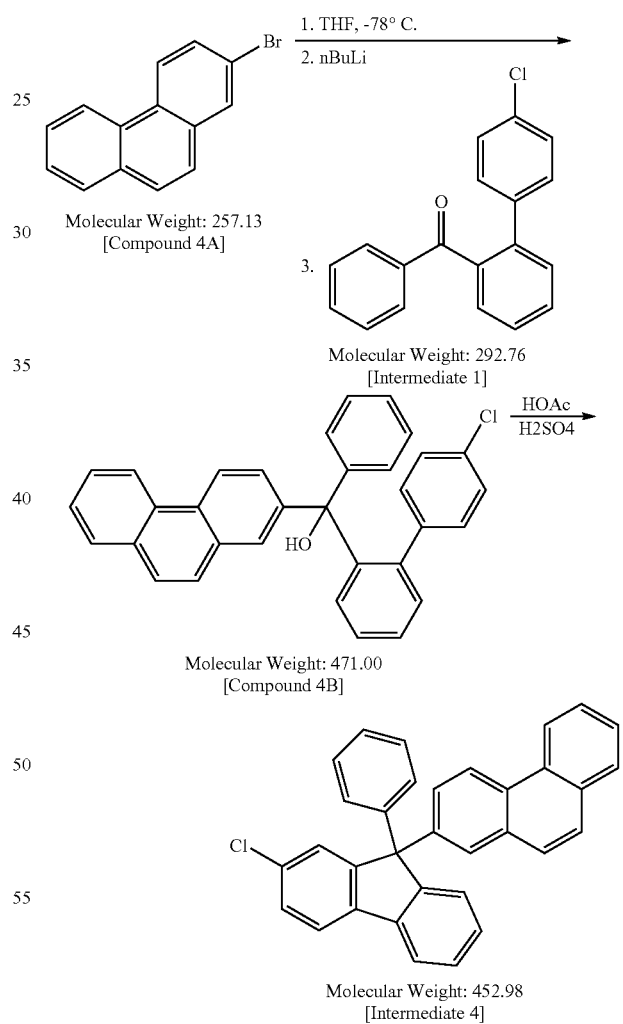

Compound 4A (10.0 g, 39 mmol) was placed in 100 ml of anhydrous tetrahydrofuran, and the result was cooled to −78° C. After that, n-butyllithium (2.5 M in hexane) (23 mL, 58 mmol) was slowly added dropwise thereto over 30 minutes while stirring, and the result was reacted for 1 hour. Then, Intermediate 1 (11 g, 39 mmol) was introduced thereto in a solid state, the temperature was slowly raised to room temperature, and the result was reacted for 4 hours. After the reaction, water was poured thereinto to terminate the reaction, the water layer and the organic layer were separated, and the organic layer was vacuum distilled to obtain Compound 4B. This was placed in 100 ml of acetic acid again, and then the result was refluxed after introducing 1 to 2 drops of sulfuric acid thereto as a catalyst while stirring. After reacting for 2 hours, the produced solids were filtered, the filtrate was dissolved in chloroform again, and then neutralized and extracted using water saturated with calcium carbonate, and the organic layer was dried using magnesium sulfate. After that, the organic layer was vacuum distilled and recrystallized using ethanol. The produced solids were filtered and dried to prepare Intermediate 4 (14 g, yield: 80%).

<Synthesis Example 5>—Preparation of Compound Represented by Intermediate 5

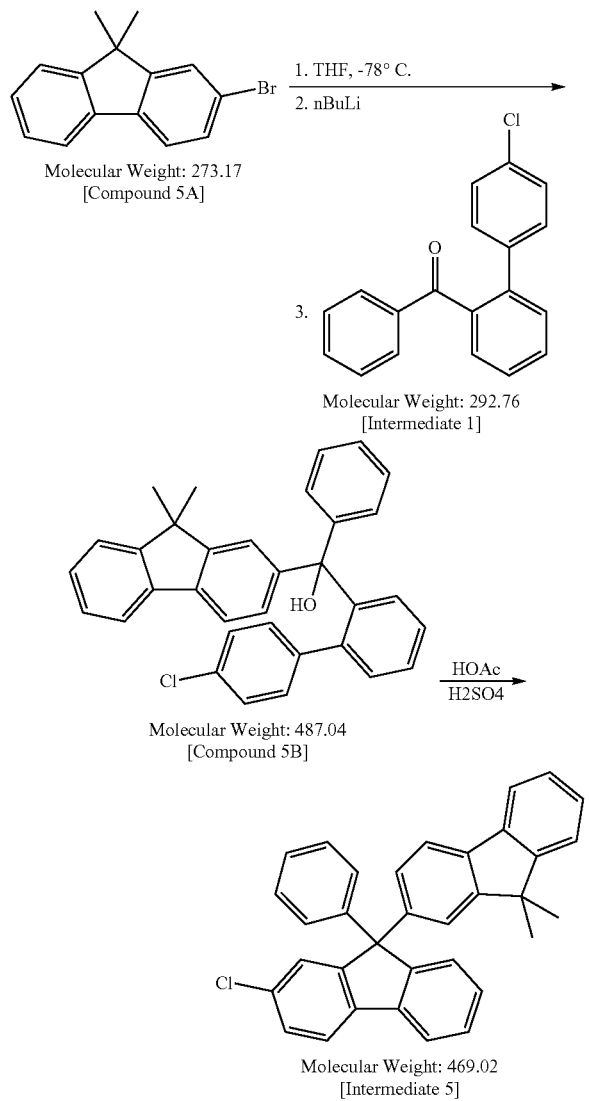

Compound 5A (10.0 g, 37 mmol) was placed in 100 ml of anhydrous tetrahydrofuran, and the result was cooled to −78° C. After that, n-butyllithium (2.5 M in hexane) (22 mL, 55 mmol) was slowly added dropwise thereto over 30 minutes while stirring, and the result was reacted for 1 hour. Then, Intermediate 1 (11 g, 37 mmol) was introduced thereto in a solid state, the temperature was slowly raised to room temperature, and the result was reacted for 4 hours. After the reaction, water was poured thereinto to terminate the reaction, the water layer and the organic layer were separated, and the organic layer was vacuum distilled to obtain Compound 5B. This was placed in 100 ml of acetic acid again, and then the result was refluxed after introducing 1 to 2 drops of sulfuric acid thereto as a catalyst while stirring. After reacting for 2 hours, the produced solids were filtered, the filtrate was dissolved in chloroform again, and then neutralized and extracted using water saturated with calcium carbonate, and the organic layer was dried using magnesium sulfate. After that, the organic layer was vacuum distilled and recrystallized using ethanol. The produced solids were filtered and dried to prepare Intermediate 5 (12 g, yield: 75%).

<Synthesis Example 6>—Preparation of Compound Represented by Intermediate 6

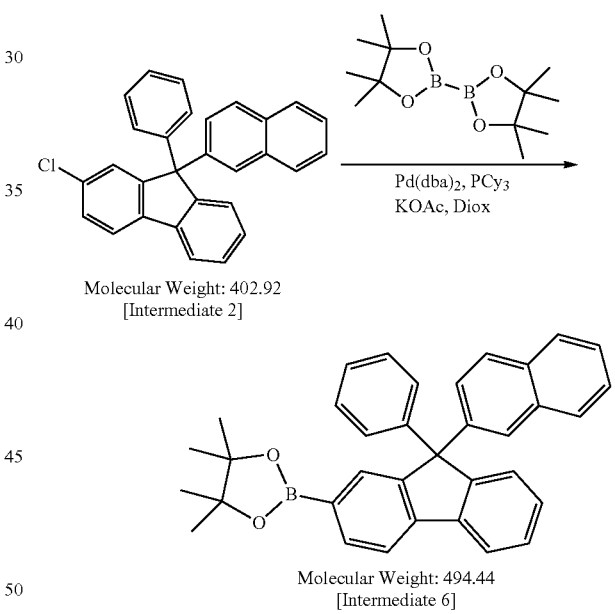

Under nitrogen atmosphere, Intermediate 2 (14 g, 35 mmol), bis(pinacolato)diboron (10 g, 38 mmol) and potassium acetate (10 g, 104 mmol) were mixed and added to 150 ml of dioxane, and the result was heated while stirring. While being refluxed, bis(dibenzylidineacetone)palladium (0.6 g, 1 mmol) and tricyclohexylphosphine (0.6 g, 2 mmol) were added thereto, and the result was heated and stirred for 3 hours. After the reaction was terminated, the temperature was lowered to room temperature and the result was filtered. Water was poured into the filtrate, the result was extracted with chloroform, and the organic layer was dried with anhydrous magnesium sulfate. The result was vacuum distilled and recrystallized with ethanol to prepare Intermediate 6 (14 g, yield: 79%).

<Synthesis Example 7>—Preparation of Compound Represented by Intermediate 7

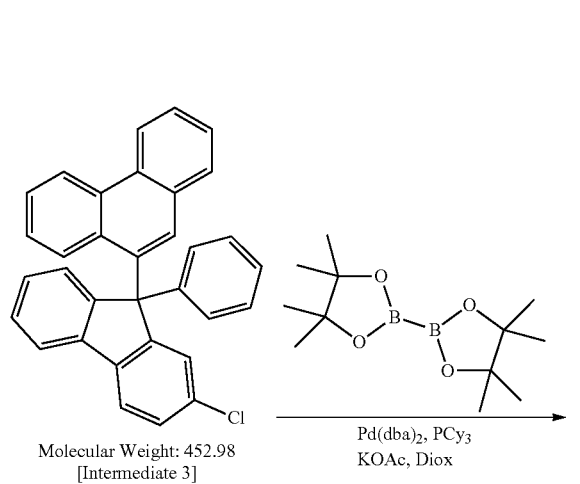

Under nitrogen atmosphere, Intermediate 3 (14 g, 31 mmol), bis(pinacolato)diboron (9 g, 34 mmol) and potassium acetate (9 g, 92 mmol) were mixed and added to 150 ml of dioxane, and the result was heated while stirring. While being refluxed, bis(dibenzylidineacetone)palladium (0.5 g, 1 mmol) and tricyclohexylphosphine (0.5 g, 2 mmol) were added thereto, and the result was heated and stirred for 3 hours. After the reaction was terminated, the temperature was lowered to room temperature and the result was filtered. Water was poured into the filtrate, the result was extracted with chloroform, and the organic layer was dried with anhydrous magnesium sulfate. The result was vacuum distilled and recrystallized with ethanol to prepare Intermediate 7 (14 g, yield: 84%).

<Synthesis Example 8>—Preparation of Compound Represented by Intermediate 8

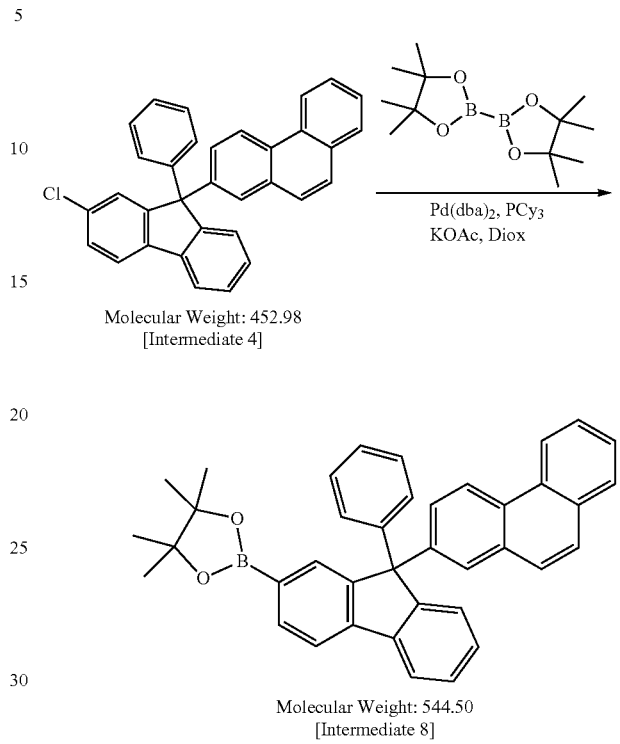

Under nitrogen atmosphere, Intermediate 4 (14 g, 31 mmol), bis(pinacolato)diboron (9 g, 34 mmol) and potassium acetate (9 g, 92 mmol) were mixed and added to 150 ml of dioxane, and the result was heated while stirring. While being refluxed, bis(dibenzylidineacetone)palladium (0.5 g, 1 mmol) and tricyclohexylphosphine (0.5 g, 2 mmol) were added thereto, and the result was heated and stirred for 3 hours. After the reaction was terminated, the temperature was lowered to room temperature and the result was filtered. Water was poured into the filtrate, the result was extracted with chloroform, and the organic layer was dried with anhydrous magnesium sulfate. The result was vacuum distilled and recrystallized with ethanol to prepare Intermediate 8 (12 g, yield: 73%).

<Synthesis Example 9>—Preparation of Compound Represented by Intermediate 9

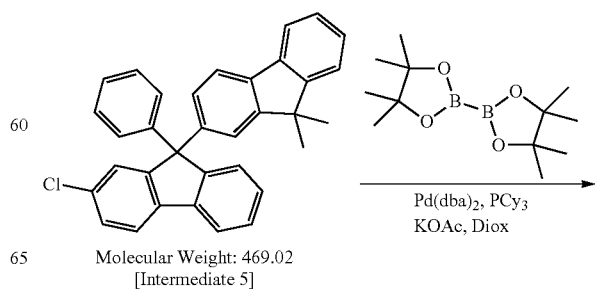

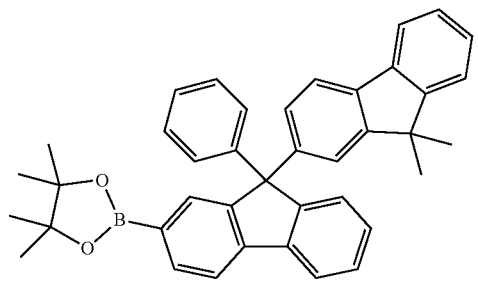

Molecular Weight: 560.54
[Intermediate 9]

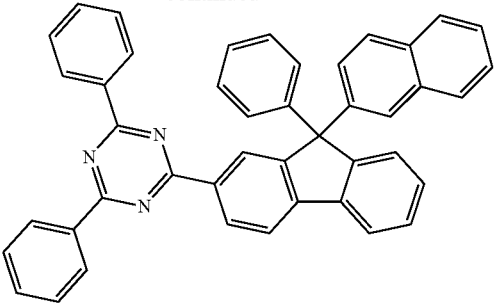

Molecular Weight: 599.74
[Compound 1]

Under nitrogen atmosphere, Intermediate 5 (12 g, 26 mmol), bis(pinacolato)diboron (7 g, 28 mmol) and potassium acetate (9 g, 92 mmol) were mixed and added to 150 ml of dioxane, and the result was heated while stirring. While being refluxed, bis(dibenzylidineacetone)palladium (0.4 g, 1 mmol) and tricyclohexylphosphine (0.4 g, 2 mmol) were added thereto, and the result was heated and stirred for 3 hours. After the reaction was terminated, the temperature was lowered to room temperature and the result was filtered. Water was poured into the filtrate, the result was extracted with chloroform, and the organic layer was dried with anhydrous magnesium sulfate. The result was vacuum distilled and recrystallized with ethanol to prepare Intermediate 9 (10 g, yield: 70%).

Under nitrogen atmosphere, Compound 10A (5 g, 19 mmol) and Intermediate 6 (10 g, 19 mmol) were placed in 100 ml of tetrahydrofuran, and the mixture was stirred and refluxed. After that, potassium carbonate (8 g, 57 mmol) dissolved in 30 ml of water was introduced thereto and the result was sufficiently stirred, and then tetrakistriphenylphosphino palladium (1 g, 0.6 mmol) was introduced thereto. After reacting for 18 hours, the temperature was lowered to room temperature and the result was filtered. The filtrate was extracted using chloroform and water, and the organic layer was dried using magnesium sulfate. After that, the organic layer was vacuum distilled and recrystallized using ethyl acetate. The produced solids were filtered and dried to prepare Compound 1 (8 g, yield: 70%). Compound 10A was purchased from Alpha.

MS: [M+H]+=599

<Synthesis Example 10>—Preparation of Compound Represented by Compound 1

<Synthesis Example 11>—Preparation of Compound Represented by Compound 2

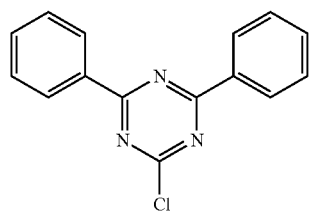

Molecular Weight: 267.72
[Compound 10A]

+

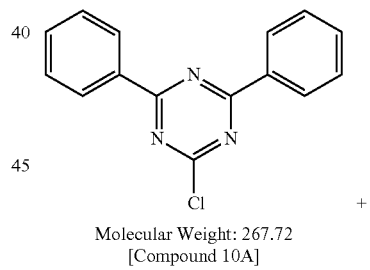

Molecular Weight: 267.72
[Compound 10A]

+

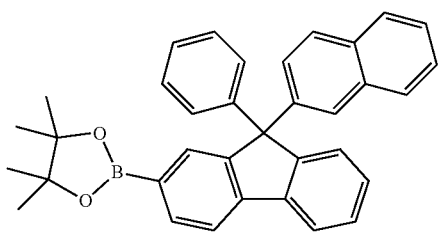

Molecular Weight: 494.44
[Intermediate 6]

TTP, K$_2$CO$_3$
———————→
THF/H2O

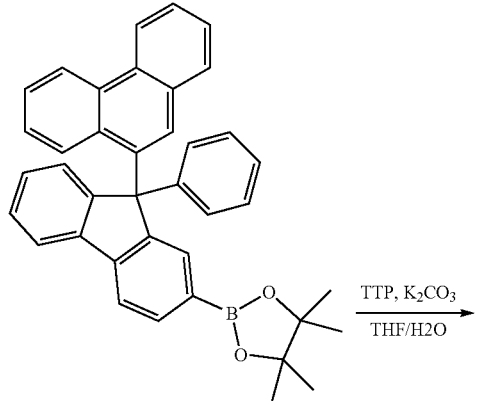

Molecular Weight: 544.50
[Intermediate 7]

TTP, K$_2$CO$_3$
———————→
THF/H2O

-continued

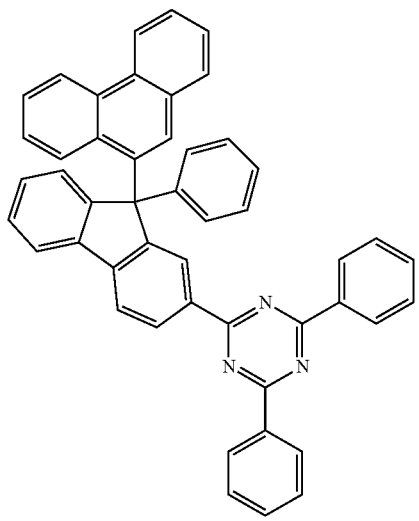

Molecular Weight: 649.80
[Compound 2]

Under nitrogen atmosphere, Compound 10A (5 g, 19 mmol) and Intermediate 7 (10 g, 19 mmol) were placed in 100 ml of tetrahydrofuran, and the mixture was stirred and refluxed. After that, potassium carbonate (8 g, 57 mmol) dissolved in 30 ml of water was introduced thereto and the result was sufficiently stirred, and then tetrakistriphenylphosphino palladium (1 g, 0.6 mmol) was introduced thereto. After reacting for 18 hours, the temperature was lowered to room temperature and the result was filtered. The filtrate was extracted using chloroform and water, and the organic layer was dried using magnesium sulfate. After that, the organic layer was vacuum distilled and recrystallized using ethyl acetate. The produced solids were filtered and dried to prepare Compound 2 (7 g, yield: 60%).

MS: [M+H]+=649

<Synthesis Example 12>—Preparation of Compound Represented by Compound 3

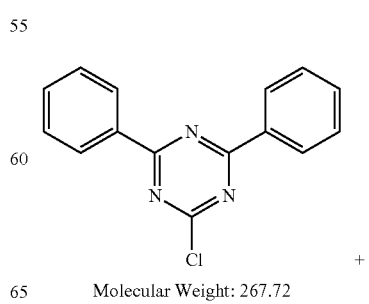

Molecular Weight: 267.72
[Compound 10A]

-continued

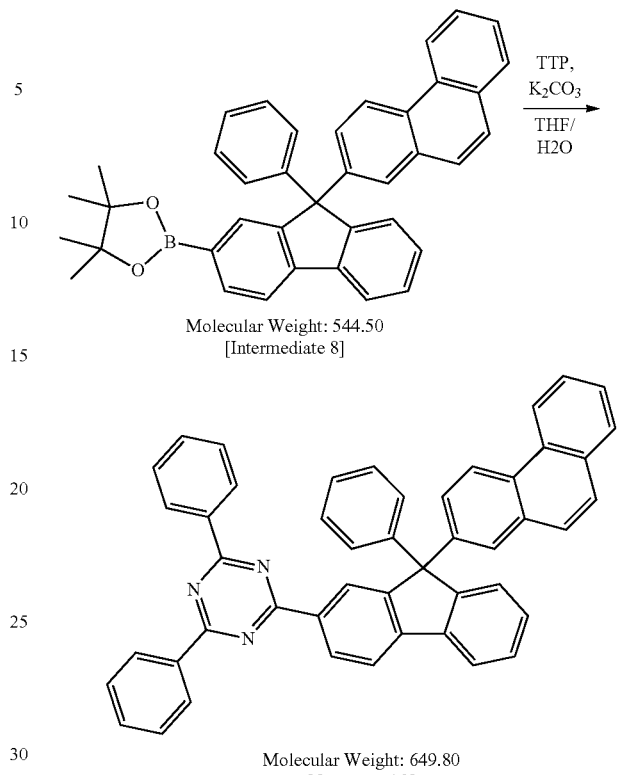

Molecular Weight: 544.50
[Intermediate 8]

Molecular Weight: 649.80
[Compound 3]

Under nitrogen atmosphere, Compound 10A (5 g, 19 mmol) and Intermediate 8 (10 g, 19 mmol) were placed in 100 ml of tetrahydrofuran, and the mixture was stirred and refluxed. After that, potassium carbonate (8 g, 57 mmol) dissolved in 30 ml of water was introduced thereto and the result was sufficiently stirred, and then tetrakistriphenylphosphino palladium (1 g, 0.6 mmol) was introduced thereto. After reacting for 18 hours, the temperature was lowered to room temperature and the result was filtered. The filtrate was extracted using chloroform and water, and the organic layer was dried using magnesium sulfate. After that, the organic layer was vacuum distilled and recrystallized using ethyl acetate. The produced solids were filtered and dried to prepare Compound 3 (9 g, yield: 71%).

MS: [M+H]+=649

<Synthesis Example 13>—Preparation of Compound Represented by Compound 4

Molecular Weight: 267.72
[Compound 10A]

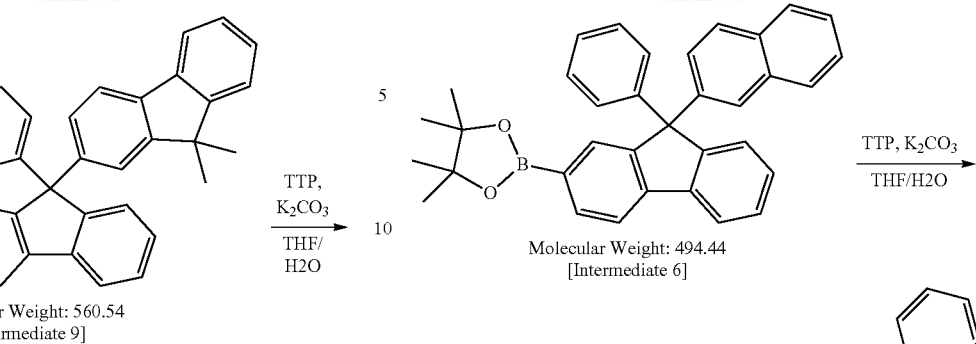

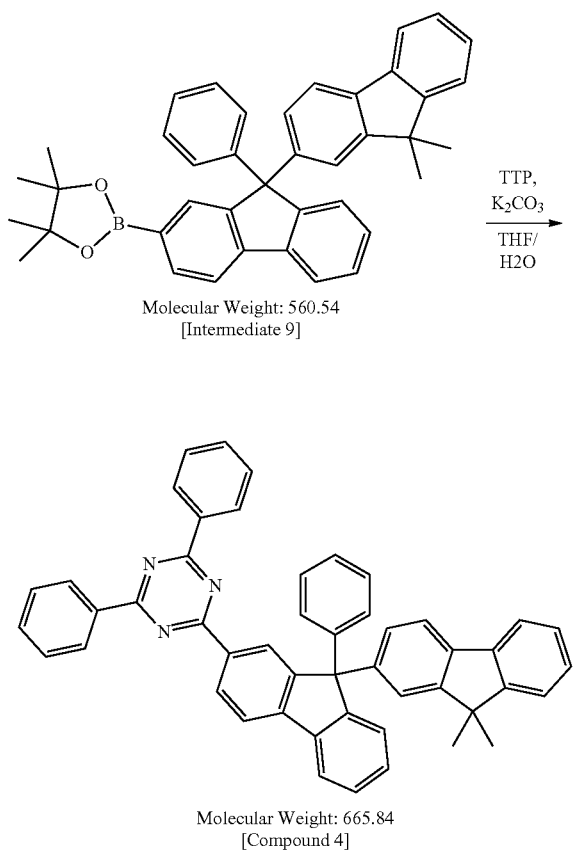

Under nitrogen atmosphere, Compound 10A (5 g, 19 mmol) and Intermediate 9 (11 g, 19 mmol) were placed in 100 ml of tetrahydrofuran, and the mixture was stirred and refluxed. After that, potassium carbonate (8 g, 57 mmol) dissolved in 30 ml of water was introduced thereto and the result was sufficiently stirred, and then tetrakistriphenyl-phosphino palladium (1 g, 0.6 mmol) was introduced thereto. After reacting for 18 hours, the temperature was lowered to room temperature and the result was filtered. The filtrate was extracted using chloroform and water, and the organic layer was dried using magnesium sulfate. After that, the organic layer was vacuum distilled and recrystallized using ethyl acetate. The produced solids were filtered and dried to prepare Compound 4 (7 g, yield: 55%).

MS: [M+H]+=665

<Synthesis Example 14>—Preparation of Compound Represented by Compound 5

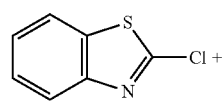

Molecular Weight: 169.63
[Compound 14A]

Under nitrogen atmosphere, Compound 14A (5 g, 29 mmol) and Intermediate 6 (17 g, 29 mmol) were placed in 100 ml of tetrahydrofuran, and the mixture was stirred and refluxed. After that, potassium carbonate (12 g, 88 mmol) dissolved in 40 ml of water was introduced thereto and the result was sufficiently stirred, and then tetrakistriphenyl-phosphino palladium (1 g, 0.9 mmol) was introduced thereto. After reacting for 18 hours, the temperature was lowered to room temperature and the result was filtered. The filtrate was extracted using chloroform and water, and the organic layer was dried using magnesium sulfate. After that, the organic layer was vacuum distilled and recrystallized using ethyl acetate. The produced solids were filtered and dried to prepare Compound 5 (10 g, 67%). Compound 14A was purchased from TCI.

MS: [M+H]+=501

<Synthesis Example 15>—Preparation of Compound Represented by Compound 6

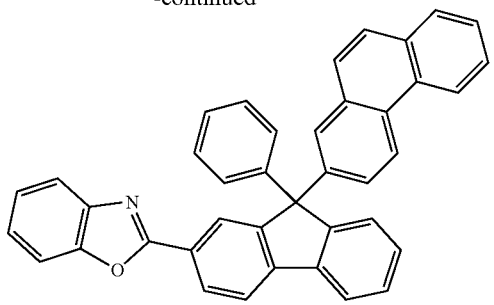

Molecular Weight: 535.65
[Compound 6]

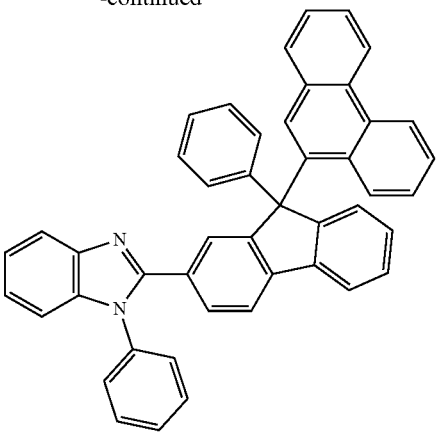

Molecular Weight: 610.76
[Compound 7]

Under nitrogen atmosphere, Compound 15A (5 g, 33 mmol) and Intermediate 8 (18 g, 33 mmol) were placed in 100 ml of tetrahydrofuran, and the mixture was stirred and refluxed. After that, potassium carbonate (14 g, 98 mmol) dissolved in 40 ml of water was introduced thereto and the result was sufficiently stirred, and then tetrakistriphenylphosphino palladium (1 g, 1.0 mmol) was introduced thereto. After reacting for 18 hours, the temperature was lowered to room temperature and the result was filtered. The filtrate was extracted using chloroform and water, and the organic layer was dried using magnesium sulfate. After that, the organic layer was vacuum distilled and recrystallized using ethyl acetate. The produced solids were filtered and dried to prepare Compound 6 (12 g, yield: 71%). Compound 15A was purchased from TCI.

MS: [M+H]+=535

<Synthesis Example 16>—Preparation of Compound Represented by Compound 7

Under nitrogen atmosphere, Compound 16A (5 g, 22 mmol) and Intermediate 7 (12 g, 22 mmol) were placed in 100 ml of tetrahydrofuran, and the mixture was stirred and refluxed. After that, potassium carbonate (9 g, 66 mmol) dissolved in 40 ml of water was introduced thereto and the result was sufficiently stirred, and then tetrakistriphenylphosphino palladium (1 g, 1.0 mmol) was introduced thereto. After reacting for 18 hours, the temperature was lowered to room temperature and the result was filtered. The filtrate was extracted using chloroform and water, and the organic layer was dried using magnesium sulfate. After that, the organic layer was vacuum distilled and recrystallized using ethyl acetate. The produced solids were filtered and dried to prepare Compound 7 (10 g, yield: 77%). Compound 16A was purchased from TCI.

MS: [M+H]+=610

<Synthesis Example 17>—Preparation of Compound Represented by Compound 8

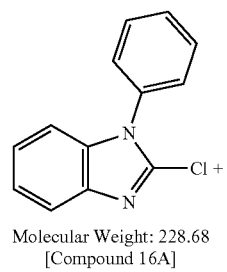

Molecular Weight: 228.68
[Compound 16A]

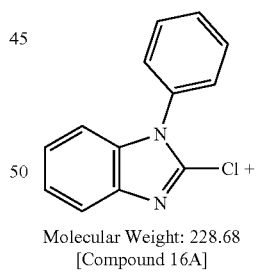

Molecular Weight: 228.68
[Compound 16A]

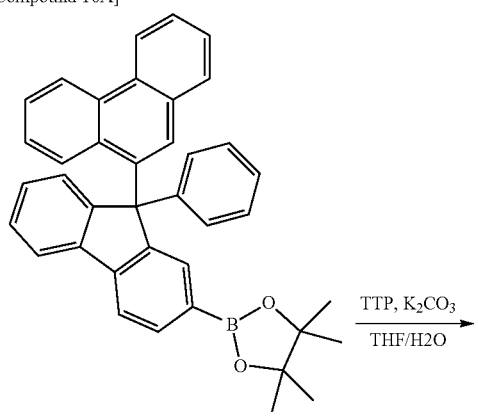

Molecular Weight: 544.50
[Intermediate 7]

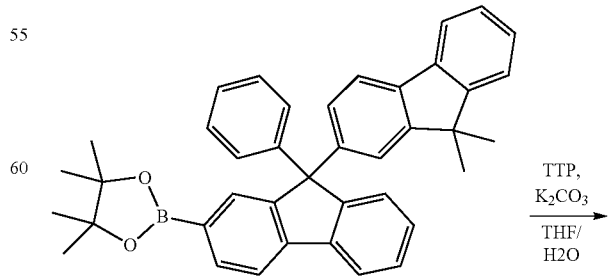

Molecular Weight: 560.54
[Intermediate 7]

-continued

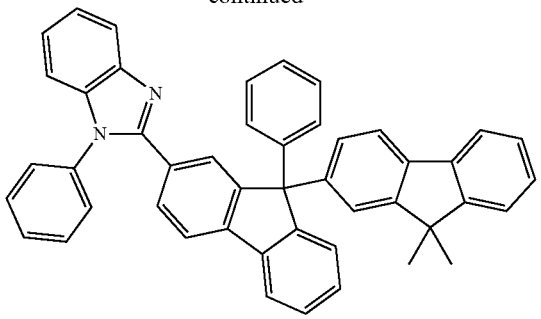

Molecular Weight: 626.80
[Compound 8]

Under nitrogen atmosphere, Compound 16A (5 g, 22 mmol) and Intermediate 7 (12 g, 22 mmol) were placed in 100 ml of tetrahydrofuran, and the mixture was stirred and refluxed. After that, potassium carbonate (9 g, 66 mmol) dissolved in 40 ml of water was introduced thereto and the result was sufficiently stirred, and then tetrakistriphenylphosphino palladium (1 g, 1.0 mmol) was introduced thereto. After reacting for 18 hours, the temperature was lowered to room temperature and the result was filtered. The filtrate was extracted using chloroform and water, and the organic layer was dried using magnesium sulfate. After that, the organic layer was vacuum distilled and recrystallized using ethyl acetate. The produced solids were filtered and dried to prepare Compound 8 (11 g, yield: 80%).

MS: [M+H]+=626

EXAMPLE

Example 1-1

A glass substrate (corning 7059 glass) on which indium tin oxide (ITO) was coated as a thin film to a thickness of 1,000 Å was placed in dispersant-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol in this order, then dried.

On the transparent ITO electrode prepared as above, a hole injection layer was formed by thermal vacuum depositing hexanitrile hexaazatriphenylene to a thickness of 500 Å. HT1 (400 Å), a material transferring holes, was vacuum deposited thereon, and host H1 and dopant D1 compounds were vacuum deposited to a thickness of 300 Å as a light emitting layer. On the light emitting layer, an electron injection and transfer layer was formed to a thickness of 350 Å by vacuum depositing Compound 1 prepared in Synthesis Example 10 and lithium quinolate (LiQ) in a weight ratio of 1:1. A cathode was formed on the electron injection and transfer layer by depositing lithium fluoride (LiF) to a thickness of 12 Å and aluminum to a thickness of 2,000 Å in consecutive order, and as a result, an organic light emitting device was manufactured.

The organic light emitting device was manufactured by maintaining, in the above-mentioned processes, the deposition rates of the organic materials at 0.4 Å/sec to 0.7 Å/sec, the deposition rates of the lithium fluoride and the aluminum of the cathode at 0.3 Å/sec and 2 Å/sec, respectively, and the degree of vacuum during the deposition at $2 \times 10^{-7}$ torr to $5 \times 10^{-6}$ torr.

[hexanitrile hexaazatriphenylene] [LiQ]

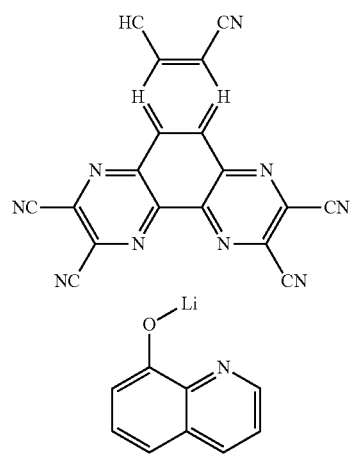

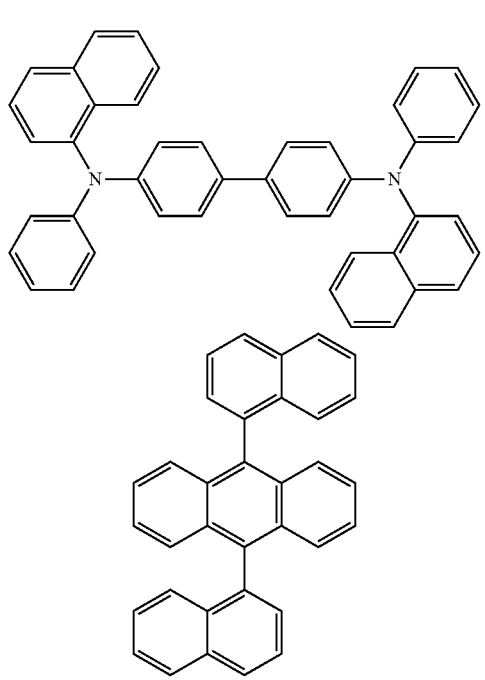

[HT1]

[H1]

[D1]

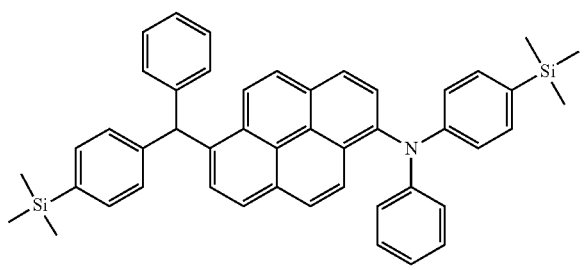

Example 1-2

An experiment was carried out in the same manner as in Example 1-1 except that Compound 2 was used instead of Compound 1 as the electron transfer layer.

Example 1-3

An experiment was carried out in the same manner as in Example 1-1 except that Compound 3 was used instead of Compound 1 as the electron transfer layer.

Example 1-4

An experiment was carried out in the same manner as in Example 1-1 except that Compound 4 was used instead of Compound 1 as the electron transfer layer.

Example 1-5

An experiment was carried out in the same manner as in Example 1-1 except that Compound 5 was used instead of Compound 1 as the electron transfer layer.

Example 1-6

An experiment was carried out in the same manner as in Example 1-1 except that Compound 6 was used instead of Compound 1 as the electron transfer layer.

Example 1-7

An experiment was carried out in the same manner as in Example 1-1 except that Compound 7 was used instead of Compound 1 as the electron transfer layer.

Example 1-8

An experiment was carried out in the same manner as in Example 1-1 except that Compound 8 was used instead of Compound 1 as the electron transfer layer.

Comparative Example 1-1

An organic light emitting device was manufactured in the same manner as in Example 1-1 except that the following compound of ET1 was used instead of Compound 1.

[ET1]

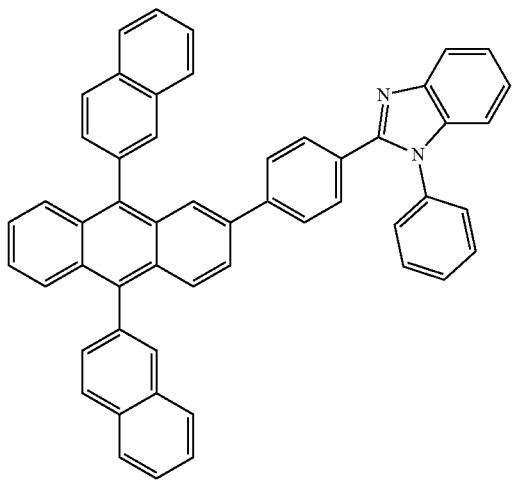

Comparative Example 1-2

An organic light emitting device was manufactured in the same manner as in Example 1-1 except that the following compound of ET2 was used instead of Compound 1.

[ET2]

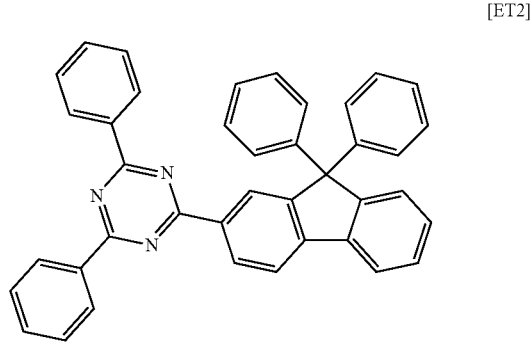 [SMILES: c1ccc(-c2nc(-c3ccccc3)nc(-c3ccc4c(c3)C(c3ccccc3)(c3ccccc3)c3ccccc3-4)n2)cc1]

For the organic light emitting device manufactured using each of the compounds as an electron transfer layer material as in Examples 1-1 to 1-8 and Comparative Example 1-1 to Comparative Example 1-3, a driving voltage and light emission efficiency were measured at current density of 10 mA/cm$^2$, and time taken for the luminance decreasing to 98% of its initial luminance (LT$_{98}$) was measured at current density of 20 mA/cm$^2$. The results are shown in the following Table 1.

TABLE 1

| Example (at 10 mA/cm$^2$) | Compound | Driving Voltage (@20 mA/cm$^2$) | Current Efficiency (@ 20 mA/cm$^2$) | Color Coordinate (x axis, y axis) | Life Time 95% (at 20 mA/cm$^2$) |
|---|---|---|---|---|---|
| Example 1-1 | Compound 1 | 4.00 | 7.58 | (0.134, 0.133) | 103 |
| Example 1-2 | Compound 2 | 4.05 | 7.45 | (0.134, 0.133) | 111 |
| Example 1-3 | Compound 3 | 4.05 | 7.39 | (0.134, 0.133) | 110 |
| Example 1-4 | Compound 4 | 4.08 | 7.62 | (0.134, 0.133) | 90 |
| Example 1-5 | Compound 5 | 4.50 | 5.75 | (0.134, 0.133) | 170 |
| Example 1-6 | Compound 6 | 4.70 | 5.91 | (0.134, 0.133) | 180 |
| Example 1-7 | Compound 7 | 4.28 | 6.10 | (0.134, 0.133) | 170 |
| Example 1-8 | Compound 8 | 4.38 | 6.10 | (0.134, 0.133) | 150 |
| Comparative Example 1-1 | ET1 | 3.94 | 5.80 | (0.134, 0.133) | 80 |
| Comparative Example 1-2 | ET2 | 4.02 | 6.42 | (0.131, 0.134) | 66 |

From the results of Table 1, it was identified that the compound represented by Chemical Formula 1 according to one embodiment of the present specification was capable of being used in an electron injection layer or an electron transfer layer of an organic electronic device.

Specifically, when comparing Examples 1-1 to 1-8 according to Chemical Formula 1 of the present specification with Comparative Example 1-2, it was identified that excellent properties were obtained in terms of driving voltage, current efficiency and/or lifespan in the organic electronic device when 9,9 positions of fluorene were substituted with different functional groups as in Chemical Formula 1 compared to when substituted with the same functional group.

In addition, when comparing Examples 1-7 and 1-8 with Comparative Example 1-1, it was identified the structure of Chemical Formula 1 comprising a fluorenyl group in the basic skeleton structure resulted in excellent properties in the organic electronic device compared to the structure comprising an anthracenyl group in the basic skeleton structure.

Accordingly, it was seen that the organic light emitting device manufactured using the compound represented by Chemical Formula 1 of the present specification as an electron transfer layer material had low driving voltage and had excellent properties in terms of efficiency and lifespan.

The invention claimed is:

1. A compound represented by the following Chemical Formula 1:

[Chemical Formula 1]

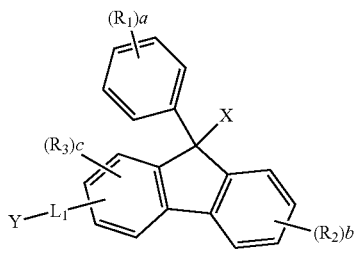

wherein, in Chemical Formula 1,

X is a substituted phenyl group; a substituted or unsubstituted naphthyl group, a substituted or unsubstituted phenanthryl group, a substituted or unsubstituted biphenyl group, a substituted or unsubstituted terphenyl group, a substituted or unsubstituted anthracenyl group, a substituted or unsubstituted triphenylene group, a substituted or unsubstituted pyrene group, a substituted or unsubstituted fluorenyl group, a substituted or unsubstituted pyridine group, or a substituted or unsubstituted isoquinoline group;

$L_1$ is a direct bond; a substituted or unsubstituted arylene group; or a substituted or unsubstituted heteroarylene group;

Y is selected from among the following structural formulae;

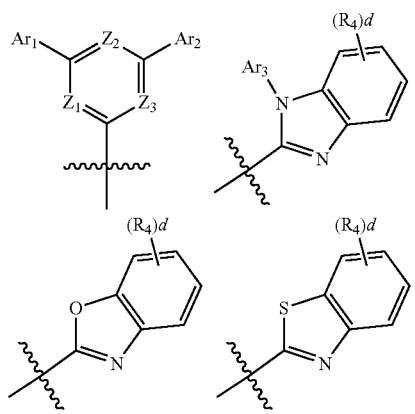

two or more of $Z_1$ to $Z_3$ are N, and the rest are N or CR;

$Ar_1$ to $Ar_3$ are the same as or different from each other, and each independently hydrogen; deuterium; a halogen group; a substituted or unsubstituted alkyl group; a substituted or unsubstituted cycloalkyl group; a substituted or unsubstituted phosphine oxide group; a substituted or unsubstituted aryl group; or a substituted or unsubstituted heteroaryl group;

R and $R_1$ to $R_4$ are the same as or different from each other, and each independently hydrogen; deuterium; a halogen group; a nitrile group; a nitro group; a hydroxyl group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted alkenyl group; a substituted or unsubstituted silyl group; a substituted or unsubstituted boron group; a substituted or unsubstituted phosphine oxide group; a substituted or unsubstituted amine group; a substituted or unsubstituted arylamine group; a substituted or unsubstituted aryl group; or a substituted or unsubstituted heteroaryl group;

a is an integer of 5;

b is an integer of 4;

c is an integer of 3;

d is an integer of 4;

a plurality of $R_1$s are the same as or different from each other;

a plurality of $R_2$s are the same as or different from each other;

a plurality of $R_3$s are the same as or different from each other; and a plurality of $R_4$s are the same as or different from each other, provided that when Y is

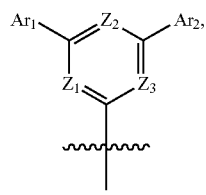

and X is the substituted phenyl group, then the substituent of the phenyl group for X is not an unsubstituted alkoxy group, an unsubstituted methyl group, an unsubstituted phenyl group, or a group comprising a substituted or unsubstituted arylamine group, when Y is

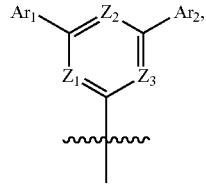

and X is the substituted biphenyl group, then the substituent of the biphenyl group for X is not a substituted or unsubstituted arylamine group, when Y is

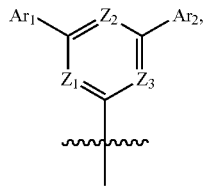

and X is the substituted anthracenyl group, then the substituent of the anthracenyl group for X is deuterium; a halogen group; a nitrile group; a nitro group; a hydroxyl group; a carbonyl group; an ester group; an imide group; an amide group; an alkoxy group; an alkyl group; a cycloalkyl group; an aryloxy group; an alkylthioxy group; an arylthioxy group; an alkylsulfoxy group; an alkenyl group; a silyl group; a boron group; an amine group; a phosphine oxide group; an arylamine group; a phenyl, a naphthyl group, a biphenyl group, a terphenyl group, a quaterphenyl group, an anthracenyl group, a phenanthryl group, a triphenylene group, a pyrenyl group, a perylenyl group, a chrysenyl group, a thiophene group, a furan group, a pyrrole group, an imidazole group, a thiazole group, an oxazole group, an oxadiazole group, a triazole group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, or a dibenzofuranyl group, each of which is unsubstituted, and when Y is

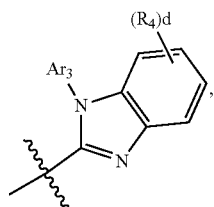

and X is the substituted phenyl group, then the substituent of the phenyl group for X is not a substituted or unsubstituted arylamine group.

2. The compound of claim 1, wherein

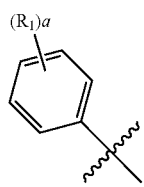

and X are different from each other.

3. The compound of claim 1, wherein $L_1$ is a direct bond; or a substituted or unsubstituted arylene group having 6 to 20 carbon atoms.

4. The compound of claim 1, wherein Ar1 to Ar3 are the same as or different from each other, and each independently a substituted or unsubstituted phenyl group, a substituted or unsubstituted biphenyl group, or a substituted or unsubstituted naphthyl group.

5. The compound of claim 1, wherein R and R1 to R4 are hydrogen.

6. The compound of claim 1, wherein Chemical Formula 1 is represented by the following Chemical Formulae 2 to 4:

[Chemical Formula 2]

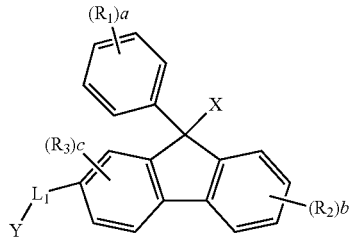

[Chemical Formula 3]

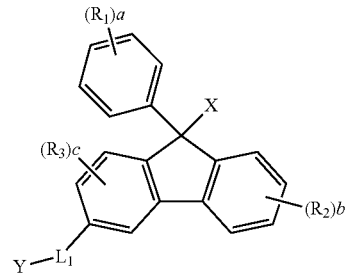

[Chemical Formula 4]

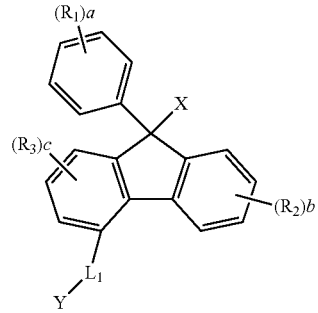

wherein Chemical Formulae 2 to 4, definitions of X, Y, $L_1$, R, $R_1$ to $R_3$ and a to c are the same as in Chemical Formula 1.

7. The compound of claim 1, wherein Chemical Formula 1 is any one selected from among the following compounds:
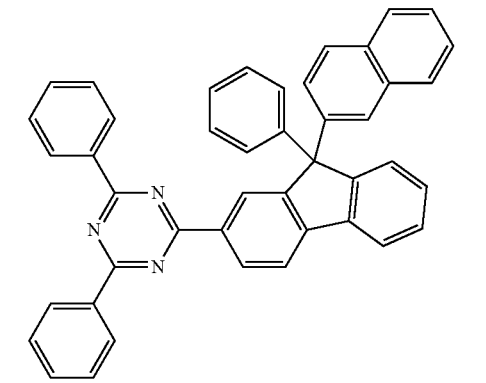
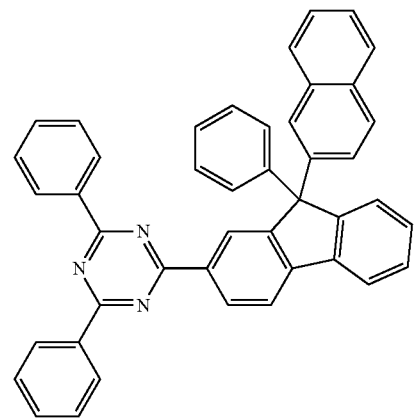
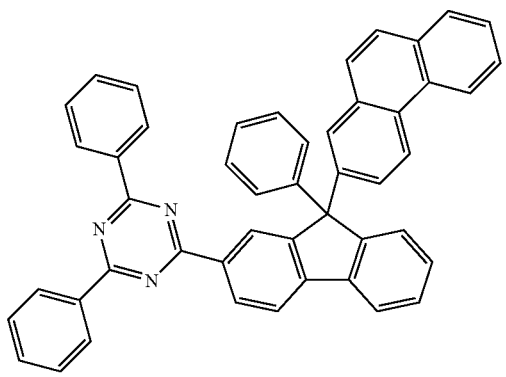
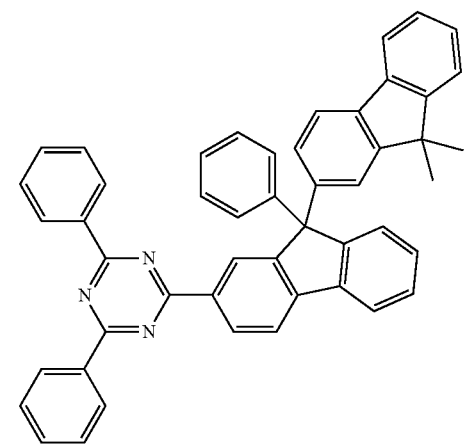
-continued
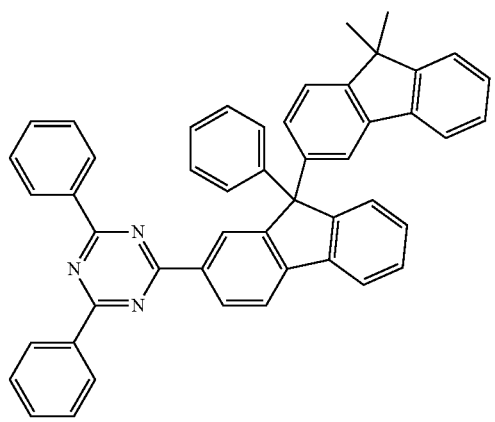
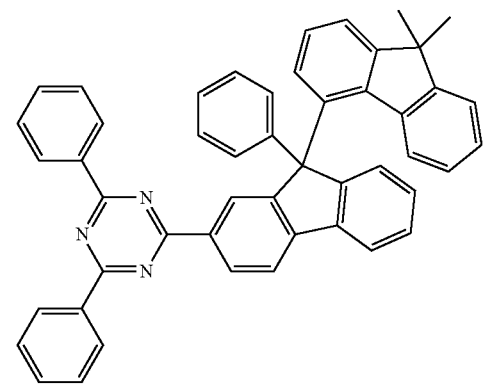
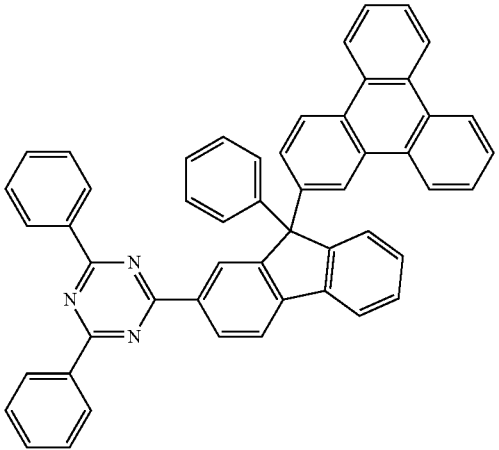
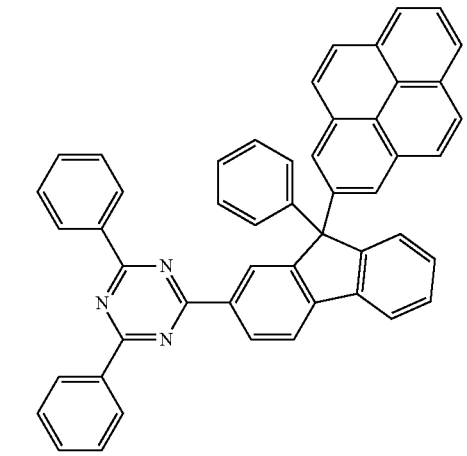

75
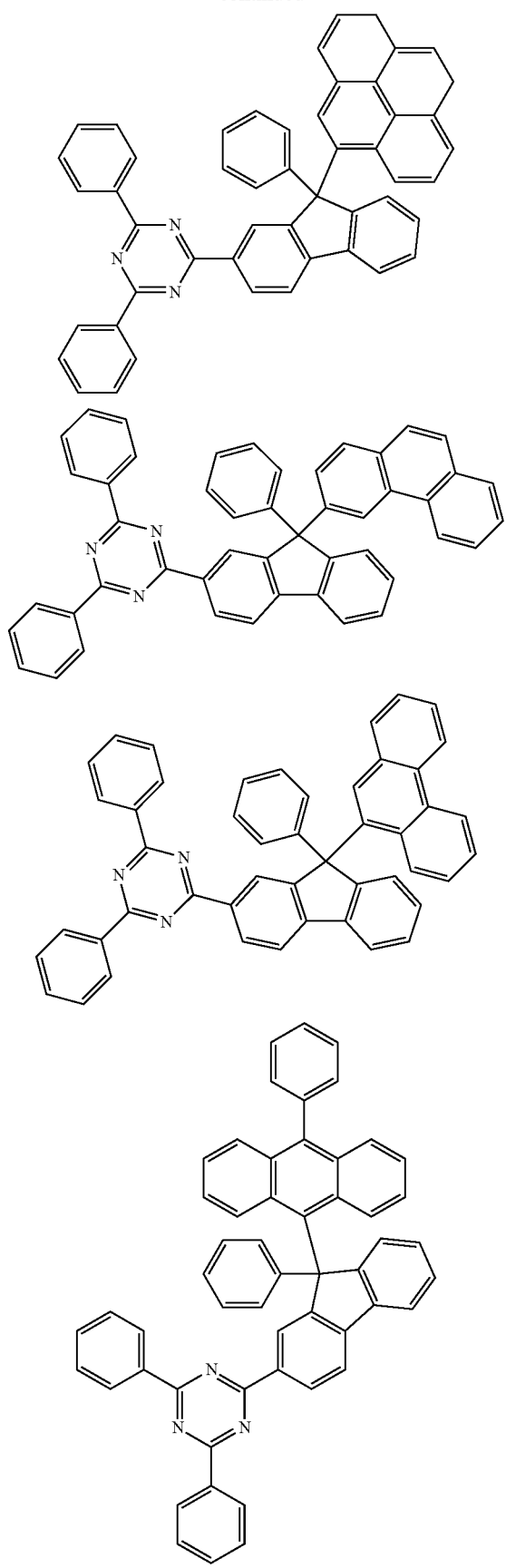
76
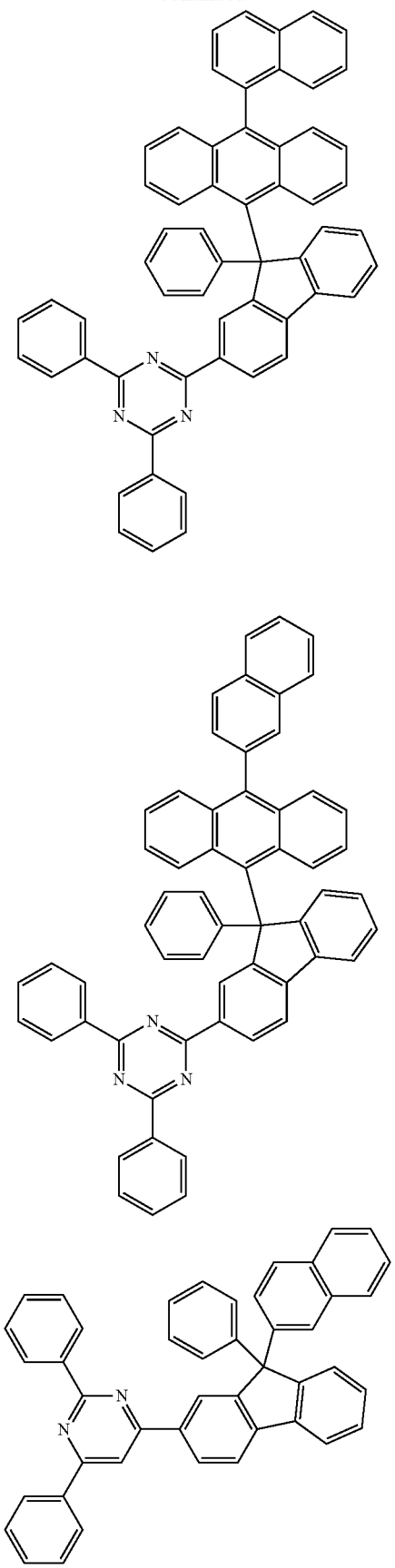

77
-continued
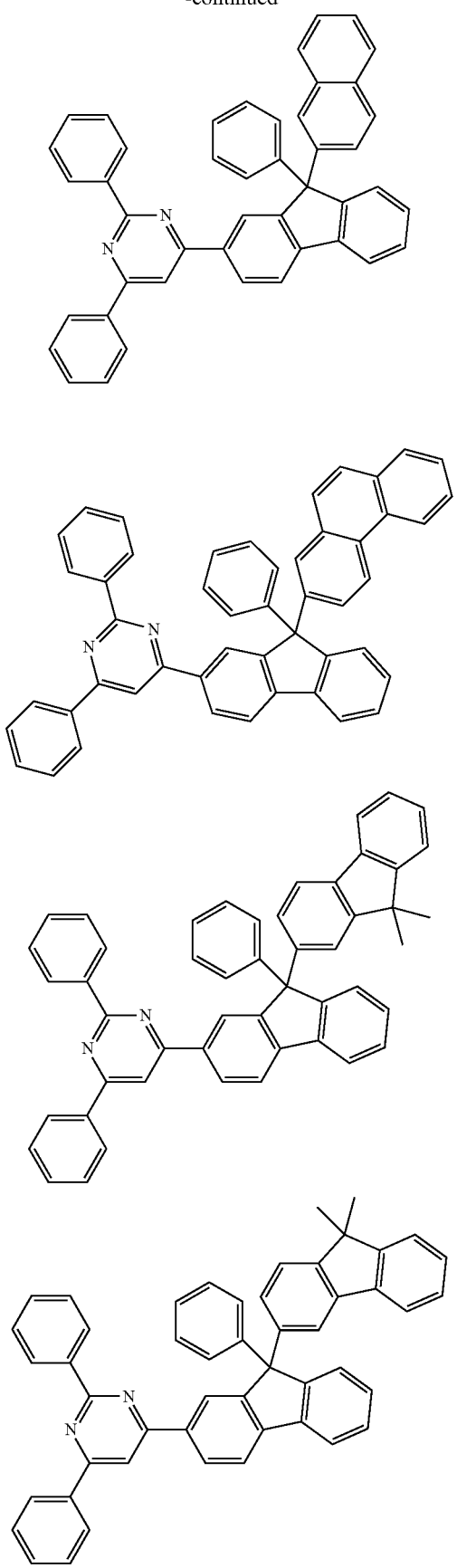
78
-continued
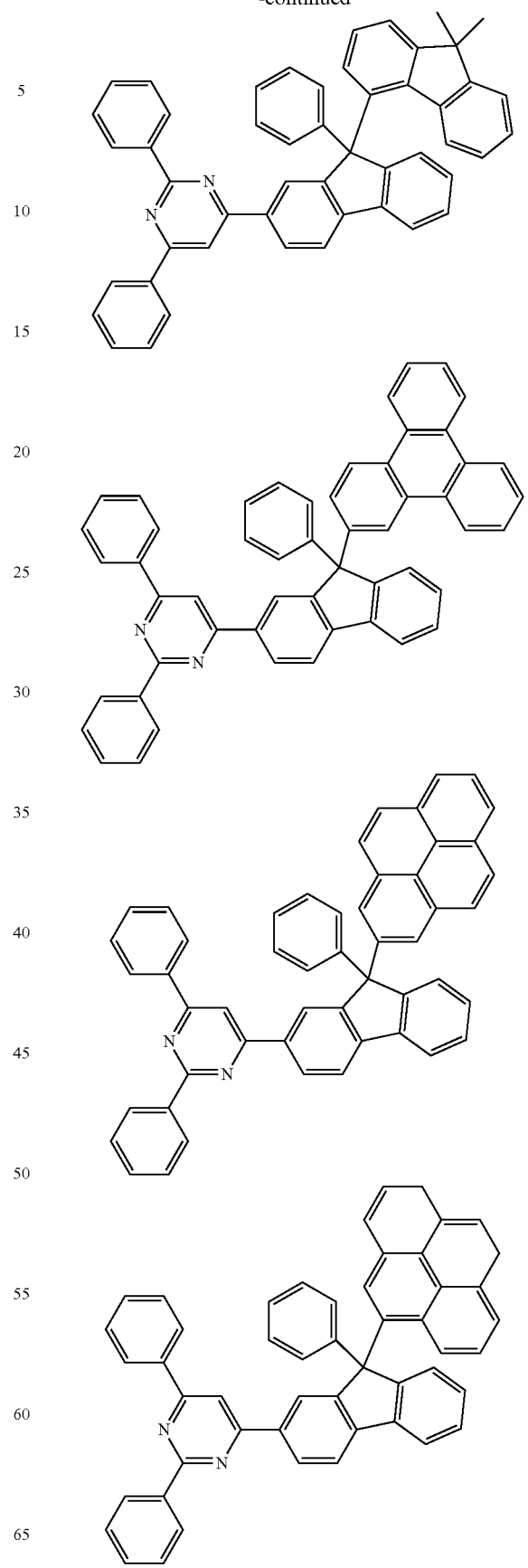

79
-continued
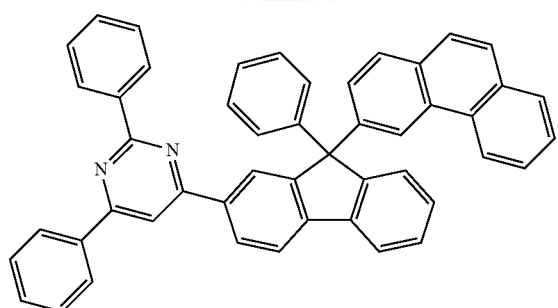
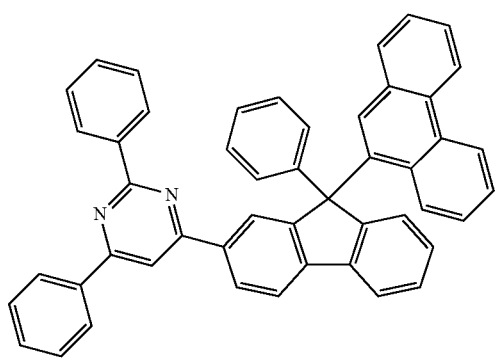
80
-continued
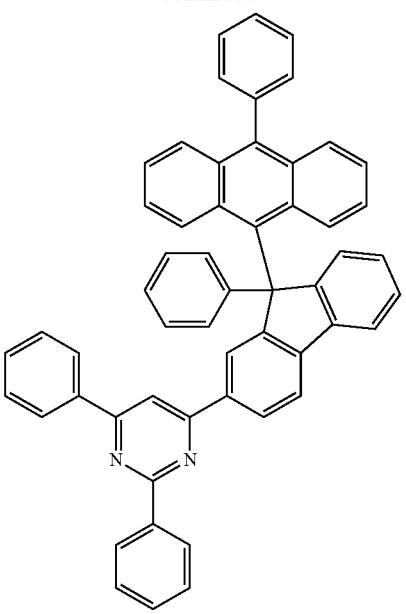
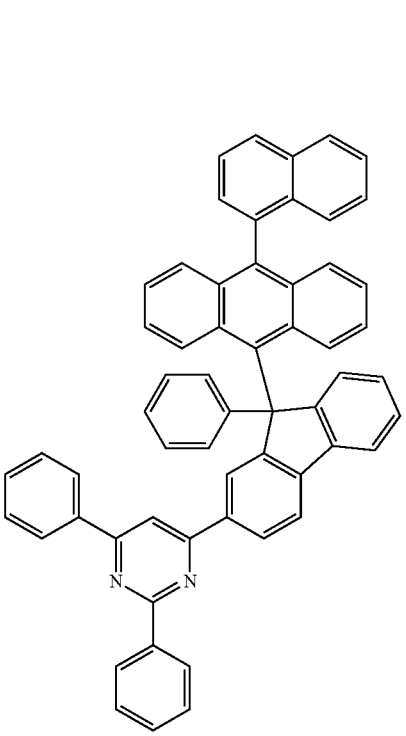

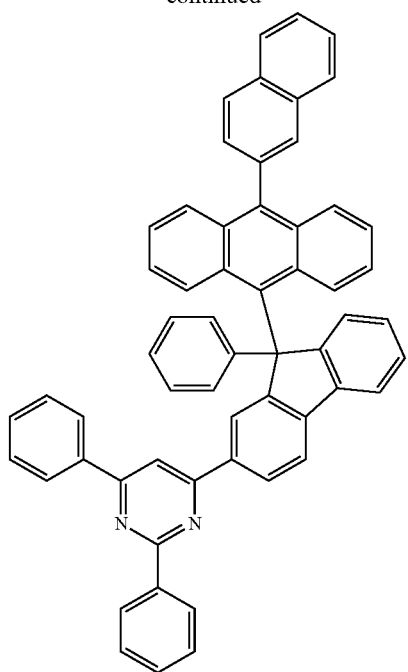
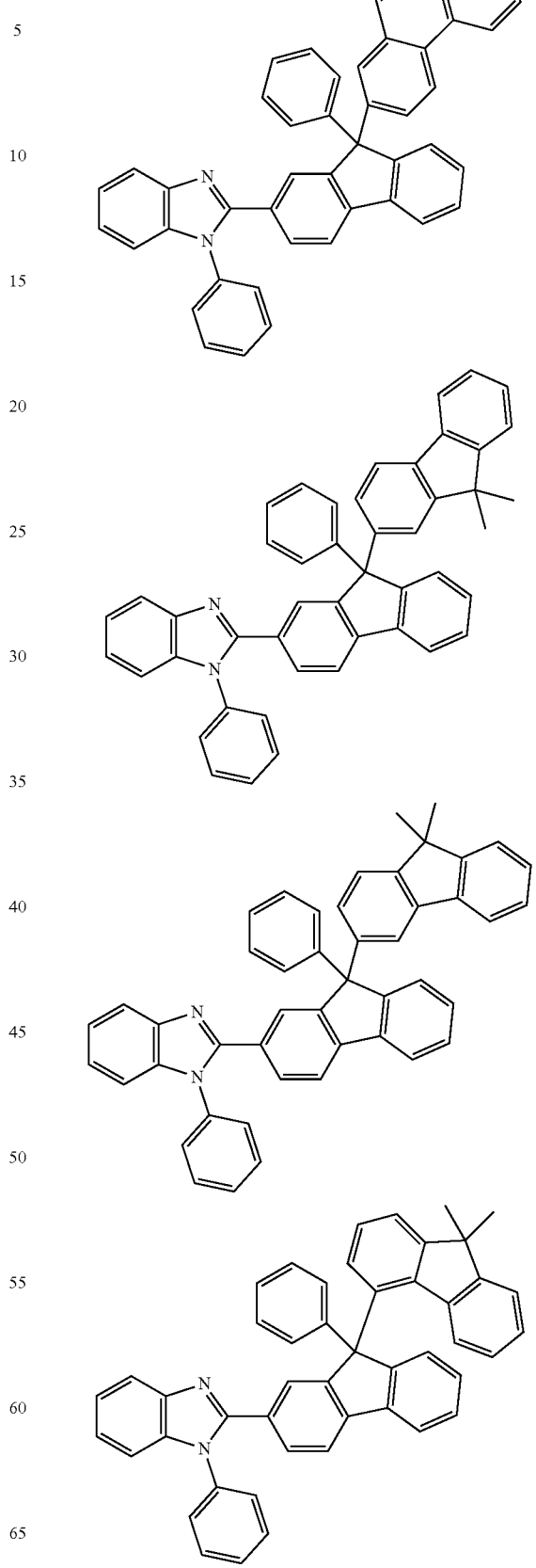

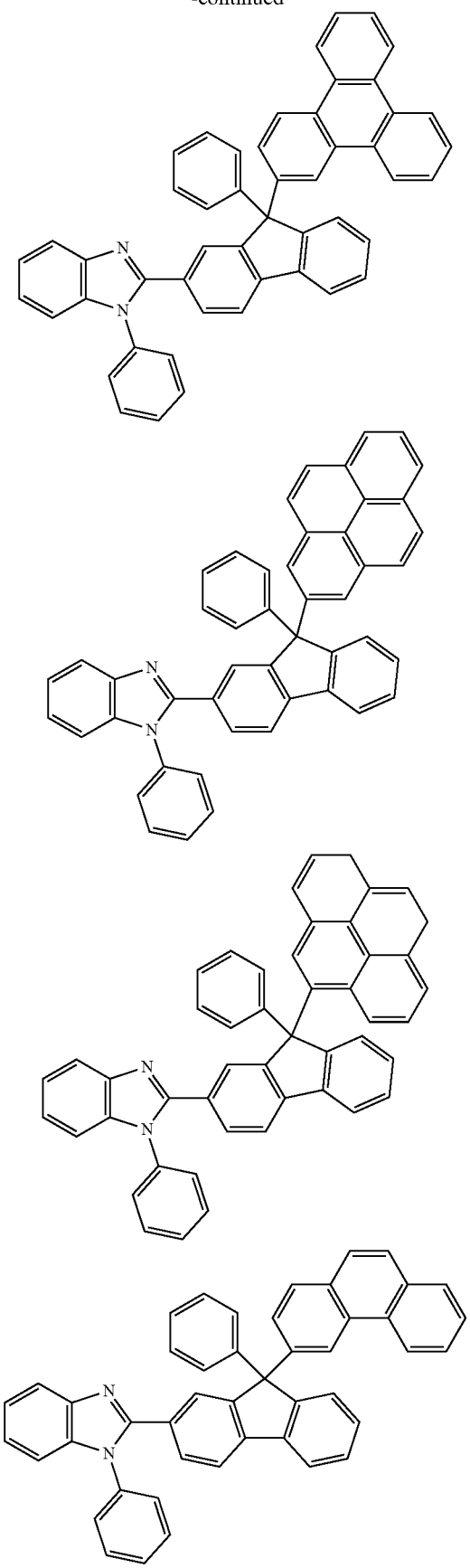
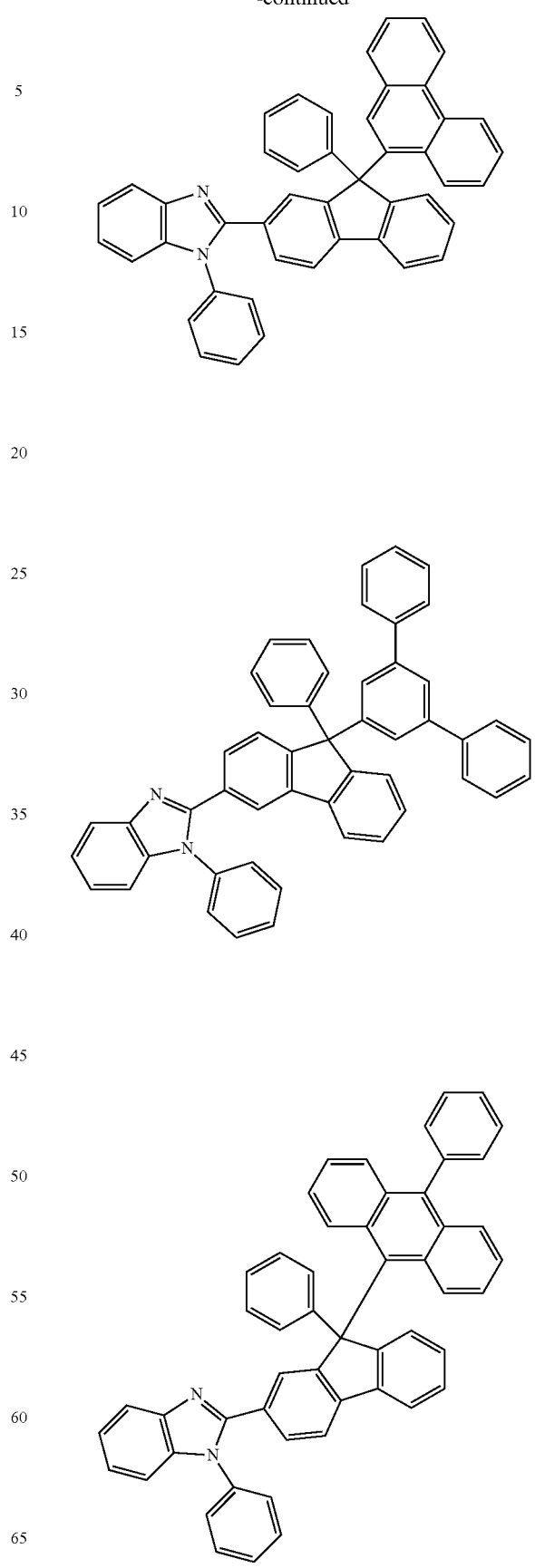

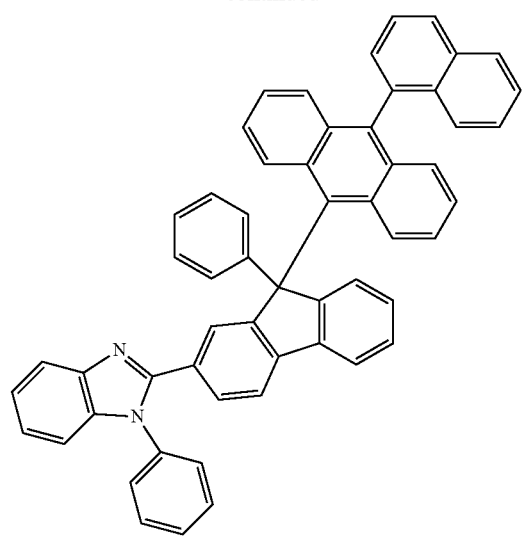
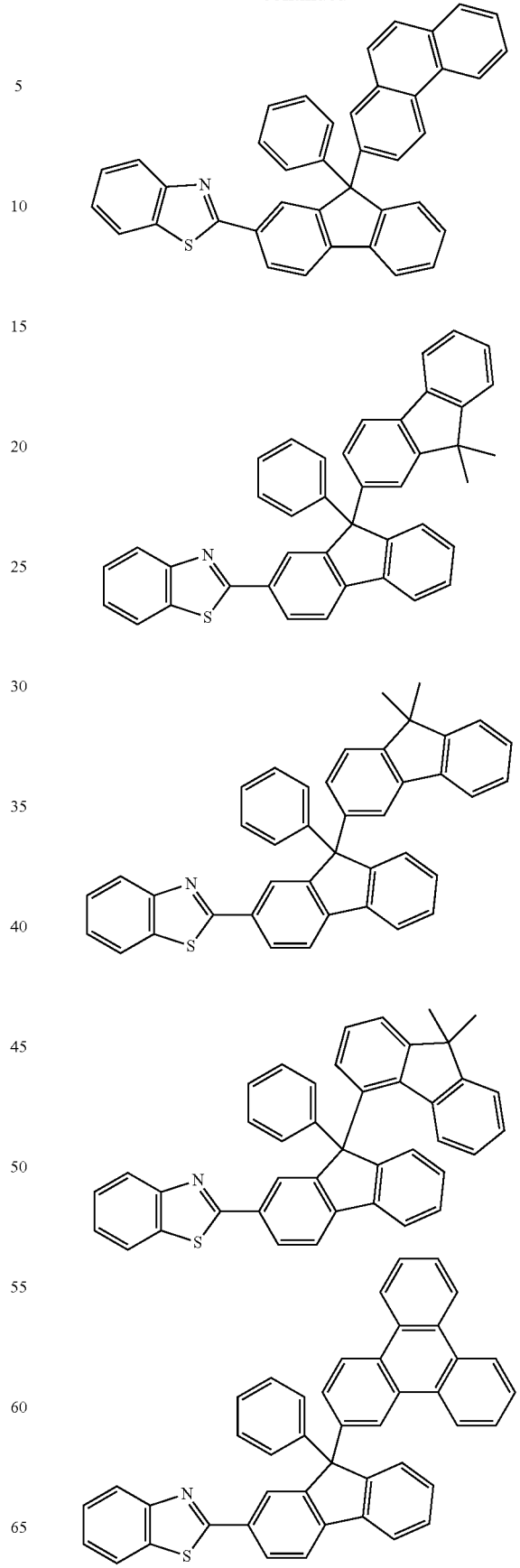

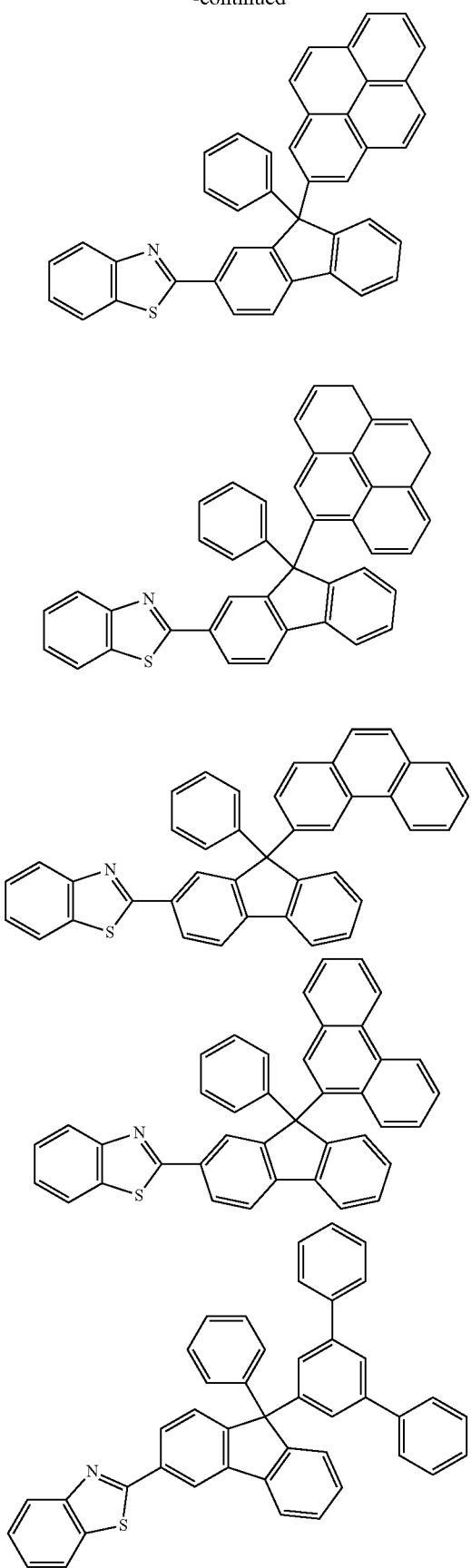
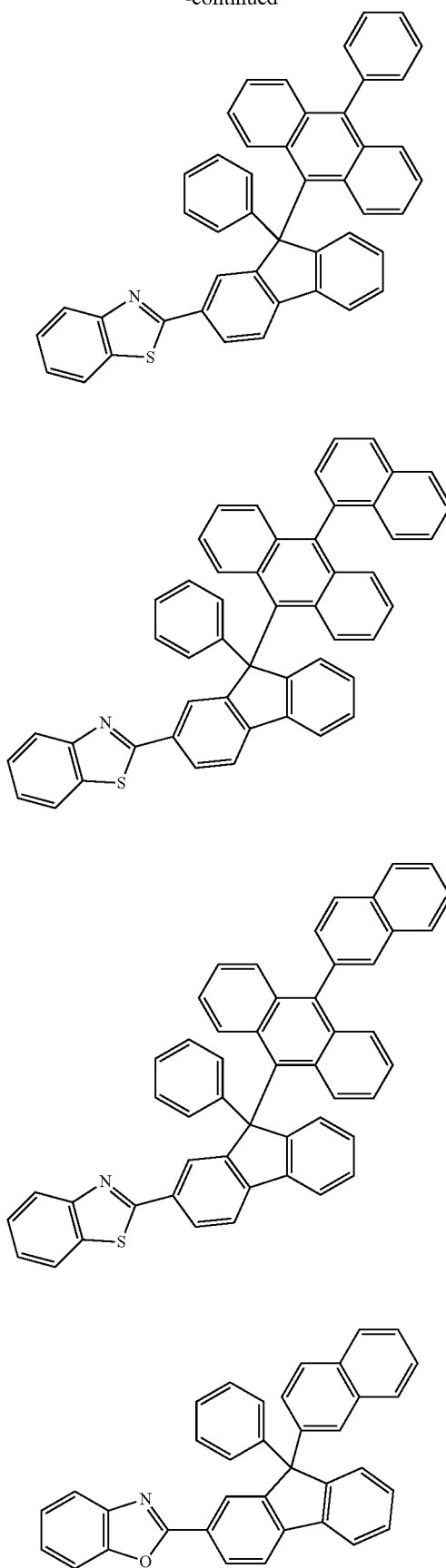

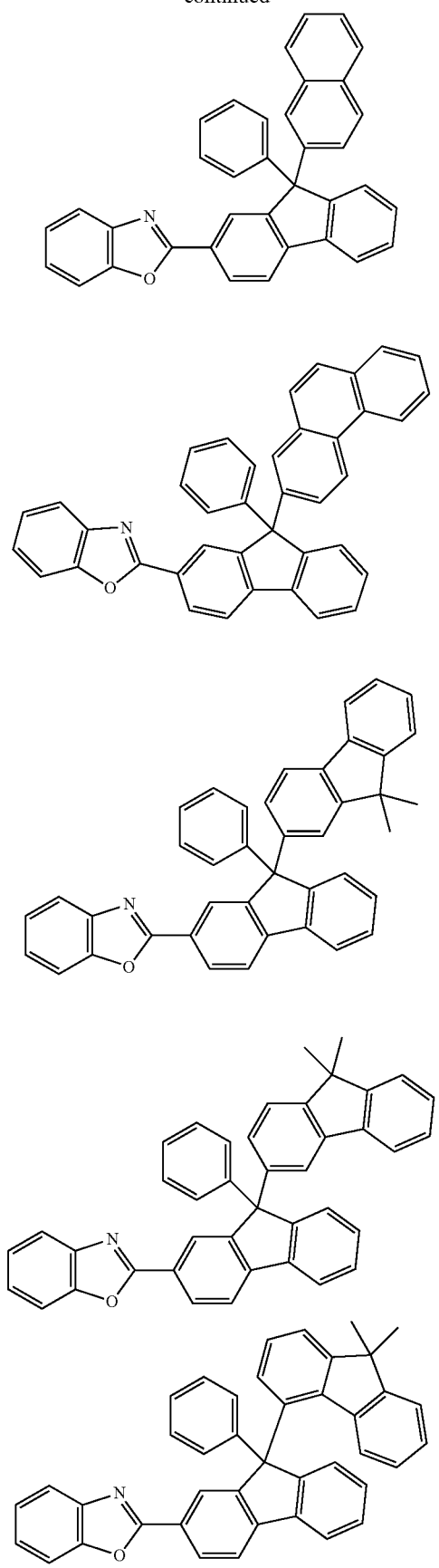
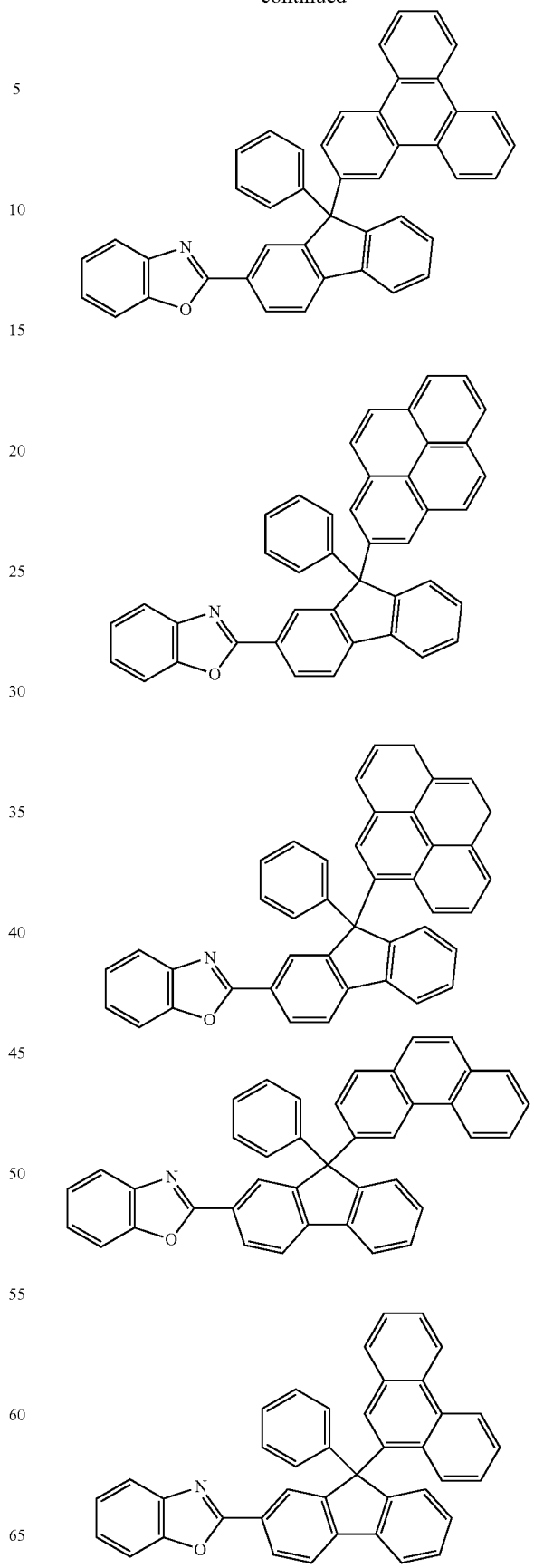

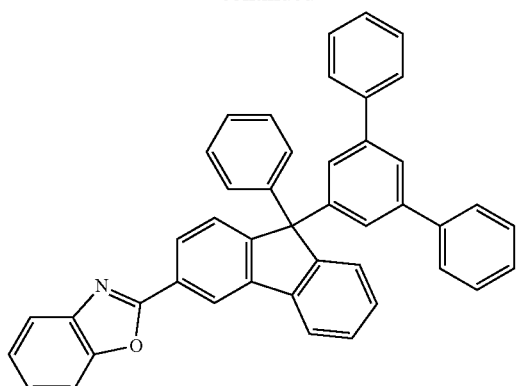
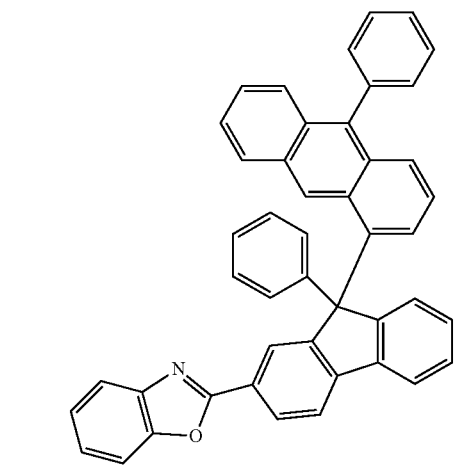
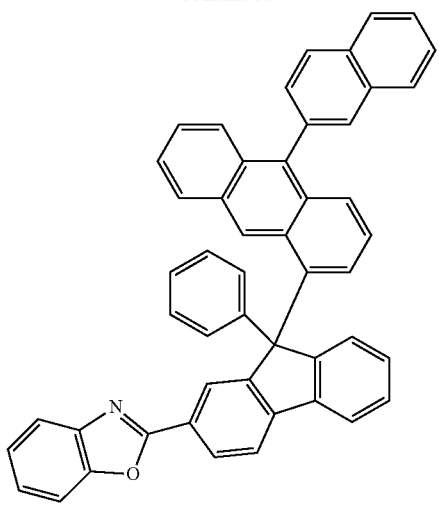
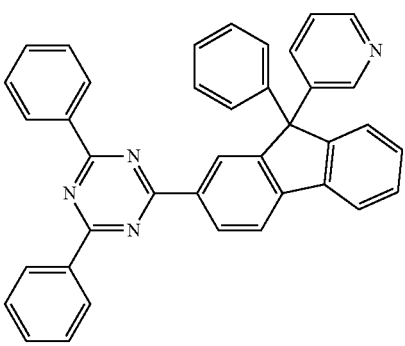
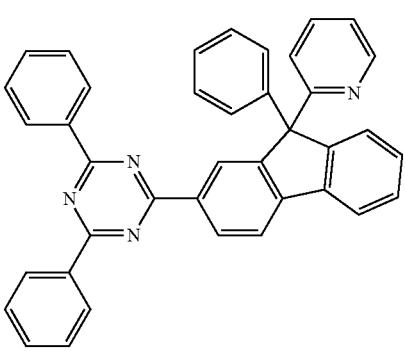
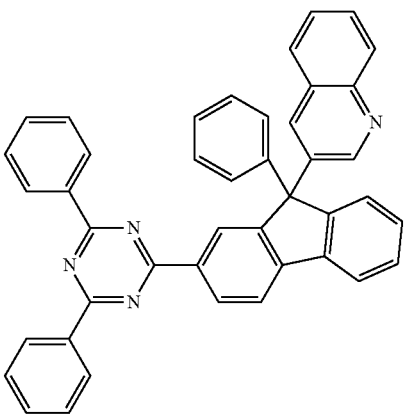

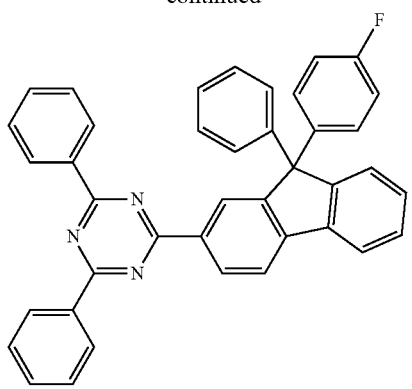
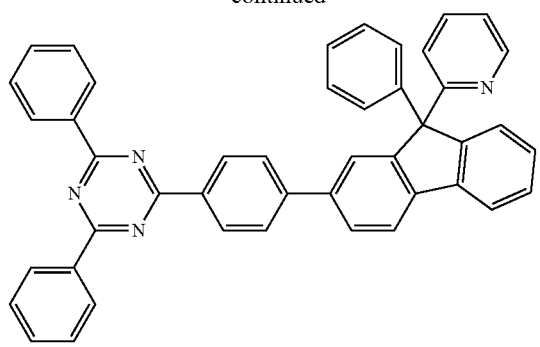
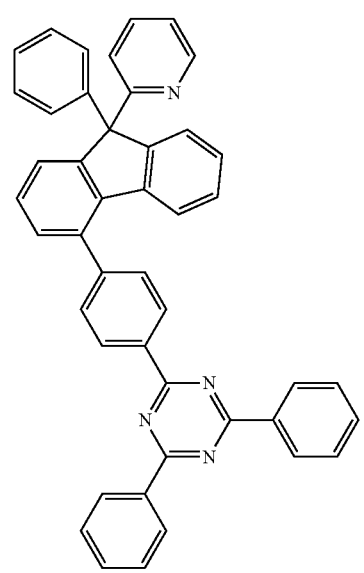
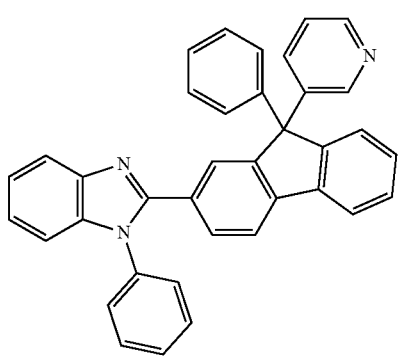
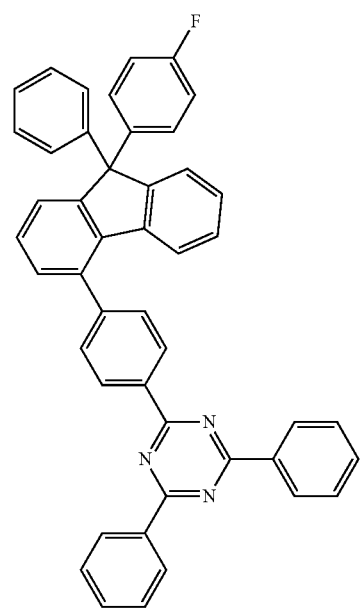
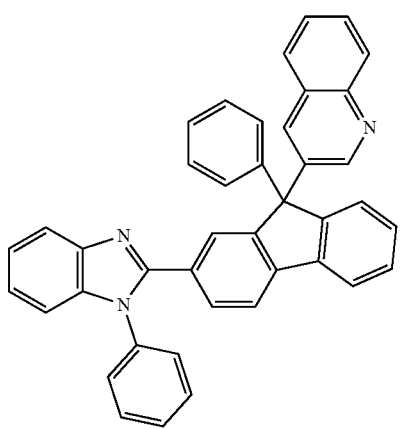

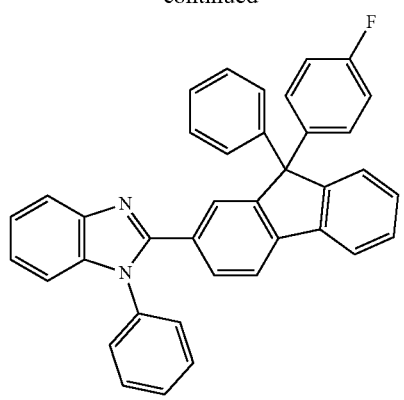
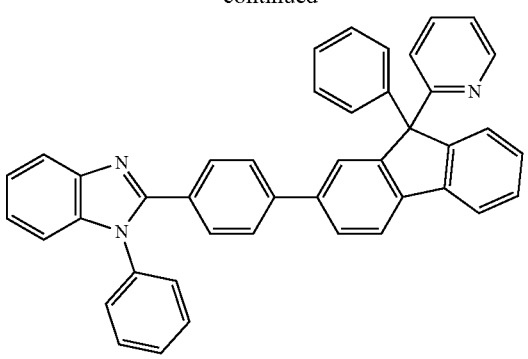
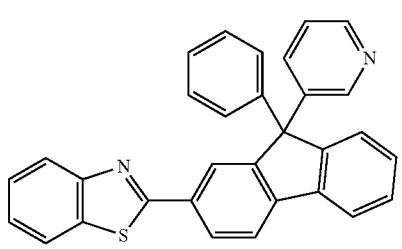
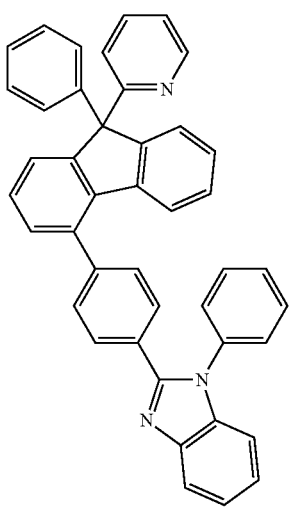
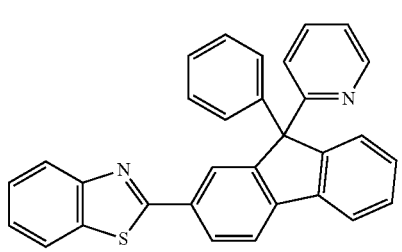
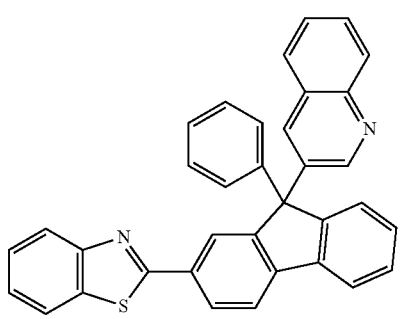
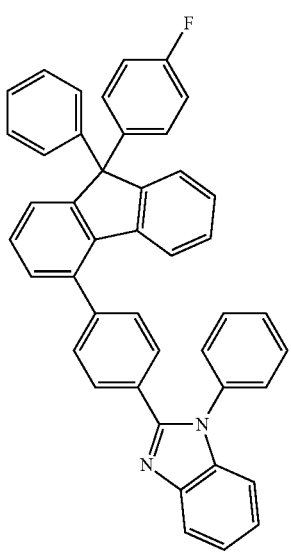
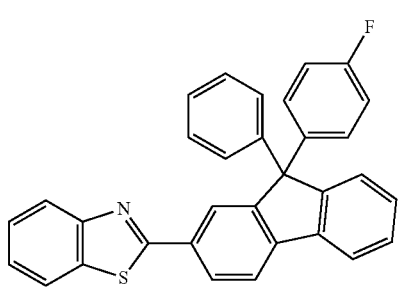

97
-continued
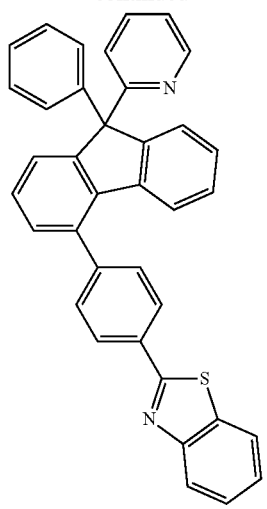
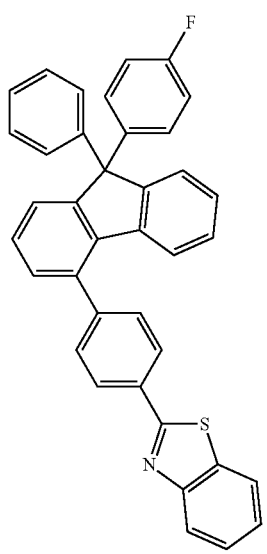
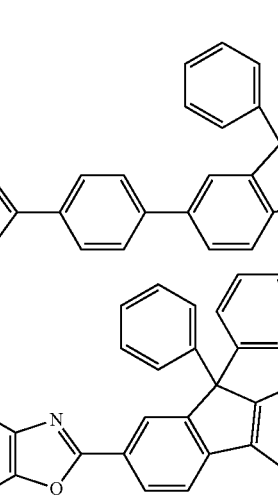
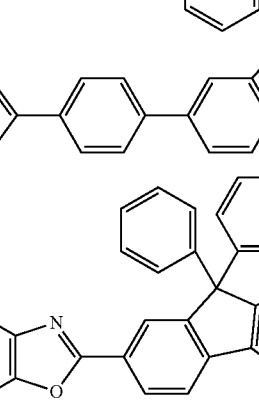
98
-continued
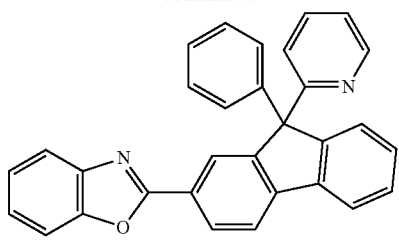
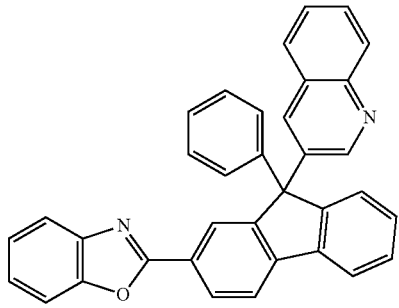
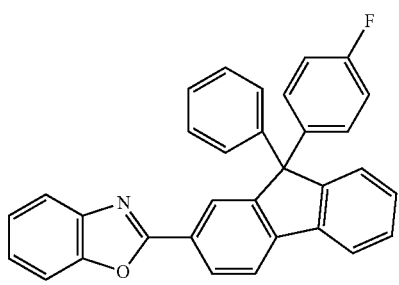
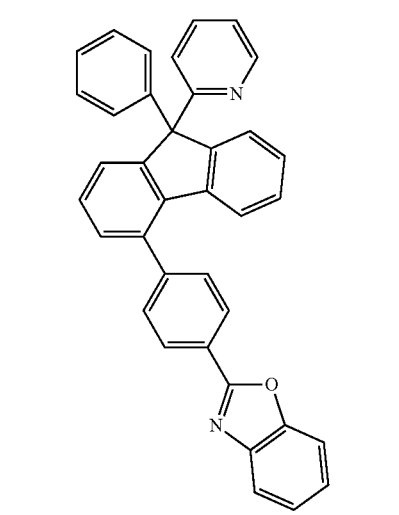

-continued

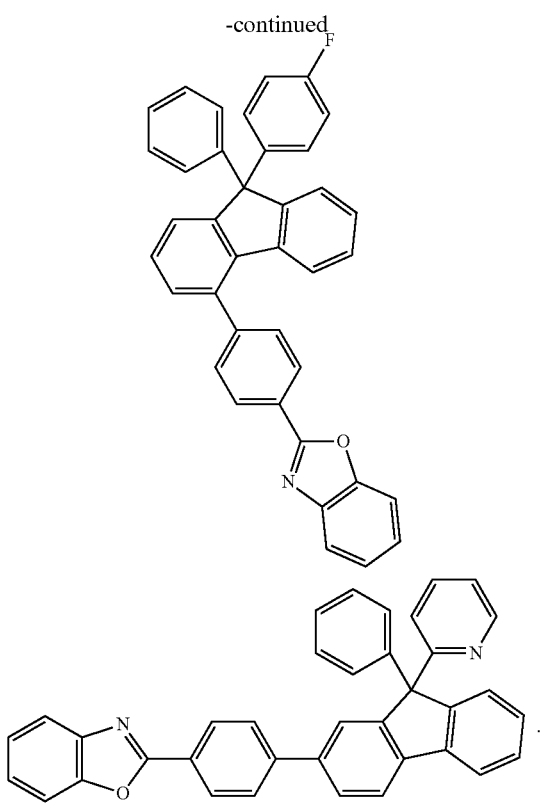

8. An organic electronic device comprising:
a first electrode;
a second electrode provided opposite to the first electrode; and
one or more organic material layers provided between the first electrode and the second electrode,
wherein the one or more organic material layers comprise the compound of claim 1.

9. The organic electronic device of claim 8, wherein the one or more organic material layers comprise an electron injection layer, an electron transfer layer or a layer carrying out electron injection and electron transfer at the same time, and the electron transfer layer, the electron injection layer or the layer carrying out electron injection and electron transfer at the same time comprises the compound.

10. The organic electronic device of claim 8, wherein the one or more organic material layers comprise an electron blocking layer or a hole blocking layer, and the electron blocking layer or the hole blocking layer comprises the compound.

11. The organic electronic device of claim 8, which is selected from the group consisting of an organic light emitting device, an organic phosphorescent device, an organic solar cell, an organic photo conductor (OPC) and an organic transistor.

* * * * *